(12) United States Patent
Ritter et al.

(10) Patent No.: US 9,045,533 B2
(45) Date of Patent: Jun. 2, 2015

(54) MEMBRANE TRANSPORTER NAPI2B (SCL34A2) EPITOPE ANTIBODIES

(71) Applicants: Gerd Ritter, New York, NY (US); Beatrice Yin, New York, NY (US); Anne Murray, New York, NY (US); George Mark, New York, NY (US); Lloyd J. Old, New York, NY (US); Kenneth Lloyd, New York, NY (US); Serhiy Souchelnytskiy, Stockholm (SE); Ivan Gout, London (GB); Valeriy Filonenko, Kviv (UA); Ramziya Kiyamova, Kviv (UA)

(72) Inventors: Gerd Ritter, New York, NY (US); Beatrice Yin, New York, NY (US); Anne Murray, New York, NY (US); George Mark, New York, NY (US); Lloyd J. Old, New York, NY (US); Kenneth Lloyd, New York, NY (US); Serhiy Souchelnytskiy, Stockholm (SE); Ivan Gout, London (GB); Valeriy Filonenko, Kviv (UA); Ramziya Kiyamova, Kviv (UA)

(73) Assignees: Ludwig Institute for Cancer Research Ltd, New York, NY (US); Institute for Molecular Biology and Genetics National Academy of Science of Ukraine, New York, NY (US); Sloan Kettering Cancer Institute, New York, NY (US)

( * ) Notice: Subject to any disclaimer, the term of this patent is extended or adjusted under 35 U.S.C. 154(b) by 0 days.

(21) Appl. No.: 14/037,504

(22) Filed: Sep. 26, 2013

(65) Prior Publication Data
US 2014/0193417 A1 Jul. 10, 2014

Related U.S. Application Data

(62) Division of application No. 12/735,576, filed as application No. PCT/US2009/000579 on Jan. 29, 2009, now Pat. No. 8,603,474.

(60) Provisional application No. 61/062,901, filed on Jan. 29, 2008.

(51) Int. Cl.
| | |
|---|---|
| C12P 21/08 | (2006.01) |
| C12N 5/10 | (2006.01) |
| C07K 16/18 | (2006.01) |
| C07K 16/28 | (2006.01) |
| C07K 14/705 | (2006.01) |
| C07K 16/30 | (2006.01) |
| A61K 39/395 | (2006.01) |
| C07K 7/08 | (2006.01) |
| C07K 14/47 | (2006.01) |
| A61K 39/00 | (2006.01) |

(52) U.S. Cl.
CPC .............. *C07K 16/18* (2013.01); *A61K 39/00* (2013.01); *A61K 2039/505* (2013.01); *C07K 14/705* (2013.01); *C07K 16/28* (2013.01); *C07K 16/30* (2013.01); *C07K 2317/24* (2013.01); *C07K 2317/56* (2013.01); *C07K 2317/565* (2013.01); *C07K 2317/622* (2013.01); *C07K 2317/34* (2013.01); *A61K 39/0011* (2013.01); *A61K 39/39558* (2013.01); *C07K 7/08* (2013.01); *C07K 14/4748* (2013.01)

(58) Field of Classification Search
None
See application file for complete search history.

(56) References Cited

U.S. PATENT DOCUMENTS

| | | | |
|---|---|---|---|
| 4,493,795 | A | 1/1985 | Nestor et al. |
| 5,969,108 | A | 10/1999 | McCafferty et al. |
| 6,319,688 | B1 | 11/2001 | Fields |
| 6,350,858 | B1 | 2/2002 | Fields |
| 2004/0005563 | A1 | 1/2004 | Mack et al. |

FOREIGN PATENT DOCUMENTS

WO  WO2005117986  12/2005

OTHER PUBLICATIONS

Arima, K et al (2002) Glucocorticoid regulation and glycosylation of mouse intestinal type IIb Na-Pi cotransporter during ontogeny Am. J. Physiol. 283:G426-G434.
Bäck, T et al (2005) 211At radioimmunotherapy of subcutaneous human ovarian cancer xenografts: Evaluation of relative biological effectiveness of an α-emitter in vivo J Nucl Med 46(12):2061-2067.
(Continued)

*Primary Examiner* — Christine J Saoud
*Assistant Examiner* — Jon M Lockard
(74) *Attorney, Agent, or Firm* — Klauber & Jackson LLC

(57) ABSTRACT

The present disclosure relates generally to the membrane transporter NaPi2b (SLC34A2) as a target for therapy, including immunotherapy, and particularly cancer therapy. The SLC34A2 epitope peptide encompassing amino acids 312-340 of SLC34A2 has been identified as an ovarian cancer epitope using the monoclonal antibody MX35. The invention also relates to the use of SLC34A2 and particularly SLC34A2 peptides in generating antibodies which have anti-tumor or anti-cancer activity or in stimulating an immunological response. The invention further relates to antibodies specifically directed against NaPi2b (SLC34A2) and the SLC34A2 peptide(s), including veneered, chimeric, single chain and humanized antibodies. Methods for generating an immune response and for treatment of tumors and cancer are also provided. Assays for screening and identifying compounds directed against SLC34A2, including the SLC34A2 epitope peptide, and additional antibodies are provided.

8 Claims, 32 Drawing Sheets

(56) References Cited

OTHER PUBLICATIONS

Ball, EV et al (2005) Microdeletions and microinsertions causing human genetic disease common mechanisms of mutagenesis and the role of local DNA sequence complexity Human mutation 26(3):205-213.
Blanchard, A et al (2007) Gene expression profiling of early involuting mammary gland reveals novel genes potentially relevant to human breast cancer Frontiers in Bioscience 12:2221-2232.
Corut, A et al (2006) Mutations in SLC34A2 cause pulmonary alveolar microlithiasis and are possibly associated with testicular microlithiasis Am J Hum Genet 79(4):650-656.
Elgqvist, J et al (2005) Therapeutic efficacy and tumor dose estimations in radioimmunotherapy of intraperitoneally growing OVCAR-3 cells in nude mice with 211At-labeled monoclonal antibody MX35 J Nucl Med 46(11):1907-1915.
Elqgvist, J et al (2006) α-radioimmunotherapy of intraperitoneally growing OVCAR-3 tumors of variable dimensions: outcome related to measured tumor size and mean absorbed dose J Nucl Med 47(8):1342-1350.
Elqqvist, J et al (2006) Fractioned radioimmunotherapy of intraperitoneally growing ovarian cancer in nude mice with At-MX35 F(ab')2: therapeutic efficacy and mielotoxicity Nuclear Med Biol 33(8):1065-1072.
Elgqvist, J et al (2006) Administered activity and metastatic cure probability during radioimmunotherapy of ovarian cancer in nude mice with At-MX35 F(ab') Int. J. Radiation Oncology Biol. Phys. 66(4):1228-1237.
Farley, J et al (2008) Genomic analysis of epithelial ovarian cancer Cell Res. 18(5):538-548.
Feild, JA et al (1999) Cloning and functional characterization of a sodium-dependent phosphate transporter expressed in human lung and small intestine Biochem Biophys Res Commun 258(3):578-582.
Finstad, CL et al (1997) Distribution of radiolabeled monoclonal antibody MX35 F(Ab')2 in tissue samples by storage phosphor screen image analysis: Evaluation of antibody localization to micrometastatic disease in epithelial ovarian cancer Clin. Cancer Res.3(8):1433-1442.
Forster, IC et al (2006) Proximal tubular handling of phosphate: A molecular perspective Kidney International 70 (9):1548-1559.
Frei, P et al (2005) Identification and localization of sodium-phosphate cotransporters in hepatocytes and cholangiocytes of rat liver Am J Physiol Gastrointest Liver Physiol 288(4):G771-G778.
Gryshkova, VS et al (2009) Creation of cellular models for the analysis of sodium-dependent phosphate transporter NaPi2b, a potential marker for ovarian cancer Biopolymers and Cell Natl Acad of Sci of Ukraine UKR 25(2):95-100.
Gryshkova, V et al (2009) The study of phosphate transporter NAPI2B expression in different histological types of epithelial ovarian cancer Exp Oncology 31(1):37-42.
Gryshkova, V et al (2011) Inhibition of sodium-dependent phosphate transporter NaPi2b function with MX35 antibody Biopolymers and Cell 27(3):193-198.
Gryshkova, V et al (2011) Generation of Monoclonal Antibodies Against Tumor-Associated Antigen MX35/sodium-Dependent Phosphate Transporter NaPi2b Hybridoma 30(1):37-42.
Hilfiker, H et al (1998) Characterization of a new murine type II sodium-phosphate cotransporter expressed in mammalian small intestine Proc Natl Acad Sci USA 95(24):14564-14569.
Homann, V et al (2005) Sodium-phosphate cotransporter in human salivary glands: molecular evidence for the involvement of NPT2b in acinar phosphate secretion and ductal phosphate reabsorption Arch Oral Biol. 50(9):759-768.
Huber, K et al (2007) Sodium-dependent phosphate transport across the apical membrane of alveolar epithelium in caprine mammary gland Comparative Biochemistry and Physiology 146(2):215-222.
Hultborn, R et al (2006) Pharmacokinetics and dosimetry of 211at-MX35 F(ab')2 in therapy of ovarian cancer-preliminary results from an ongoing phase I study Cancer Biother Radiopharm 21:373-381.
Huqun, I et al (2007) Mutations in the SLC34A2 gene are associated with pulmonary alveolar microlithiasis Am J Respi Crit Care Med 175(3):263-268. (PMID: 17095743).
Jarzab, B et al (2005) Gene expression profile of papillary thyroid cancer: sources of variability and diagnostic implications Cancer Res. 65(4):1587-1597.
Katai, K et al (1999) Regulation of intestinal Na+-dependent phosphate co-transporters by a low-phosphate diet and 1,25-dihydroxyvitamin D3 Biochem. J, 343(Pt 3):705-712.
Kiyamova, R et al (2008) Development of monoclonal antibodies specific for the human sodium-dependent phosphate cotransporter NaPi2b Hybridoma 27(4):277-284.
Lanaspa, MA et al (2007) Interaction of MAP17 with NHERF3/4 induces translocation of the renal Na/Pi IIa transporter to the trans-Golgi Am. J. Physiol. Renal Physiol 292(1):F230-242.
Lundquist, P et al (2007) Type II Na+-P. cotransporters in osteoblast mineral formation; regulation by inorganic phosphate Cell Physiol Biochem 19(1-4):43-56.
Matsuo, A et al (2005) Inhibitory effect of JTP-59557, a new triazole derivative, on intestinal phosphate transport in vitro and in vivo Eur J Pharmacol 517(1-2): (PMID:15961073).
Mattes, M et al (1987) Mouse monoclonal antibodies to human epithelial differentiation antigens expressed on the surface of ovarian carcinoma ascites cells Cancer Res 47(24 Pt 1):6741-6750.
Miyoshi, K et al (2001) Signal transducer and activator of transcription (Stat) 5 controls the proliferation and differentiation of mammary alveolar epithelium J Cell Biol 155(4):531-542.
Miyamoto, K et al (2005) Inhibition of intestinal sodium-dependent inorganic phosphate transport by fibroblast growth factor 23 Ther. Apher. Dial 9(4):331-335.
Murer, H et al (2001) Molecular mechanisms in proximal tubular and small intestinal phosphate Molecular Membrane Biology 18(1):3-11.
Murer, H et al (2004) The sodium phosphate cotransporter family SLC34 Pflugers Arch Eur J Physiol 447(5):763-767.
Palmada, M et al (2004) Regulation of intestinal phosphate cotransporter NaPi IIb by ubiquitin ligase Nedd4-2 and by serum- and glucocorticoid-dependent kinase 1 Am. J. Physiol. Gastrointest. Liver Physiol. 287(1):G143-G150.
Rangel, LB et al (2003) Characterization of novel human ovarian cancer-specific transcripts (HOSTs) identified by serial analysis of gene expression Oncogene 22(46):7225-7232.
Rubin, SC et al (1993) Biodistribution and intraoperative evaluation of radiolabeled monoclonal antibody MX35 in patients with epithelial ovarian cancer Gynecol Oncol 51(1):61-66. (PMID:244176).
Shojaiefard, M et al (2006) Stimulation of the intestinal phosphate transporter SLC34A2 by the protein kinase mTOR Biochem Biophys Res Commun 345(4):1611-1644.
Stauber, A et al (2005) Regulation of intestinal phosphate transport. II. Metabolic acidosis stimulates Na(+)-dependent phosphate absorption and expression of the Na(+)-P(i) cotransporter NaPi2b in small intestine Am J Physiol Gastrointest Liver Physiol 288(3):G501-G506.
Traebert, M et al (1999) Expression of a type II sodium-phosphate cotransporter in murine type II alveolar epithelial cells Am J Physiol 277(5 Pt 1)::L868-L873.
Welshinger, M et al (1997) Initial immunochemical characterization of MX35 ovarian cancer antigen Gynecol Oncol 67 (2):188-192.
Xu, H et al (1999) Molecular cloning, functional characterization, tissue distribution, and chromosomal localization of a human, small intestinal sodium-phosphate (Na+-Pi) transporter (SLC34A2) Genomics 62(2):281-284.
Xu, H et al (2001) Regulation of the human sodium-phosphate cotransporter NaPi2b gene promoter by epidermal growth factor Am. J. Physiol 280(3):C628-C636.
Xu, Y et al (2003) Sodium-Inorganic Phosphate Cotransporter NaPi2b in the Epididymis and Its Potential Role in Male Fertility Studied in a Transgenic Mouse Model Biology of reproduction 69(4):1135-1141.
Xu, H et al (2003) Regulation of intestinal NaPi2b cotransporter gene expression by estrogen // Am. J. Physiol. Gastrointest Liver Physiol 285(6):G1317-G1324.
Yin, B et al (2008) Monoclonal antibody MX35 detects the membrane transporter NaPi2b (SLC34A2) in human carcinomas; a new target for cancer immunotherapy Cancer Immun 8:3.

FIGURE 1C

```
  1  mapwpelgda qpopdkyleq aagqqptapd kaketnktdn teapvtkiel lpsystatli
 61  daptevddpw niptlqdsqi kwserdtkqk ileffqgigr lilllgflyf fvcsldilas
121  afqlvggkma gqffsnssim sopllglvig vlvtvlvqss ststsivvsm vssslltvra
181  alpiimgani gtsltntiva lmqvgdrsef rrafagatvh dffnwlsvlv llpvevathy
241  lelitqlive sfhfkngeda pdllkvitkp ftklivgldk kvisqiamod ekakNkslvk
301  iwcktftNkt qiNvcvpsta Nctspslcwt dgiqnwcmkN vtykeniakc qhifvnfhlp
361  dlavgtilli lsllvlcqol imivkilgsv lkgqvatvik ktintdfpfp fawltgylai
421  lvgaqmtfiv qsssvftsal tpliqiqvit lerayplltq snigttttai laalaspqna
481  lrsslqialc hfffnisgil lwyplpftrl plrmakylgn isakyrwfav fylllffli
541  pltvfglsla qwrvlvqvqv pvvflillvl clrllqsrcp rvlpkklqnw nflplwarsl
601  kpwdavvskf tgcfgmrccc ccrvccracc llcgcpkccr cskccedlee aqeqqdvpvk
661  apetfdniti sreaqqevpa sdsktectal
```

FIGURE 5

```
            Atgggatggagctgtatcatcttcttggtagcaacagctaca
         M  G  W  S  C  I  I  F  L  V  A  T  A  T ggtgtccactcccaggtgcaattgaagcagtctggggctgagctggtgaagcctggggcc
 G  V  H  S  Q  V  Q  L  K  Q  S  G  A  E  L  V  K  P  G  A
                        CDR1
tcagtgaagatgtcctgtaaggcttccggctacacatttaccgggtacaatatacactgg
 S  V  K  M  S  C  K  A  S  G  Y  T  F  T  G  Y  N  I  H  W
                                 CDR2
gtaaagcagacacctggacagggcctggaatggattggagctatttatccaggaaatggt
 V  K  Q  T  P  G  Q  G  L  E  W  I  G  A  I  Y  P  G  N  G
gatacttcctacaaacagaagttcagaggcaaggcctcattgactgcagacacatcctcc
 D  T  S  Y  K  Q  K  F  R  G  K  A  S  L  T  A  D  T  S  S
agtacagtctatatgcagctcagcagcctgacatctgaggactctgcggtctattactgt
 S  T  V  Y  M  Q  L  S  S  L  T  S  E  D  S  A  V  Y  Y  C
       CDR3
gcaagaggggagacagctcgggctactttgcttactggggccaagggactctggtcact
 A  R  G  E  T  A  R  A  T  L  L  T  G           W  G  Q  G  T  L  V  T gtctctgca
 V  S  A
```

FIGURE 6

```
gaattcgcccttatggtgtcctcagctcagttccttggtctcctgttgctctgttttcaa
          M  V  S  S  A  Q  F  L  G  L  L  L  L  C  F  Q
ggtaccagatgtgatatccagatgacacagactacatcctccctgcctgcctctctggga
  G  T  R  C  D  I  Q  M  T  Q  T  T  S  S  L  P  A  S  L  G
gacagagtcaccatcagttgcagtgcaagtcaggacattggcaattttttaaactggtat
  D  R  V  T  I  S  C  S  A  S  Q  D  I  G  N  F  L  N  W  Y
caacagaaaccagatggaactgttaaagtcctgatctattacacatcaagtttatactca
  Q  Q  K  P  D  G  T  V  K  V  L  I  Y  Y  T  S  S  L  Y  S
ggagtcccatcaaggttcagtggcagtgggtctgggacagactattctctcaccatcagc
  G  V  P  S  R  F  S  G  S  G  S  G  T  D  Y  S  L  T  I  S
aacctggaacctgaagatattgccacttactattgtcaacagtatagtaaacttccgctc
  N  L  E  P  E  D  I  A  T  Y  Y  C  Q  Q  Y  S  K  L  P  L
acgttcggtgctgggaccaagctcgagctgaaacgg
     F  G  A  G  T  K  L  E  L  K  R
```

FIGURE 7
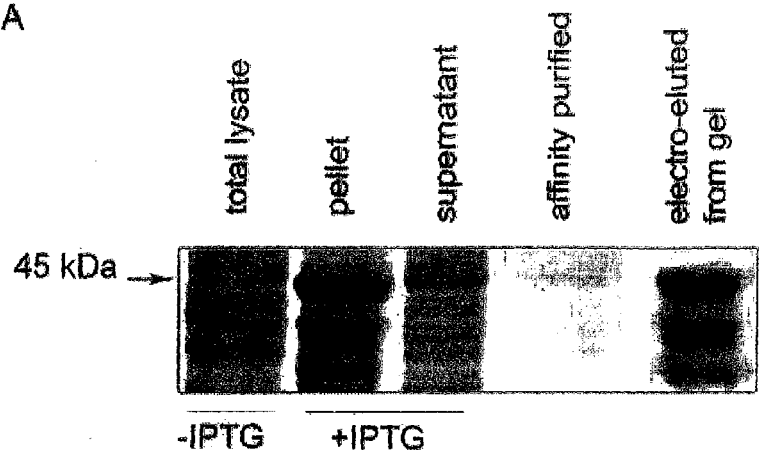
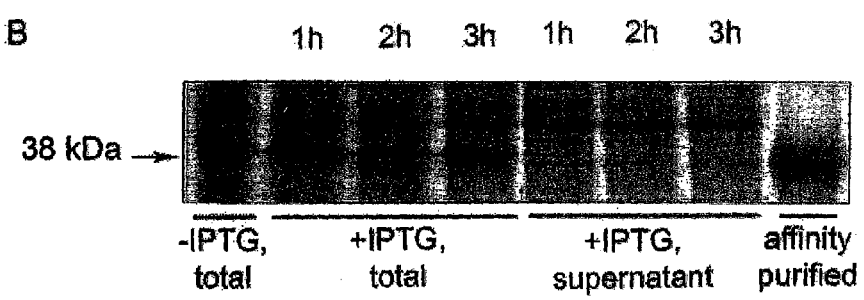
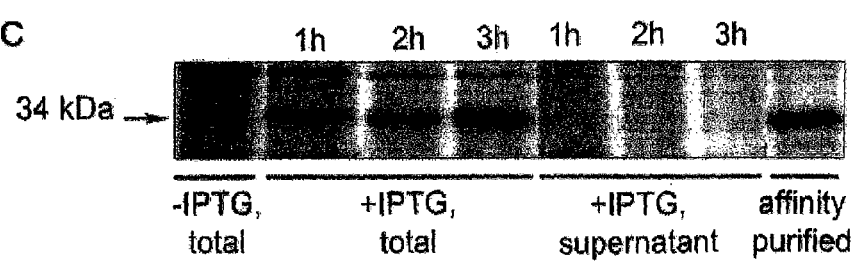

FIGURE 10
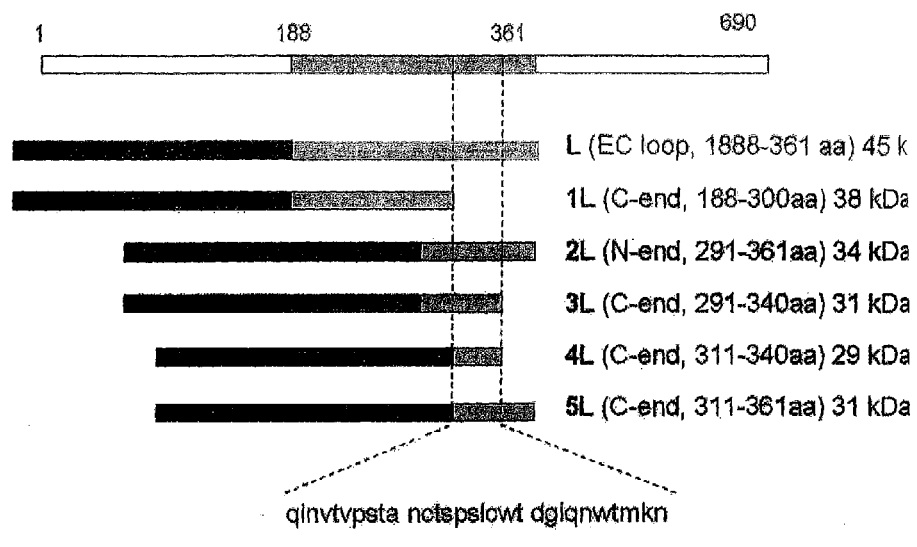
qlnvtvpsta nctspslcwt dglqnwtmkn
GST-tag (26kDa)
ECL - extracellular loop
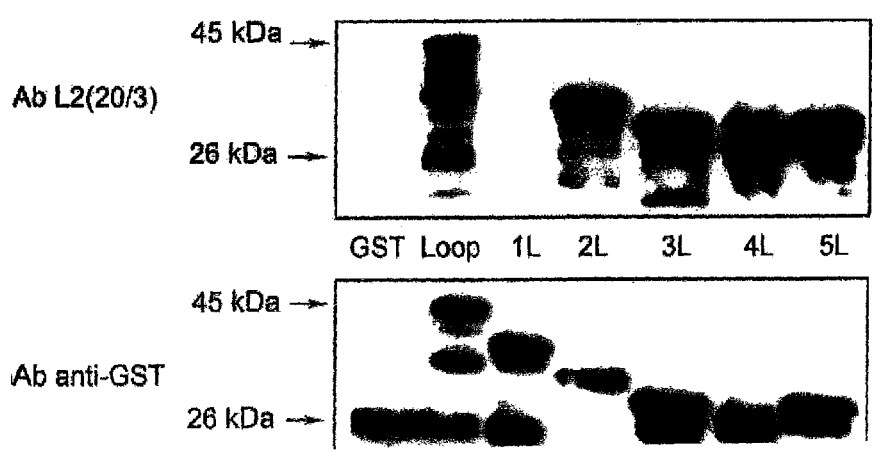

```
                                                         CDR1
murine      MGWSCIIFLVATATGVHSQVQLKQSGAELVKPGASVKMSCKAS GYTFTGYNIH  WVKQTPG 60
humanized   --------------GVHSQVQLVQSGAEVVKPGASVKMSCKAS GYTFTGYNIH  WVKQAPG 46
                          ******* *****:************* ********** ****:**
                    CDR2                                                CDR3
murine      QGLEWIG AIYPGNGDTSYKQKFRG KASLTADTSSSTVYMQLSSLTSEDSAVYYCAR GETA 120
humanized   QGLEWIG AIYPGNGDTSYKQKFRG RATLTADTSTSTVYMELSSLRSEDSAVYYCAR GETA 106
            ***** *************** :*:****:: ******** ** murine      RATFAY WGQGTLVTVSA- 137
humanized   RATFAY WGQGTLVTVSSG 124
            ****** **********:
```

(B)

```
                                                        CDR1
murine      MVSSAQFLGLLLLCFQGTRCDIQMTQTTSSLPASLGDRVTISC SASQDIGNFLN WYQQKP 60
humanized   ---------------GVHSDIQMTQSPSSLSASVGDRVTITC SASQDIGNFLN WYQQKP 44
                           *.:.******::.***.**:******:* *********** ******
                                                              CDR3
murine      DGTVKVLIY YTSSLYS GVPSRFSGSGSGTDYSLTISNLEPEDIATYYC QQYSKLPLT 117
humanized   GKTVKVLIY YTSSLYS GVPSRFSGSGSGTDYTLTISSLQPEDFATYYC QQYSKLPLT 101
            .***** *** **********:**:*:*: ******* murine      FGAGTKLELKR 128
humanized   FGQGTKLELKR 112
            ** ********
```

OVCAR-3 – ovarian carcinoma

| Sample | Positive cells (%) | Median fluorescence intensity |
|---|---|---|
| Cells only | 1,31 | 3,66 |
| Murine FITC-conjugate control | 1,46 | 3,7 |
| Human FITC-conjugate control | 1,54 | 3,68 |
| Zenapax® | 1,63 | 3,53 |
| muMX35 | 95,71 | 182,62 |
| huMX35 | 94,64 | 173,97 |

SK-RC-18 – renal carcinoma

| Sample | Positive cells (%) | Median fluorescence intensity |
|---|---|---|
| Cells only | 0,42 | 2,69 |
| Murine FITC-conjugate control | 0,65 | 2,74 |
| Human FITC-conjugate control | 0,88 | 2,78 |
| Zenapax® | 0,45 | 2,96 |
| muM35 | 94,69 | 219,9 |
| huMX35 | 98,75 | 218,42 |

SW626 – ovarian metastasis (primary tumor: colon)

| Sample | Positive cells (%) | Median fluorescence intensity |
|---|---|---|
| Cells only | 2,19 | 3,14 |
| Murine FITC-conjugate control | 2,08 | 3,07 |
| Human FITC-conjugate control | 2,14 | 2,93 |
| Zenapax® | 2,51 | 3,23 |
| muM35 | 2,23 | 3,18 |
| huMX35 | 2,79 | 3,4 |
| hu3S193 | 99,11 | 179,22 |

LoVo – colorectal carcinoma

| Sample | Positive cells (%) | Median fluorescence intensity |
|---|---|---|
| Cells only | 2,58 | 2,53 |
| Murine FITC-conjugate control | 2,9 | 2,65 |
| Human FITC-conjugate control | 2,61 | 2,59 |
| Zenapax® | 3,2 | 2,7 |
| muM35 | 3,53 | 2,88 |
| huMX35 | 2,63 | 2,61 |
| hu3S193 | 55,19 | 12,81 |

FIGURE 16

```
gtgaaaaaattattattcgcaattcctttagttgttcctttctatgcggcccagccggcc
 V  K  K  L  L  F  A  I  P  L  V  V  P  F  Y  A  A  Q  P  A
caggtgcagctggtgcagagcggcgctgaagtggtgaagcctggcgctagcgtgaagatg
 Q  V  Q  L  V  Q  S  G  A  E  V  V  K  P  G  A  S  V  K  M
agctgcaaggccagcggctacaccttcaccggctacaacatccattgggtgaagcaggct
 S  C  K  A  S  G  Y  T  F  T  G  Y  N  I  H  W  V  K  Q  A
ccaggccagggcctcgaatggatcggcgccatctaccccggcaacggcgatacctcttac
 P  G  Q  G  L  E  W  I  G  A  I  Y  P  G  N  G  D  T  S  Y
aagcagaagttcaggggcagggctaccctcaccgccgacaccagcaccagcaccgtgtac
 K  Q  K  F  R  G  R  A  T  L  T  A  D  T  S  T  S  T  V  Y
atggaactgtccagcctgagaagcgaggacagcgccgtgtactactgcgccaggcgcgag
 M  E  L  S  S  L  R  S  E  D  S  A  V  Y  Y  C  A  R  G  E
accgccagggccaccttcgcctactggggccaggcaccctggtgactgtatcatccggt
 T  A  R  A  T  F  A  Y  W  G  Q  G  T  L  V  T  V  S  S  G
ggaggcggttcaggcggaggtggctctggcggtgccggatcggacatccagatgacccag
 G  G  G  S  G  G  G  G  S  G  G  G  S  D  I  Q  M  T  Q
agccccagcagcctgagcgccagcgtgggcgacagggtgaccatcacctgcagcgccagc
 S  P  S  S  L  S  A  S  V  G  D  R  V  T  I  T  C  S  A  S
caggacatcggcaactttctgaactggtatcagcagaagcccggcaagaccgtcaaggtg
 Q  D  I  G  N  F  L  N  W  Y  Q  Q  K  P  G  K  T  V  K  V
ctgatctactacaccagctccctgtacagcggcgtgcccagcaggttcagcggcagcggc
 L  I  Y  Y  T  S  S  L  Y  S  G  V  P  S  R  F  S  G  S  G
tccggcaccgactacaccctgaccatcagcagcctgcagcccgaggacttcgccacctac
 S  G  T  D  Y  T  L  T  I  S  S  L  Q  P  E  D  F  A  T  Y
tactgccagcagtacagcaagctgcccctgaccttcggccagggcaccaaactggaactc
 Y  C  Q  Q  Y  S  K  L  P  L  T  F  G  Q  G  T  K  L  E  L
aaagcggccgcaggtgcgccggtgccgtatccggatccgctggaaccgcgtgccgcatag
 K  A  A  A  G  A  P  V  P  Y  P  D  P  L  E  P  R  A  A  -
```

Key: Signal Sequence
Variable Heavy Chain
Linker Region
Variable Light Chain
E-Tag

FIGURE 17

```
gtgaaaaaattattattcgcaattcctttagttgttcctttctatgcggcccagccggcc
 V  K  K  L  L  F  A  I  P  L  V  V  P  F  Y  A  A  Q  P  A
caggtgcaattgaagcagtctggggccgagctggtgaagccaggcgccagcgtgaagatg
 Q  V  Q  L  K  Q  S  G  A  E  L  V  K  P  G  A  S  V  K  M
agctgcaaggccagcggctacaccttcaccggctacaacatccactgggtcaagcagacc
 S  C  K  A  S  G  Y  T  F  T  G  Y  N  I  H  W  V  K  Q  T
ccaggccagggcctcgagtggatcggcgccatctaccccggcaacggcgacaccagctac
 P  G  Q  G  L  E  W  I  G  A  I  Y  P  G  N  G  D  T  S  Y
aagcagaagttcaggggcaaggccagcctcaccgccgacaccagcagcagcaccgtgtac
 K  Q  K  F  R  G  K  A  S  L  T  A  D  S  S  S  T  V  Y
atgcagctgtccagtctcaccagcgaagatagcgccgtgtactactgtgccagaggcgag
 M  Q  L  S  S  L  T  S  E  D  S  A  V  Y  Y  C  A  R  G  E
accgccagagccaccttcgcctactggggccagggcaccctggtgaccgtgtcatccggt
 T  A  R  A  T  F  A  Y  W  G  Q  G  T  L  V  T  V  S  S  G
ggaggcggttcaggcggaggtggctctggcggtggcggatcggatatccagatgacccag
 G  G  G  S  G  G  G  G  S  G  G  G  G  S  D  I  Q  M  T  Q
accacctccagcctgcccgccagcctgggcgacagagtgaccatcagctgctccgccagc
 T  T  S  S  L  P  A  S  L  G  D  R  V  T  I  S  C  S  A  S
caggacatcggcaactttctgaactggtatcagcagaagcccgacggcaccgtcaaggtg
 Q  D  I  G  N  F  L  N  W  Y  Q  Q  K  P  D  G  T  V  K  V
ctcatctactacaccagcagcctgtacagcggcgtgccaagcagattcagcggcagcggc
 L  I  Y  Y  T  S  S  L  Y  S  G  V  P  S  R  F  S  G  S  G
tccggcaccgactacagcctcaccatctccaacctggagccagaggacatcgccacctac
 S  G  T  D  Y  S  L  T  I  S  N  L  E  P  E  D  I  A  T  Y
tactgccagcagtacagcaagctgccactcaccttcggagccggcaccaagctggagctg
 Y  C  Q  Q  Y  S  K  L  P  L  T  F  G  A  G  T  K  L  E  L
aaagcggccgcaggtgcgccggtgccgtatccggatccgctggaaccgcgtgccgcatag
 K  A  A  A  G  A  P  V  P  Y  P  D  P  L  E  P  R  A  A  -
```

Key: Signal Sequence
Variable Heavy Chain
Linker Region
Variable Light Chain
E-Tag ▲ cysteine residues ■ deletion of 461...519 amino acids (59 amino acids in C-terminus)

● T330V substitution

⬡ deletion of 591...596 amino acids (6 amino acids in C-terminus)

US 9,045,533 B2

MEMBRANE TRANSPORTER NAPI2B (SCL34A2) EPITOPE ANTIBODIES

CROSS REFERENCE TO RELATED APPLICATIONS

The present application is a Divisional of the National Stage application Ser. No. 12/735,576, filed Dec. 9, 2010, which claims priority from PCT Application No. PCT/US2009/000576 filed Jan. 29, 2009, which claims priority from U.S. Provisional Application Ser. No. 61/062,901 filed Jan. 29, 2008. Applicants claim the benefits of 35 U.S.C. §120 as to the PCT Application and priority under 35 U.S.C. §119 as to the said U.S. Provisional application, and the entire disclosures of both applications are incorporated herein by reference in their entireties.

FIELD OF THE INVENTION

The present invention relates to the membrane transporter NaPi2b (SLC34A2) as a target in cancer therapy, including immunotherapy. The invention further relates to the extracellular region of SLC34A2 as a specific target and epitope in therapy and immunotherapy. The invention relates to antibodies and fragments thereof which bind thereto, and particularly which are directed against the epitope peptide of extracellular domain amino acids, particularly amino acids 312 to 340. SLC34A2 antibodies and immunogenic compositions of the present invention may also be used in therapy in combination with chemotherapeutics or anti-cancer agents.

BACKGROUND OF THE INVENTION

Epithelial ovarian cancer is one of the most common gynecologic malignancies and the fifth most frequent cause of cancer death in women with an estimated incidence of about 15,000 in 2006 in the US alone. Most patients present with advanced disease and the mortality rate is approximately 65% of the incidence rate. Debulking surgery and platinum-based combination chemotherapy (including taxanes) are current treatment modalities; however the majority of patients with relapsed epithelial ovarian cancer eventually succumb to the disease. Thus, there is a need for novel treatment modalities in ovarian cancer, including targeted therapies such as immunotherapy with monoclonal antibodies or cancer vaccine-based approaches.

Monoclonal antibody MX35 was generated from mice immunized with a cocktail of human ovarian carcinoma cells prepared from four different surgical specimens. Reactivity by immunohistochemistry with cryostat sections of a panel of frozen human tissues was used as the major hybridoma selection criteria (1). Mab MX35 showed homogeneous reactivity with approximately 90% of human ovarian epithelial cancers and a limited number of normal tissues. Subsequently, the localization and biodistribution of radiolabeled murine antibody was studied in patients with ovarian carcinoma in phase I clinical trials. Intact MX35 antibody targeted well to tumors in patients with ovarian cancer (2) and F(ab)$_2$ of MX35 was shown to localize to micrometastatic ovarian carcinoma deposits within the peritoneal cavity (3). In preparation for the use of the antibody for radioimmunotherapy, e.g. as a targeted carrier of radionuclides in patients with ovarian carcinoma, the murine antibody and its fragments are currently being investigated in preclinical models (4, 5) and in a phase I clinical trial in patients with ovarian cancer as carrier of the alpha-particle-emitting nuclide astatine-211 (6).

Despite the use of mAb MX35 in clinical trials the detailed molecular nature of the antigen recognized by mAb MX35 has not yet been identified. Initial immunochemical characterization has described the MX35 antigen as a 95 kDa cell surface glycoprotein with the antigenic epitope stabilized by disulfide bonds (7).

The identification and characterization of the mAb MX35 antigen and epitope would provide a target for immunotherapy of cancer with monoclonal antibodies and for other cancer treatment modalities, including improved and directed cancer therapeutic compounds, and a recognized marker for diagnostic and monitoring purposes.

The citation of references herein shall not be construed as an admission that such is prior art to the present invention.

SUMMARY OF THE INVENTION

In a broad aspect, the present invention provides an antigen or epitope target for cancer therapy, including immunotherapy. In particular a key ovarian cancer epitope, which is also a therapeutic target and diagnostic marker, has been identified. The membrane transporter, particularly a sodium-dependent phosphate transporter (NaPi2b) corresponding to SLC34A2 has now been identified as the antigen recognized by antibody mAb MX35. In particular, the MX35 antibody recognizes and is specific for the epitope encompassed by amino acids 312-340 of SLC34A2. Isolated antibodies or fragments thereof which recognize amino acids 312-340 of SLC34A2 are provided herein. The antibodies of the invention recognize the 312-340 epitope, which is evident or reactive in tumorigenic cells, particularly ovarian cancer cells, tumors and cell lines. SLC34A2 provides a new and novel therapeutic target for cancer, particularly ovarian cancer.

The identification of the MX35 antigen as the sodium-dependent phosphate transport protein 2b (NaPi2b) SLC34A2, now provides a new family of potential cell surface targets for immunotherapy of cancer with monoclonal antibodies. More generally, SLC34A2 provides a target for development and screening of therapeutic agents, including anticancer compounds. Assays and methods utilizing and based on the extracellular domain of SLC34A2, particularly extracellular domain region amino acids 312-340 or fragments thereof, are provided herein.

The present inventors have identified additional and novel monoclonal antibodies, which specifically recognize SLC34A2, and particularly are reactive with and bind the epitope of amino acids 312-340 of SLC34A2. In particular, the antibodies of the present invention recognize an SLC34A2 epitope which is found particularly in tumorigenic cells, including ovarian cancer cells. The antibodies of the present invention are further exemplified by the antibodies mAb described herein. The antibodies of the present invention specifically recognize the extracellular domain of SLC34A2, which includes amino acids 188-361, and most particularly the epitope encompassed in amino acids 312-340 of SLC34A2.

The antibodies of the present invention can specifically categorize the nature of cells, by staining or otherwise recognizing those cells wherein cancer, including thyroid cancer, ovarian cancer, lung cancer, kidney cancer, and breast cancer, particularly ovarian cancer, is present. Further, the antibodies of the present invention, may be used in immunotherapy, immunodiagnostics, immunotargeting, and cancer vaccines for therapeutic and/or prophylactic mediation of cancer.

In a preferred aspect, the antibody is one which has the characteristics of the antibody which the inventors have identified and characterized, in particular recognizing SLC34A2, particularly directed against or reactive with amino acids 312-340 of SLC34A2. In a particularly preferred aspect the antibody is selected from antibodies MX35, L2(20/3), L3(28/1) or active fragments thereof, or chimeric, veneered or humanized antibodies and single chain antibodies based thereon. In a particular aspect the antibody of the present invention comprises the heavy chain variable region and light chain variable region amino acid sequences of the MX35 antibody depicted in FIG. 5 and FIG. 6 respectively. In a further aspect an antibody derived from MX35 comprises the variable region CDR domains of the heavy and/or light chain as depicted in FIGS. 5 and 6. In one such aspect, an antibody of the present invention comprises a heavy and light chain, wherein the heavy chain variable region comprises the CDR region sequences SEQ ID NO: 26, 27 and 28, and the light chain variable region comprises the CDR region sequences SEQ ID NO: 31, 32 and 33.

The invention provides various antibodies directed against SLC34A2 and capable of binding or recognizing SLC34A2, particularly amino acids 312-340, particularly the SLC34A2 peptide and SEQ ID NO: 8. The MX35 variable region sequence comprising CDR regions SEQ ID NO: 26-28, for the heavy chain, and SEQ ID NO: 31-32, served as the basis for generating additionally antibodies. Veneered MX 35 is provided herein, an exemplary such veneered antibody comprising the heavy chain variable region sequence SEQ ID NO:38 and the light chain variable region sequence SEQ ID NO: 39. Chimeric MX 35 is provided herein, an exemplary such chimeric antibody comprising the heavy chain variable region sequence SEQ ID NO:40 and the light chain variable region sequence SEQ ID NO: 41. Single chain antibodies have been generated based on the veneered and chimeric MX35 antibodies and are provided herein. ScFv antibody based on veneered MX35 is set out in FIG. 16 and has the amino acid sequence of SEQ ID NO: 42 and the nucleic acid sequence of SEQ ID NO:43. ScFv antibody based on chimeric MX35 is set out in FIG. 17 and has the amino acid sequence of SEQ ID NO: 44 and the nucleic acid sequence of SEQ ID NO:45. Humanized MX35 antibody is another aspect of the invention and is provided herein. The exemplary humanized MX35 antibody comprises a light chain variable region sequence of SEQ ID NO: 35 and a heavy chain variable region sequence of SEQ ID NO: 37 and is depicted in FIGS. 11A and 11B. The heavy chain variable region of humanized MX35 comprises the CDR regions as set out in SEQ ID NO: 26, 27 and 28. The light chain variable region of humanized MX35 comprises the CDR regions as set out in SEQ ID NO: 31, 32 and 33.

Thus, the invention provides membrane transporter epitopes, particularly the epitope encompassed in amino acids 312-340 of SLC34A2, which can be utilized in generating antibodies which have anti-tumor capacity and activity or use in stimulating an immunological response which is an anti-tumor response. The invention provides membrane transporter epitopes, particularly SLC34A2 epitopes, most the epitope encompassed in amino acids 312-340 of SLC34A2, which can be utilized in generating antibodies which have anti-tumor capacity and activity or use in stimulating an immunological response which is an anti-tumor response. In a general aspect the invention provides an SLC34A2 epitope, particularly the epitope amino acids 312-340 of SLC34A2, which is found in tumorigenic cells, particularly ovarian cancer cells.

In accordance with the present invention, SLC34A2 peptides, particularly peptides comprising amino acids 312-340 of SLC34A2, are provided which are capable of generating antibodies, particularly monoclonal antibodies, which recognize tumor or cancer cells and have anti-tumor and anti-cancer activity.

The SLC34A2 peptides, particularly peptides comprising amino acids 312-340 of SLC34A2, of the present invention provide diagnostic and therapeutic uses to identify, characterize and target a number of tumor types, for example, ovarian, thyroid, breast, lung, and kidney, particularly ovarian cancer.

In its broadest aspect, the present invention encompasses isolated polypeptides comprising an amino acid sequence of an SLC34A2 peptide, particularly amino acids 312-340 of SLC34A2. The isolated peptides, including combinations of one or more thereof, are suitable for use in generating antibodies which recognize SLC34A2 and have anti-tumor activity and in immunizing animals, particularly mammals, most particularly humans, who have cancer or tumor disease.

The present invention is directed to an isolated receptor polypeptide which comprises the amino acid sequence set out in any of SEQ ID NOS: 1-8 and immunogenic fragments thereof.

The invention provides an isolated peptide having the amino acid sequence INVTVPSTANCTSPSLCWTDGIQNWTMKN (SEQ ID NO: 1).

The invention provides an isolated peptide having the amino acid sequence INVTVPSTANATSPSLCWTDGIQNWTMKN (SEQ ID NO: 2).

The invention provides an isolated peptide having the amino acid sequence INVTVPSTANCTSPSLAWTDGIQNWTMKN (SEQ ID NO: 3).

The invention provides an isolated peptide having the amino acid sequence INVTVPSTANATSPSLAWTDGIQNWTMKN (SEQ ID NO: 4).

The invention provides an isolated peptide having the amino acid sequence PSTANCTSPSLCWTDGIQNWTMKN (SEQ ID NO: 5).

The invention provides an isolated peptide having the amino acid sequence ANCTSPSLCWTDGIQNWTMKN (SEQ ID NO: 6).

The invention provides an isolated peptide having the amino acid sequence TSPSLCWTDGIQNWTMKN (SEQ ID NO: 7).

The invention provides an isolated peptide having the amino acid sequence SPSLCWTDGIQNWTM (SEQ ID NO: 8).

The present invention extends to an immunogenic receptor peptide, particularly selected from any of SEQ ID NOS: 1-8, or an immunogenic fragment thereof. The present invention also extends to immunogenic receptor peptides wherein such polypeptides comprise a combination of at least one immunogenic receptor peptide, selected from any of SEQ ID NOS: 1-8, or immunogenic peptide fragment thereof.

The invention provides a method for immunizing a mammal comprising administering an SLC34A2 epitope peptide or an immunogenic fragment thereof, whereby antibodies which are immunoreactive with the epitope peptide exposed on cells expressing abnormal or overexpressed growth factor receptor, but not exposed on wild type cells, are produced. The invention further provides a method for immunizing a mammal comprising administering an SLC34A2 peptide selected from any of SEQ ID NOS: 1-8 or an immunogenic fragment thereof, whereby antibodies which are immunoreactive with cancer cells, particularly ovarian cancer cells, are produced. The invention provides a method for immunizing a mammal comprising administering an SLC34A2 peptide selected from any of SEQ ID NOS: 1-8 or an immunogenic fragment thereof, whereby antibodies which are immunoreactive with SLC34A2 extracellular domain and SLC34A2 on cells are produced.

In a further aspect, the present invention extends to vaccines and immunogenic compositions based on the receptor peptides described herein. The present invention provides a vaccine comprising one or more SLC34A2 peptide, particularly amino acids 312-340 of SLC34A2, including selected from any of SEQ ID NOS: 1-8, and a pharmaceutically acceptable adjuvant. The present invention provides a vaccine comprising one or more peptides selected from any of SEQ ID NOS: 1-8, and a pharmaceutically acceptable adjuvant. The present invention provides an immogenic composition comprising one or more SLC34A2 peptide selected from any of SEQ ID NOS: 1-8, and a pharmaceutically acceptable adjuvant. The present invention provides an immunogenic composition comprising one or more peptides selected from any of SEQ ID NOS: 1-8, and a pharmaceutically acceptable adjuvant.

The present invention further provides an anti-tumor or anti-cancer vaccine comprising one or more SLC34A2 peptides selected from the group of any of SEQ ID NOS: 1-8, further comprising one or more additional tumor antigens. The present invention further provides a tumor or anti-cancer vaccine comprising one or more SLC34A2 peptides, particularly a peptide corresponding to amino acids 312-340 of SLC34A2 or fragments thereof, particularly selected from the group of any of SEQ ID NOS: 1-8. The composition may further comprise one or more additional SLC34A2 or other tumor antigens.

In another aspect, the invention is directed to a vaccine for treatment of a mammal, particularly a human, subject suffering from ovarian cancer, thyroid cancer, lung cancer, breast cancer, kidney cancer, particularly ovarian cancer, including comprising an immunogenic amount of one or more SLC34A2 peptides, particularly comprising amino acids 312-340 of SLC34A2 selected from the group of any of SEQ ID NOS: 1-8 or immunogenic fragment thereof. Such a vaccine may contain the peptide and a pharmaceutically acceptable adjuvant. Such a vaccine may further contain the peptide conjugated to a carrier.

In another aspect, the invention is directed to a vaccine for treatment of a mammal, particularly a human, subject suffering from ovarian cancer, particularly epithelial ovarian cancer, particularly papillary serous carcinomas and low-grade endometrial tumors, including comprising an immunogenic amount of one or more SLC34A2 peptides, particularly comprising amino acids 312-340 of SLC34A2 selected from the group of any of SEQ ID NOS: 1-8 or immunogenic fragment thereof. Such a vaccine may contain the peptide and a pharmaceutically acceptable adjuvant. Such a vaccine may further contain the peptide conjugated to a carrier.

The invention provides pharmaceutical compositions comprising an SLC34A2 peptide, particularly amino acid 312-340 peptides, and a pharmaceutically acceptable carrier. The invention provides pharmaceutical compositions comprising an SLC34A2 peptide selected from one or more of peptides selected from any of SEQ ID NOS: 1-8, and a pharmaceutically acceptable carrier. The invention provides pharmaceutical compositions comprising an SLC34A2 peptide antibody and a pharmaceutically acceptable carrier. The invention provides pharmaceutical compositions comprising an SLC34A2 peptide antibody immunoreactive with one or more of peptides selected from any of SEQ ID NOS: 1-8, and a pharmaceutically acceptable carrier. The invention further provides a pharmaceutical composition comprising a combination of at least two antibodies to SLC34A2 peptide selected from any of SEQ ID NOS: 1-8 and a pharmaceutically acceptable carrier.

In a still further aspect, the present invention provides a purified antibody to an SLC34A2 peptide selected from any of SEQ ID NOS: 1-8.

Antibodies against the isolated polypeptides of the present invention include naturally raised and recombinantly prepared antibodies or fragments thereof, including single chain variants and Fv. These may include both polyclonal and monoclonal antibodies prepared by known genetic techniques, as well as bi-specific antibodies, and antibodies including other functionalities suiting them for diagnostic or therapeutic use. The antibodies include chimereic antibodies, veneered antibodies, humanized antibodies, domain antibodies, calemized antibodies and single chain antibodies. Such antibodies can be used in immunoassays to characterize tumors or diagnose cancer including, but not limited to ovarian cancer, thyroid cancer, lung cancer, breast cancer, kidney cancer, particularly ovarian cancer. The antibodies can also be used for passive immunization to reduce tumors or treat cancer including, but not limited to, ovarian cancer, thyroid cancer, lung cancer, breast cancer, kidney cancer, particularly ovarian cancer.

An antibody to an SLC34A2 peptide selected from any of SEQ ID NOS: 1-8 labeled with a detectable label is further provided. In particular embodiments, the label may selected from the group consisting of an enzyme, a chemical which fluoresces, and a radioactive element. In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{86}Y$, $^{90}Y$, $^{124}I$, $^{125}I$, $^{131}I$, $^{111}I$, $^{99}Tc$ and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

In a further embodiment, the present invention relates to certain therapeutic methods which would be based upon the activity of an antibody, or active fragments thereof, to an SLC34A2 peptide selected from any of SEQ ID NOS: 1-8, or upon agents or other drugs determined to modulate SLC34A2 by binding to or interacting with the SLC34A2 peptide. A first therapeutic method is associated with the prevention or treatment of cancer, including but not limited to ovarian cancer, thyroid cancer, lung cancer, breast cancer, kidney cancer, particularly ovarian cancer.

In particular, the antibodies of the present invention, or active fragments thereof, and chimeric or synthetic antibodies derived therefrom can be prepared in pharmaceutical compositions, including a suitable vehicle, carrier or diluent, for administration in instances wherein therapy is appropriate, such as to treat cancer. Such pharmaceutical compositions may also include methods of modulating the half-life of the binding members, antibodies or fragments by methods known in the art such as pegylation. Such pharmaceutical compositions may further comprise additional antibodies or therapeutic agents.

The present invention also includes antibodies to an SLC34A2 peptide selected from any of SEQ ID NOS: 1-8, and any fragments thereof, which are covalently attached to or otherwise associated with other molecules or agents to be used for therapeutic or diagnostic purposes. These other molecules or agents include, but are not limited to, molecules (including other antibodies or antibody fragments) with distinct characteristics, toxins, ligands, radioactive isotopes and chemotherapeutic agents. Within the art there are many well-known molecules or agents which have been covalently linked or otherwise associated to antibodies to be used for therapeutic purposes. Examples of such molecules or agents include, but are not limited to: toxins such as calicheamicin, maytansinoid, duocarmycin, ricin, diphtheria toxin and pseudomonas exotoxin; ligands such as tumor necrosis factor (TNF); radioactive isotopes such as $^{90}Y$, $^{125}I$, $^{131}I$, $^{211}At$, $^{225}Ac$, $^{213}Bi$ and other $\alpha$, $\beta$ or $\gamma$ emitting isotope; and chemotherapeutic drugs as paclitaxel (Taxol®) and doxorubicin (Adriamycin®).

The present invention contemplates the use of the receptor peptides and antibodies thereto of the present invention in diagnostic tests and methods for determining and/or monitoring tumors and cancer including ovarian cancer, thyroid cancer, lung cancer, breast cancer, kidney cancer, particularly ovarian cancer.

The present invention relates to nucleic acid vaccines or DNA vaccines comprising nucleic acids encoding immunogenic SLC34A2 peptides, particularly selected from any of SEQ ID NOS: 1-8.

The present invention relates to nucleic acid vaccines or DNA vaccines comprising nucleic acids encoding one or more immunogenic an SLC34A2 peptide selected from any of SEQ ID NOS: 1-8 with at least one other polypeptide, particularly a tumor antigen or immunomodulatory molecule peptide.

The present invention includes methods for determining and monitoring tumors and cancer including ovarian cancer, thyroid cancer, lung cancer, breast cancer, kidney cancer, particularly ovarian cancer by detecting the presence or exposure of an SLC34A2 peptide selected from the group of any of SEQ ID NOS: 1-8. In a particular such method, the SLC34A2 peptide is measured by:

a. contacting a sample in which the presence or exposure of an SLC34A2 peptide selected from the group of any of SEQ ID NOS: 1-8 is suspected with an antibody to the said SLC34A2 peptide under conditions that allow binding of the peptide to the antibody to occur; and
b. detecting whether binding has occurred between the SLC34A2 peptide from the sample and the antibody;

wherein the detection of binding indicates the presence or exposure of the SLC34A2 peptide in the sample.

This method may include contacting the sample with an antibody selected from MX35 antibody, an antibody having a heavy and light chain wherein the heavy chain variable region comprises CDRs of SEQ ID NO: 26, 27 and 28 and the light chain variable region comprises CDRs of SEQ ID NO: 31, 32 and 33, humanized MX35 antibody comprising a heavy chain variable region of SEQ ID NO: 37 and a light chain variable region of SEQ ID NO: 35, veneered MX35 antibody comprising a heavy chain variable region of SEQ ID NO: 38 and a light chain variable region of SEQ ID NO: 39, chimeric MX35 antibody comprising a heavy chain variable region of SEQ ID NO: 40 and a light chain variable region of SEQ ID NO: 41, single chain Fv antibody having the sequence of SEQ ID NO: 42 or SEQ ID NO: 44.

The invention includes an assay system for screening of potential compounds effective to modulate the SLC34A2 by binding, interacting with or otherwise modulating SLC34A2 peptide of the present invention. In one instance, the test compound, or an extract containing the compound, could be administered to a cellular sample expressing the particular SLC34A2 peptide to determine the compound's effect upon SLC34A2 or, the SLC34A2 peptide of the present invention or the activity of SLC34A2 by comparison with a control.

It is still a further object of the present invention to provide a method for the treatment of mammals suffering from tumors or cancer including ovarian cancer, thyroid cancer, lung cancer, breast cancer, kidney cancer, particularly ovarian cancer. The invention provides a method for the treatment of mammals suffering from tumors or cancer including ovarian cancer, thyroid cancer, lung cancer, breast cancer, kidney cancer, particularly ovarian cancer comprising administering an immunogenically effective dose of a vaccine comprising an SLC34A2 peptide selected from the group of any of SEQ ID NOS: 1-8 to a subject.

In a further aspect the invention provides a method of treatment or diagnosis of ovarian cancer, particularly of papillary serous and endometrioid ovarian tumors. The invention provides a method for the treatment of mammals suffering from papillary serous and endometrioid ovarian tumors comprising administering an immunogenically effective dose of a vaccine comprising an SLC34A2 peptide selected from the group of any of SEQ ID NOS: 1-8 to a subject. The invention provides a method for the treatment of mammals suffering from papillary serous and endometrioid ovarian tumors comprising administering an SLC34A2 antibody selected from MX35 antibody, an antibody having a heavy and light chain wherein the heavy chain variable region comprises CDRs of SEQ ID NO: 26, 27 and 28 and the light chain variable region comprises CDRs of SEQ ID NO: 31, 32 and 33, humanized MX35 antibody comprising a heavy chain variable region of SEQ ID NO: 37 and a light chain variable region of SEQ ID NO: 35, veneered MX35 antibody comprising a heavy chain variable region of SEQ ID NO: 38 and a light chain variable region of SEQ ID NO: 39, chimeric MX35 antibody comprising a heavy chain variable region of SEQ ID NO: 40 and a light chain variable region of SEQ ID NO: 41, single chain Fv antibody having the sequence of SEQ ID NO: 42 or SEQ ID NO: 44.

In a further aspect, the invention provides a method of inducing an immune response in a subject which has tumors or cancer including ovarian cancer, thyroid cancer, lung cancer, breast cancer, kidney cancer, particularly ovarian cancer comprising administering to the subject an amount of the pharmaceutical composition comprising an SLC34A2 peptide selected from the group of any of SEQ ID NOS: 1-8, and a pharmaceutically acceptable carrier, thereby inducing an immune response.

It is an additional object of the present invention to provide a method for the treatment of mammals suffering from tumors or cancer including ovarian cancer, thyroid cancer, lung cancer, breast cancer, kidney cancer, particularly ovarian cancer. The invention provides a method for the treatment of mammals suffering from tumors or cancer including ovarian cancer, thyroid cancer, lung cancer, breast cancer, kidney cancer, particularly ovarian cancer, particularly epithelial ovarian cancer, comprising administering to said mammal a therapeutically effective amount of an SLC34A2 antibody selected from MX35 antibody, an antibody having a heavy and light chain wherein the heavy chain variable region comprises CDRs of SEQ ID NO: 26, 27 and 28 and the light chain variable region comprises CDRs of SEQ ID NO: 31, 32 and 33, humanized MX35 antibody comprising a heavy chain variable region of SEQ ID NO: 37 and a light chain variable region of SEQ ID NO: 35, veneered MX35 antibody comprising a heavy chain variable region of SEQ ID NO: 38 and a light chain variable region of SEQ ID NO: 39, chimeric MX35 antibody comprising a heavy chain variable region of SEQ ID NO: 40 and a light chain variable region of SEQ ID NO: 41, and single chain Fv antibody having the sequence of SEQ ID NO: 42 or SEQ ID NO: 44.

The invention provides a method for the treatment of mammals suffering from tumors or cancer including ovarian cancer, thyroid cancer, lung cancer, breast cancer, kidney cancer, particularly ovarian cancer, particularly epithelial ovarian cancer, comprising administering to said mammal a therapeutically effective amount of an SLC34A2 antibody selected from an antibody having a heavy and light chain wherein the heavy chain variable region comprises CDRs of SEQ ID NO: 26, 27 and 28 and the light chain variable region comprises CDRs of SEQ ID NO: 31, 32 and 33, humanized MX35 antibody comprising a heavy chain variable region of SEQ ID NO: 37 and a light chain variable region of SEQ ID NO: 35, veneered MX35 antibody comprising a heavy chain variable region of SEQ ID NO: 38 and a light chain variable region of SEQ ID NO: 39, chimeric MX35 antibody comprising a heavy chain variable region of SEQ ID NO: 40 and a light chain variable region of SEQ ID NO: 41, and single chain Fv antibody having the sequence of SEQ ID NO: 42 or SEQ ID NO: 44.

The invention provides a method for inhibiting phosphate transport in cells of a mammal comprising administering to said patient an effective amount of an SLC34A2 antibody. In a particular aspect the antibody is selected from an antibody having a heavy and light chain wherein the heavy chain variable region comprises CDRs of SEQ ID NO: 26, 27 and 28 and the light chain variable region comprises CDRs of SEQ ID NO: 31, 32 and 33, humanized MX35 antibody comprising a heavy chain variable region of SEQ ID NO: 37 and a light chain variable region of SEQ ID NO: 35, veneered MX35 antibody comprising a heavy chain variable region of SEQ ID NO: 38 and a light chain variable region of SEQ ID NO: 39, chimeric MX35 antibody comprising a heavy chain variable region of SEQ ID NO: 40 and a light chain variable region of SEQ ID NO: 41, and single chain Fv antibody having the sequence of SEQ ID NO: 42 or SEQ ID NO: 44. In an aspect of the method phosphate transport is inhibited in cells including ovarian cells, kidney cells, lung cells, thyroid cells, breast cells, particularly ovarian cells, particularly ovarian epithelial cells.

The binding of an antibody to its target antigen is mediated through the variable region, particularly the complementarity-determining regions (CDRs) of its heavy and light chains. Accordingly, specific binding members based on the variable region, particularly the CDR regions of the heavy or light chain, and preferably both, of mAb MX35 will be useful antibodies members for in vivo therapy. The variable region and CDRs of the mAb MX35 antibody are shown in FIGS. 5 and 6. The heavy chain CDRs correspond to SEQ ID NOS: 26-28 and the light chain CDRs correspond to SEQ ID NOS: 31-33.

In further aspects, the invention provides an isolated nucleic acid which comprises a sequence encoding an antibody or fragment thereof as defined above, and methods of preparing antibodies of the invention which comprise expressing said nucleic acids under conditions to bring about expression of said antibody, and recovering the antibody.

Other objects and advantages will become apparent to those skilled in the art from a review of the ensuing detailed description, which proceeds with reference to the following illustrative drawings, and the attendant claims.

BRIEF DESCRIPTION OF THE DRAWINGS

FIG. 5 depicts the nucleotide and amino acid sequence of the MX35 antibody heavy chain variable region, including the CDR domains CDR1, CDR2, and CDR3.

FIG. 6 depicts the nucleotide and amino acid sequence of the MX35 antibody light chain variable region, including the CDR domains CDR1, CDR2, and CDR3.

FIG. 7 depicts SDS-PAGE analysis of bacterially expressed and affinity purified GST/NaPi2b fusion proteins. (A) Expression analysis and purification of GST/NaPi2b-L from insoluble fraction of bacterial cell lysate. Expression of GST/NaPi2b-L in BL21(DE3) cells was induced by IPTG for 3 hours at 27° C. The pellet of bacterial cells was lysed and centrifuged to remove the insoluble fraction. Purification of GST/NaPi2b-L from the insoluble fraction was carried out by electro-elution from the SDS-PAGE gel. (B), (C). Expression profiles and the quality of affinity purified GST/NaPi2b-1L (188-300aa) (B) and GST/NaPi2b-2L (291-361aa) (C) analyzed by SDS-PAGE electrophoresis. The expression of GST/NaPi2b-1L and GST/NaPi2b-2L was induced by IPTG for 1, 2 and 3 hours. Harvested cells were lysed and centrifuged at 13,000 rpm to remove the insoluble fraction. The extract of soluble proteins was used for purification by affinity chromatography on Glutathione Sepharose.

FIG. 10 shows epitope mapping for anti-NaPi2b monoclonal antibodies.
(A) Schematic representation of GST/NaPi2b fusion proteins used in this study. The region of NaPi2b which possesses the epitopes for generated antibodies is marked and shown by amino acid sequence.
(B) Western-blot analysis of GST alone and GST/NaPi2b fusion proteins with L2(20/3) and anti-GST monoclonal antibodies. Equal amounts of GST alone or various GST/NaPi2b fusion proteins (2 μg each) were resolved by SDS-PAGE, electro blotted to PVDF membrane and probed with L2(20/3) and anti-GST monoclonal antibodies.

FIG. 11 shows a sequence alignment of heavy chain (A) and light chain (B) variable regions amino acid sequences of the murine and humanized versions of MX35 antibody. CDR regions are boxed.

FIG. 16 depicts the nucleic acid sequence (SEQ ID NO: 43) amino acid sequence (SEQ ID NO: 42) of single chain FV antibody based on the veneered MX35 (VMX35 ScFv #6). The signal sequence is depicted first in black; the variable heavy chain is next in green; the linker region in red follows; the variable light chain is next depicted in blue; and last sequences are the E-tag, shown in red.

FIG. 17 depicts the nucleic acid sequence (SEQ ID NO: 45) and amino acid sequence (SEQ ID NO: 44) of single chain Fv antibody based on the chimeric MX35 (chMX35 ScFv #8). The first sequence section shown in black is the signal sequence; followed by the variable heavy chain sequence in green; the linker region in red is next; the variable light chain follows in blue; and the last sequence in red is the E-tag.

DETAILED DESCRIPTION

Figure 1A:
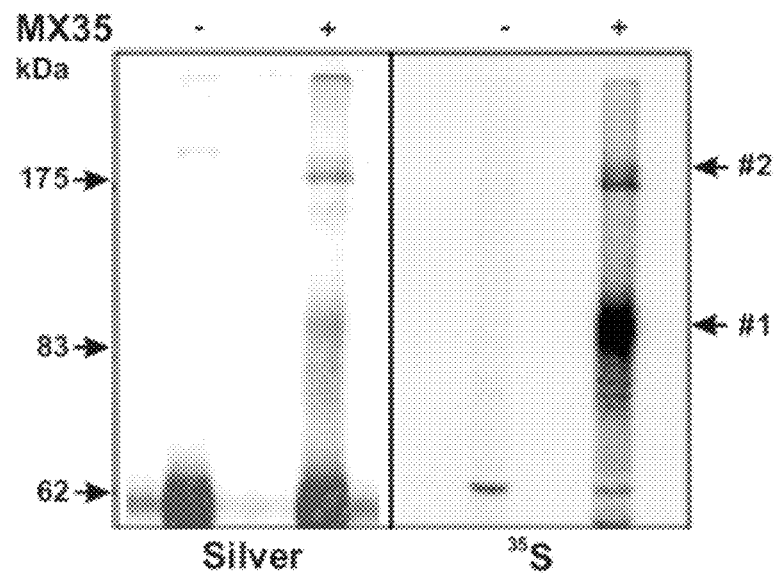
FIG. 1: Cell surface expressed MX35 antigen was isolated from two different MX35 antigen-positive cell lines, OVCAR-3 and SK-RC-18 by immunoprecipitation following metabolic labeling of proteins with $^{35}S$ methionine and $^{35}S$ cysteine. (A) SDS-PAGE of MX35 immune complexes labeled with $^{35}S$ and visualized by autoradiofluorography or by silver staining. MAb MX35 precipitated the antigen in two forms, band #1 and #2, differing in size; (B) peptide mass fingerprinting of trypsin digested Lys-tagged and sulfonated protein; (C) Sequence of the sodium-dependent phosphate transporter 2b protein. Peptides detected by mass spectrometry are shown in bold. The putative disulfide-bonded loop (aa 303-350) is also shown. The region containing the epitope recognized by mAb MX35 is shown in italics. Asparagine (N) residues that are probable N-linked glycosylation sites are shown in caps.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "membrane transporter peptides", "NaPi2B peptides", "SLC34A2 peptides", SLC34A2 epitope peptides" and any variants not specifically listed, may be used herein interchangeably, and as used throughout the present application and claims refer to peptide material including single or multiple peptides, and extends to those peptides comprising extracellular region of SLC34A2, including amino acids 312-340, and having the profile of activities and characteristics set forth herein and in the claims. Particularly peptides having the amino acid sequence data described herein and presented in any of SEQ ID NOS: 1-8, and variants thereof, are encompassed. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Methods for generating and testing modifications of the receptor epitope peptides, including variants thereof, including but not limited to, by site-directed mutagenesis or random mutagenesis are well known to those skilled in the art, and include those described and exemplified herein. Also, the terms "membrane transporter peptides", "NaPi2B peptides", "SLC34A2 peptides", SLC34A2 epitope peptides" are intended to include within their scope proteins and peptides specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding the SLC34A2 peptides and/or the SLC34A2 peptide-specific antibodies of the present invention. Nucleic acids encoding the SLC34A2 peptide code for a polypeptide comprising amino acid sequence or any of SEQ ID NOS: 1-8, and may be degenerate to one another.

Nucleic acids encoding the specific antibodies directed against SLC34A2 are also included in the invention. Such nucleic acids include those encoding antibodies selected from MX35, L2(20/3) and L3(28/1) or active fragments thereof. Nucleic acids, including DNA sequences, encoding MX35 antibody heavy and light chain polypeptides as set out in FIG. 5 (SEQ ID NO: 24) and FIG. 6 (SEQ ID NO: 29) are provided by this invention. Such nucleic acids include those encoding the CDR regions (SEQ ID NOS: 26-28 and 31-33) of MX35 antibody. Nucleic acids encoding a humanized MX35 antibody are further provided herein including s set out in FIG. 11, the light chain variable region of humanized antibody is set out in SEQ ID NO: 34 and the heavy chain variable region of humanized antibody is set out in SEQ ID NO: 36. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |

| | |
|---|---|
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in DNA sequences encoding the antibodies or peptides provided herein, such as set out in FIGS. 5 and 6, the CDRs thereof SEQ ID NOS 26-28 and 31-33, or in peptides such as SEQ ID NOS: 1-8, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:
Amino Acids with Nonpolar R Groups
Alanine, Valine, Leucine, Isoleucine, Proline, Phenylalanine, Tryptophan, Methionine
Amino Acids with Uncharged Polar R Groups
Glycine, Serine, Threonine, Cysteine, Tyrosine, Asparagine, Glutamine
Amino Acids with Charged Polar R Groups (Negatively Charged at pH 6.0)
Aspartic acid, Glutamic acid
Basic Amino Acids (Positively Charged at pH 6.0)
Lysine, Arginine, Histidine (at pH 6.0)
Another grouping may be those amino acids with phenyl groups:
Phenylalanine, Tryptophan, Tyrosine
Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free NH$_2$ can be maintained.

Amino acid substitutions may also be introduced to substitute an amino acid with a particularly preferable property. For example, a Cys may be introduced a potential site for disulfide bridges with another Cys. A H is may be introduced as a particularly "catalytic" site (i.e., H is can act as an acid or base and is the most common amino acid in biochemical catalysis). Pro may be introduced because of its particularly planar structure, which induces—turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$, with washes of higher stringency, if desired.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Also included within the meaning of the term "antibody" are any "antibody fragment".

As antibodies can be modified in a number of ways, the term "antibody" should be construed as covering any specific molecule or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) multivalent antibody fragments (scFv dimers, trimers and/or tetramers (Power and Hudson, J. Immunol. Methods 242: 193-204 9 (2000))(ix) bispecific single chain Fv dimers (PCT/US92/09965) and (x) "diabodies", multivalent or multispecific fragments constructed by gene fusion (WO94/13804; P. Holliger et al Proc. Natl. Acad. Sci. USA 90 6444-6448, (1993)).

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change size or in in the S phase activity of a target cellular mass, or other feature of pathology such as for example antibody response, T cell or B cell response, reduction in EGFR expression.

The term "adjuvant" refers to a compound or mixture that enhances the immune response, particularly to an antigen. An adjuvant can serve as a tissue depot that slowly releases the antigen and also as a lymphoid system activator that non-specifically enhances the immune response (Hood et al., *Immunology, Second Ed.,* 1984, Benjamin/Cummings: Menlo Park, Calif., p. 384). Often, a primary challenge with an antigen alone, in the absence of an adjuvant, will fail to elicit a humoral or cellular immune response. Previously known and utilized adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebacterium parvum*. Mineral salt adjuvants include but are not limited to: aluminum hydroxide, aluminum phosphate, calcium phosphate, zinc hydroxide and calcium hydroxide. Preferably, the adjuvant composition further comprises a lipid of fat emulsion comprising about 10% (by weight) vegetable oil and about 1-2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight). Other examples of adjuvants include monophosphoryl lipid A (MPL, SmithKline Beecham), a congener obtained after purification and acid hydrolysis of *Salmonella* Minnesota Re 595 lipopolysaccharide; saponins including QS21 (SmithKline Beecham), a pure QA-21 saponin purified from *Quillja saponaria* extract; DQS21, described in PCT application WO96/33739 (SmithKline Beecham); ISCOM (CSL Ltd., Parkville, Victoria, Australia) derived from the bark of the *Quillaja saponaria* molina tree; QS-7, QS-17, QS-18, and QS-L1 (So et al., Mol. Cells. 7:178-186, 1997); montanide; alum; CpG oligonucleotides (see e.g. Kreig et al., Nature 374:546-9, 1995); various water-in-oil emulsions prepared from biodegradable oils such as squalene and/or tocopherol; and factors that are taken up by the so-called 'toll-like receptor 7' on certain immune cells that are found in the outside part of the skin, such as imiquimod (3M, St. Paul, Minn.). Particularly, the antigens may be administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 µg to about 100 µg. Other adjuvants are known in the art and can be used in the invention (see, e.g. Goding, Monoclonal Antibodies: Principles and Practice, 2nd Ed., 1986). Methods for the preparation of mixtures or emulsions of polypeptide and adjuvant are well known to those of skill in the art of inducing and/or enhancing an immune response and the art of vaccination.

As used herein, the term "immunomodulator" refers to an agent which is able to modulate an immune response or immunological response. Such modulation includes the enhancement of antibody production, of humoral response, of cellular immune response. Examples of immunomodulators include, but are not limited to, adjuvants, cytokines, interleukins, chemokines and growth factors.

The term "effective amount" of an immunomodulator refers to an amount of an immunomodulator sufficient to enhance a vaccine-induced immune response, be it cell-mediated, humoral or antibody-mediated. An effective amount of an immunomodulator, if injected, can be in the range of about 0.1-1,000 µg, preferably 1-900 µg, more preferably 5-500 µg, for a human subject, or in the range of about 0.01-10.0 µg/Kg body weight of the subject animal. This amount may vary to some degree depending on the mode of administration, but will be in the same general range. If more than one immunomodulator is used, each one may be present in these amounts or the total amount may fall within this range. An effective amount of an antigen may be an amount capable of eliciting a demonstrable immune response in the absence of an immunomodulator. The appropriate amount of antigen to be used is dependent on the specific antigen and is well known in the art.

The exact effective amount necessary will vary from subject to subject, depending on the species, age and general condition of the subject, the severity of the condition being treated, the mode of administration, etc. Thus, it is not possible to specify an exact effective amount. However, the appropriate effective amount may be determined by one of ordinary skill in the art using only routine experimentation or prior knowledge in the vaccine art.

An "immunological response" to a composition or vaccine comprised of an antigen is the development in the host of a cellular- and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

As used herein, "pg" means picogram, "ng" means nanogram, "ug" or "µg" mean microgram, "mg" means milligram, "ul" or "µl" mean microliter, "ml" means milliliter, "l" means liter.

The present invention relates to SLC34A2 peptides and epitopes, particularly peptides encompassing amino acids 312-340 of SLC34A2, which can be utilized in generating antibodies which have anti-tumor capacity and activity or stimulating an immunological response which is an anti-tumor response. The invention provides SLC34A2 peptides and epitopes, particularly peptides of amino acids 312-340 of SLC34A2, which can be utilized in screening for compound agents which have anti-tumor capacity and activity or use in stimulating an anti-tumor response.

SLC34A2 is a member of the solute carrier gene family and has been reported to mediate transport of inorganic phosphate into epithelial cells via sodium ion co-transport, thus having a potential role in phosphate homeostasis. SLC34A2 has also been termed sodium-dependent phosphate transport protein 2b (NaPi2b) and was isolated and cloned from a human small intestine and lung cDNA library (Field, J. A. et al (1999) Biocehm Biophys Res Commun 258:578-582; Xu, H. et al (1999) Genomics 62:281-284). The SLC34A2 gene codes for a protein of 690 amino acids, as set out in FIG. 1C, which is a membrane protein predicted to pass through the membrane multiple times, with 8 transmembrane domains. SLC34A2 also corresponds to and is termed sodium dependent phosphate transporter IPT-1, the human nucleic acid and polypeptide sequence of which are provided in Fields et al U.S. Pat. Nos. 6,319,688 and 6,350,858, each of which is incorporated herein by reference.

The SLC34A2 peptides, particularly of amino acids 312-340 of SLC34A2 peptides, of the present invention provide diagnostic and therapeutic uses to identify, characterize and target a number of tumor types, for example, ovarian cancer, thyroid cancer, lung cancer, breast cancer, kidney cancer, particularly ovarian cancer.

The present invention encompasses isolated polypeptides comprising an amino acid sequence of a SLC34A2 peptide having an amino acid sequence selected from any of SEQ ID NOS: 1-8. The present invention further encompasses variants or mutants of any of SEQ ID NOS: 1-8, wherein one or more amino acid is substituted, including by a conservative or non-conservative amino acid. Any such variant or mutant peptide which is capable of being recognized or bound by the mAb MX35 antibody, or a recombinant or synthetic antibody derived therefrom, or which is capable of generating antibody(ies) having a characteristic of mAb MX35 is encompassed by the present invention. In particular, any such peptide(s) may be capable of generating antibodies which recognize growth factor receptor and have anti-tumor activity. The isolated peptides, including combinations of one or more thereof, are suitable for use in generating antibodies which recognize SLC34A2 and have anti-tumor activity and in immunizing animals, particularly mammals, most particularly humans, who have cancer or tumor disease.

As stated above, the present invention also relates to a recombinant DNA molecule or cloned gene, or a degenerate variant thereof, which encodes SLC34A2 epitope, or an immunogenic fragment thereof, that has an amino acid sequence set forth in any of SEQ ID NOS: 1-8; preferably a nucleic acid molecule, in particular a recombinant DNA molecule or cloned gene, encoding SLC34A2 peptide selected from any of SEQ ID NOS: 1-8.

Antibodies

In a still further aspect, the present invention provides a purified antibody to an SLC34A2 peptide selected from any of SEQ ID NOS: 1-8. The invention further provides an antibody MX35 having the nucleic acid and amino acid variable region heavy and light chain sequence as set out in FIGS. 5 and 6. Antibody fragments, derivatives, or recombinant antibodies comprising the variable region sequence of FIGS. 5 and 6 are provided. Antibodies comprising the CDR domain sequences as set out in FIGS. 5 and 6 are provided. In one such aspect, an antibody of the present invention comprises a heavy and light chain, wherein the heavy chain variable region comprises the CDR region sequences SEQ ID NO: 26, 27 and 28, and the light chain variable region comprises the CDR region sequences SEQ ID NO: 31, 32 and 33.

The invention provides various antibodies directed against SLC34A2 and capable of binding or recognizing SLC34A2, particularly amino acids 312-340, particularly the SLC34A2 peptide and SEQ ID NO: 8. The MX35 variable region sequence comprising CDR regions SEQ ID NO: 26-28, for the heavy chain, and SEQ ID NO: 31-32, served as the basis for generating additional antibodies. Veneered MX 35 is provided herein, an exemplary such veneered antibody comprising the heavy chain variable region sequence SEQ ID NO:38 and the light chain variable region sequence SEQ ID NO: 39. Chimeric MX 35 is provided herein, an exemplary such chimeric antibody comprising the heavy chain variable region sequence SEQ ID NO:40 and the light chain variable region sequence SEQ ID NO: 41. Single chain antibodies have been generated based on the veneered and chimeric MX35 antibodies and are provided herein. ScFv antibody based on veneered MX35 is set out in FIG. 16 and has the amino acid sequence of SEQ ID NO: 42 and the nucleic acid sequence of SEQ ID NO:43. ScFv antibody based on chimeric MX35 is set out in FIG. 17 and has the amino acid sequence of SEQ ID NO: 44 and the nucleic acid sequence of SEQ ID NO:45. Humanized MX35 antibody is another aspect of the invention and is provided herein. The exemplary humanized MX35 antibody comprises a light chain variable region sequence of SEQ ID NO: 35 and a heavy chain variable region sequence of SEQ ID NO: 37 and is depicted in FIGS. 11A and 11B. The heavy chain variable region of humanized MX35 comprises the CDR regions as set out in SEQ ID NO: 26, 27 and 28. The light chain variable region of humanized MX35 comprises the CDR regions as set out in SEQ ID NO: 31, 32 and 33.

Antibodies against the isolated polypeptides of the present invention include naturally raised and recombinantly prepared antibodies. These may include both polyclonal and monoclonal antibodies prepared by known genetic techniques, as well as bi-specific antibodies, and antibodies including other functionalities suiting them for diagnostic use.

Such antibodies can be used therapeutically to treat patients with tumors expressing SLC34A2, including but not limited to ovarian cancer, thyroid cancer, lung cancer, breast cancer, kidney cancer, particularly ovarian cancer. Such antibodies can also be used immunoassays to characterize tumors or diagnose cancer including ovarian cancer, thyroid cancer, lung cancer, breast cancer, kidney cancer, particularly ovarian cancer. The antibodies can also be used for passive immunization to reduce tumors or treat cancer including from ovarian cancer, thyroid cancer, lung cancer, breast cancer, kidney cancer, particularly ovarian cancers.

Also, antibodies including both polyclonal and monoclonal antibodies, and drugs that modulate the exposure or activity of the SLC34A2 peptides and/or their subunits may possess certain diagnostic applications and may for example, be utilized for the purpose of detecting and/or measuring conditions such as viral infection or the like. For example, the receptor peptides or immunogenic fragments thereof may be used to produce both polyclonal and monoclonal antibodies in a variety of cellular media, by known techniques such as the hybridoma technique utilizing, for example, fused mouse spleen lymphocytes and myeloma cells. Likewise, small molecules that mimic or antagonize the activity(ies) of the receptor peptides or epitope sequences of the invention may be discovered or synthesized, and may be used in diagnostic and/or therapeutic protocols.

Panels of monoclonal antibodies produced against the receptor peptides can be screened for various properties; i.e., isotype, epitope, affinity, etc. Of particular interest are monoclonal antibodies that neutralize or modulate the activity of the receptor. Such monoclonals can be readily identified in receptor activity or signaling assays or in tumorigenicity assays. High affinity antibodies are also useful when immunoaffinity purification of mutant SLC34A2 is desired.

Particularly, the anti-SLC34A2 peptide antibody used in the diagnostic methods of this invention can be an affinity purified polyclonal antibody. More particularly, the antibody is a monoclonal antibody (mAb). In addition, the anti-receptor peptide antibody molecules used herein may be in the form of Fab, Fab', F(ab')$_2$ or F(v) portions of whole antibody molecules. Synthetic, humanized, recombinant or fully human antibodies are particularly preferred and provided.

Therapeutic uses of antibodies are well known within the art. There are several ways of using antibodies for therapeutic purposes, for example, as naked antibody in combination with know chemotherapeutic drugs, as radiolabelled antibodies for radioimmuntherapy, or as antibodies conjugated/ coupled with cytotoxic drugs, toxins, or other toxic agents.

Radiolabelled antibodies and fragments thereof, particularly radioimmunoconjugates, are useful in radioimmunotherapy, particularly as radiolabelled antibodies for cancer therapy. In a still further aspect, the radiolabelled s antibodies and fragments thereof, are useful in radioimmuno-guided surgery techniques, wherein they can identify and indicate the presence and/or location of cancer cells, precancerous cells, tumor cells, and hyperproliferative cells, prior to, during or following surgery to remove such cells.

Immunoconjugates or antibody fusion proteins of the present invention, wherein the antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

The antibodies, or antibody fragments, of the current invention may be administered alone or in combination with other treatments, therapeutics or agents, either simultaneously or sequentially dependent upon the condition to be treated. In addition, the present invention contemplates and includes compositions comprising the antibody or fragment thereof, herein described and other agents or therapeutics such as anti-cancer agents or therapeutics, hormones, anti-SLC34A2 agents or antibodies, or immune modulators. More generally these anti-cancer agents may be tyrosine kinase inhibitors or phosphorylation cascade inhibitors, post-translational modulators, cell growth or division inhibitors (e.g. anti-mitotics), or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. The composition can be administered in combination (either sequentially (i.e. before or after) or simultaneously) with tyrosine kinase inhibitors, phosphate transport inhibitors, doxorubicin, temozolomide, cisplatin, carboplatin, nitrosoureas, procarbazine, vincristine, hydroxyurea, 5-fluorouracil, cytosine arabinoside, cyclophosphamide, epipodophyllotoxin, carmustine, lomustine, and/or other chemotherapeutic agents. In addition, the composition may be administered with hormones such as dexamethasone, immune modulators, such as interleukins, tumor necrosis factor (TNF), granulocyte macrophage-colony stimulating factor (GM-CSF) or other growth factors or cytokines which stimulate the immune response and reduction or elimination of cancer cells or tumors.

Methods for producing polyclonal anti-receptor peptide antibodies are well-known in the art. See U.S. Pat. No. 4,493,795 to Nestor et al. A monoclonal antibody, typically containing Fab and/or $F(ab')_2$ portions of useful antibody molecules, can be prepared using the hybridoma technology described in Antibodies—A Laboratory Manual, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a receptor peptide or an immunogenic fragment thereof. Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present receptor peptides and their ability to inhibit specified receptor peptide or receptor activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques. Media useful for the preparation of these compositions are both well-known in the art and commercially available and include synthetic culture media, inbred mice and the like. An exemplary synthetic medium is Dulbecco's minimal essential medium (DMEM; Dulbecco et al., Virol. 8:396 (1959)) supplemented with 4.5 gm/l glucose, 20 mm glutamine, and 20% fetal calf serum. An exemplary inbred mouse strain is the Balb/c.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Apart from the traditional hybridoma technique there are a number of other well-known techniques for making monoclonal antibodies. Particularly useful are methods of making fully human antibodies. One method is phage display technology which can be used to select a range of human antibodies binding specifically to the antigen using methods of affinity enrichment. Phage display has been thoroughly described in the literature and the construction and screening of phage display libraries are well known in the art, see, e.g., Hoogenboom et al. Trends Biotechnol., 15:62-70 (1997); Hoogenboom, et al. Immunotechnology 4:1-20 (1998); McGregor et al. Mol. Biotechnol, 6:155-62 (1996); and Bird et al., Science, 242:423-426 (1988). Fully human antibodies can also be prepared by immunizing transgenic mice carrying large portions of the human immunoglobulin heavy and light chains, with an immunogen. Examples of such mice are well known within the art, e.g., the Xenomouse® (Abgenix, Inc.) and the HuMAb-Mouse (Medarex, Inc.,), see also U.S. Pat. No. 6,207,418, U.S. Pat. No. 6,150,584, U.S. Pat. No. 6,111,166, U.S. Pat. No. 6,075,181, U.S. Pat. No. 5,922,545, U.S. Pat. No. 5,545,806 and U.S. Pat. No. 5,569,825. Antibodies can then be prepared by standard techniques, e.g. standard hybridoma techniques or by phage display.

Monocolonal antibodies derived by hybridoma technique from another species than human, such as mouse, can be humanized, which means that a non-human antibody gentically engineered to be more human in order to avoid HAMA when infused into humans. The methods humanization of antibodies are well known within the art, among the more more common methods are complementarity-determining region (CDR) grafting and veneering (also known as resurfacing). These methods have been extensively described in the literature and in patents, see e.g.; King "Applications and Engineering of Monoclonal Antibodies" Taylor & Francis, 1998; U.S. Pat. Nos. 5,225,539; 5,530,101; 5,585,089, 5,859,205 and 6,797,492, each incorporated herein by reference.

Another possibility in developing molecules that bind/block/target or in some other way interact with the epitopes described herein, are by making peptides. These peptides could be any random peptide that have an affinity for the epitopes and they don't necessarily have to be of the immunoglobulin family. These peptides are often isolated by similar techniques as for phage display antibodies (Szardenings, J Recept Signal Transduct Res. 2003; 23(4):307-49). The use of peptides from such random peptide libraries are similar to antibodies and antibody fragments.

As described in detail above, antibody(ies) to the peptide can be produced and isolated by standard methods including the well known hybridoma techniques. For convenience, the antibody(ies) to the receptor peptide will be referred to herein as $Ab_1$ and antibody(ies) raised in another species as $Ab_2$. It will be seen from the below, that a characteristic property of $Ab_2$ is that it will react with $Ab_1$. For purposes of this description and claims, $Ab_1$ will be referred to as a primary or anti-receptor peptide antibody, and $Ab_2$ will be referred to as a secondary or anti-$Ab_1$ antibody.

The presence of exposed epitope peptide in cells can be ascertained by the usual immunological procedures applicable to such determinations. A number of useful procedures are known. Three such procedures which are especially useful utilize either the receptor peptide labeled with a detectable label, antibody $Ab_1$ labeled with a detectable label, or antibody $Ab_2$ labeled with a detectable label. The procedures may be summarized by the following equations wherein the asterisk indicates that the particle is labeled, and "~" stands for the receptor peptide:

A. $\sim{}^*+Ab_1=\sim{}^*Ab_1$
B. $\sim{}+Ab^*=\sim{}Ab_1^*$
C. $\sim{}+Ab_1+Ab_2^*=\sim{}Ab_1Ab_2^*$ The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance, the peptide forms complexes with one or more antibody(ies) or binding partners and one member of the complex is labeled with a detectable label. The fact that a complex has formed and, if desired, the amount thereof, can be determined by known methods applicable to the detection of labels. The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The SLC34A2 peptide or its binding partner(s) can also be labeled with a radioactive element or with an enzyme. The radioactive label can be detected by any of the currently available counting procedures. The preferred isotope may be selected from $^{3}$H, $^{14}$C, $^{32}$P, $^{35}$S, $^{36}$Cl, $^{51}$Cr, $^{57}$CO, $^{58}$Co, $^{59}$Fe, $^{90}$Y, $^{125}$I, $^{131}$I, and $^{186}$Re.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

In a further embodiment of this invention, kits or assays may be prepared to determine the presence or absence of or the modulation of SLC34A2 peptide in target cells. In accordance with the testing techniques discussed above. One class of such kits or assays will contain at least the labeled SLC34A2 peptide or its binding partner, for instance an antibody specific thereto, and directions, of course, depending upon the method selected, e.g., "competitive," "sandwich," "DASP" and the like. The kits or assays may also contain peripheral reagents such as buffers, stabilizers, etc.

Accordingly, a kit may be prepared for the demonstration of the presence or activity of SLC34A2, comprising:

(a) a predetermined amount of at least one labeled immunochemically reactive component obtained by the direct or indirect attachment of the SLC34A2 peptide or a specific binding partner thereto, to a detectable label;

(b) other reagents; and (c) directions for use of said kit.

More specifically, the kit may comprise:

(a) a known amount of the SLC34A2 peptide as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

An assay system for screening potential drugs effective to modulate the activity of the SLC34A2 peptide, or an antibody thereto may be prepared. The SLC34A2 peptide or antibody may be introduced into a test system, and the prospective drug may also be introduced into the resulting cell culture, and the culture thereafter examined to observe any changes in the SLC34A2 activity of the cells, due either to the addition of the prospective drug alone, or due to the effect of added quantities of the known SLC34A2 peptide, or an antibody thereto.

Compositions

The present invention further contemplates therapeutic compositions useful in practicing the therapeutic methods of this invention. A subject therapeutic composition includes, in admixture, a pharmaceutically acceptable excipient (carrier) and one or more of a SLC34A2 peptide, particularly selected from a peptide having a sequence of any of SEQ ID NOS: 1-8, or immunogenic fragment thereof, as described herein as an active ingredient. The invention further contemplates therapeutic compostions of the SLC34A2 antibody, including recombinant antibodies or antibody fragment, variant antibodies, chimeric antibodies comprising MX35 antibody variable region sequences, as set out in FIGS. 5 and 6, or the CDRS thereof.

The preparation of therapeutic compositions which contain polypeptides, antibodies, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, antibody, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic peptide, antibody or immunogenic fragment-containing compositions may be administered orally, intramuscularly, intraperitoneally or intravenously, as by injection or administration of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle. The therapeutic receptor peptide or immunogenic fragment-containing compositions may be administered multiply in series, as in an immunization schedule.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of growth factor receptor binding and signaling capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the SLC34A2 peptide, or antibody thereto, and one or more of the following active ingredients: an anti-mitotic, a chemotherapeutic agent, an immunomodulator.

Nucleic Acids

Another feature of this invention is the expression of DNA sequences encoding the peptides or antibodies disclosed herein. As is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast, α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that peptide analogs, antibody analogs, variants or derivatives, including ction fragments, may be prepared from nucleotide sequences of the protein complex/subunit derived within the scope of the present invention. Analogs, such as fragments, may be produced, for example, by proteolytic digestion, including pepsin digestion, of the peptides or antibodies. Other analogs, such as muteins, can be produced by standard site-directed mutagenesis of peptide or antibody coding sequences. Analogs exhibiting "SLC34A2 peptide activity" or "SLC34A2 antibody activity" such as small molecules, whether functioning as promoters or inhibitors, may be identified by known in vivo and/or in vitro assays.

As mentioned above, a DNA sequence encoding the peptide(s) or antibody(ies) can be prepared synthetically rather than cloned. The DNA sequence can be designed with the appropriate codons for the receptor peptide amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984).

Synthetic DNA sequences allow convenient construction of genes which will express receptor peptide analogs or "muteins". Alternatively, DNA encoding muteins can be made by site-directed mutagenesis of native growth factor receptor genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science,* 244:182-188 (April 1989). This method may be used to create analogs with unnatural amino acids.

Antigens and Vaccines

The characterization of tumour antigens recognised by T cells has revolutionized the cancer-vaccine approach, providing for the first time the opportunity to immunise patients against cancer by using well-defined antigens.

Synthetic antigens, including vaccines, may be prepared by chemically synthesizing the SLC34A2 peptides of the present invention, optionally including other tumor antigens. These peptides, peptide carrier combinations, lipid derivatives of such peptides as well as tumor antigens, may be used either individually or combined as a cocktail, and formulated with an adjuvant to provide an immunogenic composition. As contemplated herein, an antigen may be covalently bonded to a glycolipid analog to provide a discrete molecule which exhibits an enhanced adjuvanting effect on the antigen which is greater than the adjuvanting effect attainable in the absence of such covalent bonding. These compositions can be used to immunize mammals, for example, by the intramuscular or parenteral routes, or by delivery to mucosal surfaces using microparticles, capsules, liposomes and targeting molecules, such as toxins and antibodies.

Vaccines containing peptides are generally well known in the art, as exemplified by U.S. Pat. Nos. 4,601,903; 4,599,231; 4,599,230; and 4,596,792; all of which references are incorporated herein by reference. The use of peptides in vivo may first require their chemical modification since the peptides themselves may not have a sufficiently long serum and/or tissue half-life and/or sufficient immunogenicity. In addition, it may be advantageous to modify the peptides in order to impose a conformational restraint upon them. This might be useful, for example, to mimic a naturally-occurring conformation of the peptide in the context of the native protein in order to optimize the effector immune responses that are elicited.

This invention provides an immunogenic composition comprising an amount of the SLC34A2 peptide, or immunogenic fragments thereof and combinations thereof. In one embodiment the SLC34A2 peptide is selected from SEQ ID NOS: 1-8.

This invention provides a method of stimulating or enhancing an antigen-specific cell-mediated immune response which comprises administering to a subject an amount of a receptor peptide, or immunogenic fragment thereof, and a suitable adjuvant.

This invention provides a method of treating a subject with a tumor or cancer comprising administering to a subject an amount of the SLC34A2 peptide and adjuvant composition of the present invention as an immunomodulator, and a suitable carrier or diluent. In particular, a subject having cancer may be treated with the receptor peptide-adjuvant composition. Such cancers include but are not limited to ovarian cancer, thyroid cancer, lung cancer, breast cancer, kidney cancer, particularly ovarian cancer.

Further the subject may be treated with the SLC34A2 peptide or immunogenic composition thereof in combination with chemotherapeutic, chemopreventive, or radiation therapy. It is contemplated by this invention that the receptor peptide composition could be used in conjunction with chemo- or radiotherapeutic intervention. In another embodiment, treatment with the receptor peptide composition may precede or follow the DNA damaging agent treatment by intervals ranging from minutes to weeks. Protocols and methods are known to those skilled in the art. DNA damaging agents or factors are known to those skilled in the art and means any chemical compound or treatment method that induces DNA damage when applied to a cell. Such agents and factors include radiation and waves that induce DNA damage such as, gamma-irradiation, X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide.

Combinations of one or more DNA damaging agents may be used with the EHA, whether radiation-based or actual compounds, such as the use of X-rays with cisplatin or the use of cisplatin with etoposide. Other neoplastic or toxic agents include but are not limited: 5-fluorouracil, methotrexate and adriamycin which may be linked in each case to, for example, a cephalosporin (see WO-A94 01 137 and EP-A-0 382 411) or cephalosporin mustards (see EP-A-0 484 870).

The SLC34A2 peptide or immunogenic compositions may be prepared as injectables, as liquid solutions or emulsions. The antigens and immunogenic compositions may be mixed with physiologically acceptable carriers which are compatible therewith. These may include water, saline, dextrose, glycerol, ethanol and combinations thereof. The vaccine may further contain auxiliary substances, such as wetting or emulsifying agents or pH buffering agents, to further enhance their effectiveness. Vaccines may be administered by injection subcutaneously or intramuscularly.

Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories may be desirable. For suppositories, binders and carriers may include, for example, polyalkylene glycols and triglycerides. Oral formulations may include normally employed excipients, such as pharmaceutical grades of saccharine, cellulose and magnesium carbonate.

The modes of administration may comprise the use of any suitable means and/or methods for delivering the adjuvant or adjuvant-containing vaccine to a corporeal locus of the host animal where the adjuvant and associated antigens are immunostimulatively effective. Delivery modes may include, without limitation, parenteral administration methods, such as paracancerally, transmucosally, transdermally, intramuscularly, intravenously, intradermally, subcutaneously, intraperitonealy, intraventricularly, intracranially and intratumorally.

Recombinant Antibodies, Chimerics, Bispecifics and Fragments

Recombinant antibodies, chimeric, bispecifics, fragments, etc. of the antibodies directed against SLC34A2, particularly against amino acids 312-340 of SLC34A2 are provided and encompassed in this invention. Antibodies comprising the variable regin sequences set out in FIGS. 5 and 6, particularly including the CDR regions are contemplated. In general, the CDR regions, comprising amino acid sequences substantially as set out as the CDR regions of FIGS. 5 and 6 will be carried in a structure which allows for binding of the CDR regions to an tumor antigen, including to SLC34A2.

By "substantially as set out" it is meant that that CDR regions of the invention will be either identical or highly homologous to the specified regions of FIGS. 5 and 6. By "highly homologous" it is contemplated that only a few substitutions, preferably from 1 to 8, preferably from 1 to 5, preferably from 1 to 4, or from 1 to 3 or 1 or 2 substitutions may be made in the CDRs. It is contemplated that antibodies having few or several, such as 1 to 3 or 1 or 2 substitutions in the CDRs as set out herein, thus in SEQ ID NOS: 26-28 and/or 31-33, are encompassed by the invention and the term as substantially set out.

The structure for carrying the CDR region(s) of the invention will generally be of an antibody heavy or light chain sequence or substantial portion thereof in which the CDR regions are located at locations corresponding to the CDR region of naturally occurring VH and VL antibody variable domains encoded by rearranged immunoglobulin genes. The structures and locations of immunoglobulin variable domains may be determined by reference to Kabat, E. A. et al, Sequences of Proteins of Immunological Interest. 4th Edition. US Department of Health and Human Services. 1987, and updates thereof, now available on the Internet (http://immuno.bme.nwu.edu)).

Preferably, the amino acid sequence(s) substantially as set out in the CDRs of FIG. 5 (including as set out in SEQ ID NOS: 26-28) are carried as the CDRs in a human heavy chain variable domain or a substantial portion thereof, and the amino acid sequence(s) substantially as set out as the CDRs of FIG. 6 (including as set out in SEQ ID NOS: 31-33) are carried as the CDRs respectively in a human light chain variable domain or a substantial portion thereof. The variable domains may be derived from any germline or rearranged human variable domain, or may be a synthetic variable domain based on consensus sequences of known human variable domains.

Various exemplary SLC34A2 antibodies are provided herein. Thus, an antibody of the present invention comprises a heavy and light chain, wherein the heavy chain variable region comprises the CDR region sequences SEQ ID NO: 26, 27 and 28, and the light chain variable region comprises the CDR region sequences SEQ ID NO: 31, 32 and 33. The invention provides various antibodies directed against SLC34A2 and capable of binding or recognizing SLC34A2, particularly amino acids 312-340, particularly the SLC34A2 peptide and SEQ ID NO: 8. The MX35 variable region sequence comprising CDR regions SEQ ID NO: 26-28, for the heavy chain, and SEQ ID NO: 31-32, served as the basis for generating additional antibodies. Veneered MX 35 is provided herein, an exemplary such veneered antibody comprising the heavy chain variable region sequence SEQ ID NO:38 and the light chain variable region sequence SEQ ID NO: 39. Chimeric MX 35 is provided herein, an exemplary such chimeric antibody comprising the heavy chain variable region sequence SEQ ID NO:40 and the light chain variable region sequence SEQ ID NO: 41. Single chain antibodies have been generated based on the veneered and chimeric MX35 antibodies and are provided herein. ScFv antibody based on veneered MX35 is set out in FIG. 16 and has the amino acid sequence of SEQ ID NO: 42 and the nucleic acid sequence of SEQ ID NO:43. ScFv antibody based on chimeric MX35 is set out in FIG. 17 and has the amino acid sequence of SEQ ID NO: 44 and the nucleic acid sequence of SEQ ID NO:45. Humanized MX35 antibody is another aspect of the invention and is provided herein. The exemplary humanized MX35 antibody comprises a light chain variable region sequence of SEQ ID NO: 35 and a heavy chain variable region sequence of SEQ ID NO: 37 and is depicted in FIGS. 11A and 11B. The heavy chain variable region of humanized MX35 comprises the CDR regions as set out in SEQ ID NO: 26, 27 and 28. The light chain variable region of humanized MX35 comprises the CDR regions as set out in SEQ ID NO: 31, 32 and 33.

For example, Marks et al (Bio/Technology, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR.

Analogous shuffling or combinatorial techniques are also disclosed by Stemmer (Nature, 1994, 370:389-391), who describes the technique in relation to a β-lactamase gene but observes that the approach may be used for the generation of antibodies. A further alternative is to generate novel VH or VL regions carrying the CDR3-derived sequences of the invention using random mutagenesis of, for example, the mAb VH or VL genes to generate mutations within the entire variable domain. Such a technique is described by Gram et al (1992, Proc. Natl. Acad. Sci., USA, 89:3576-3580), who used error-prone PCR. Another method which may be used is to direct mutagenesis to CDR regions of VH or VL genes. Such techniques are disclosed by Barbas et al, (1994, Proc. Natl. Acad. Sci., USA, 91:3809-3813) and Schier et al (1996, J. Mol. Biol. 263:551-567).

All the above described techniques are known as such in the art and in themselves do not form part of the present invention. The skilled person will be able to use such techniques to provide specific binding members of the invention using routine methodology in the art.

Single binding domains based on either of the variable region sequences set out in FIGS. 5 and 6, or based on SLC34A2 antibodies more generally disclosed and provided herein, form further aspects of the invention. In the case of either of the single chain specific binding domains, these domains may be used to screen for complementary domains capable of forming a two-domain specific binding member which has in vivo properties as good as or equal to the mAb antibody(ies) disclosed herein. This may be achieved by phage display screening methods using the so-called hierarchical dual combinatorial approach as disclosed in U.S. Pat. No. 5,969,108 in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al, ibid.

Antibodies of the present invention may further comprise antibody constant regions or parts thereof. For example, specific binding members based on the sequences of MX35 or other antibodies herein, may be attached at their C-terminal end to antibody light chain constant domains including human Cκ or Cλ chains, preferably Cλ chains. Similarly, specific binding members based on SEQ ID NO: may be attached at their C-terminal end to all or part of an immunoglobulin heavy chain derived from any antibody isotype, e.g. IgG, IgA, IgE, IgD and IgM and any of the isotype subclasses, particularly IgG1, IgG2b, and IgG4. IgG1 is preferred.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

Monoclonal Antibody MX35 Detects the Membrane Transporter NaPi2b (SLC34A2) in Human Carcinomas: a New Target for Cancer Immunotherapy Mouse monoclonal antibody MX35 was developed against ovarian cancer and the antibody showed homogeneous reactivity with approximately 90% of human ovarian epithelial cancers but with only a limited number of normal tissues by immunohisto-chemistry. Although mAb MX35 has been used in a number of clinical trials in ovarian cancer, it had been difficult to define the molecular identity of MX35. We report here that mAb MX35 recognizes the sodium-dependent phosphate transport protein 2b (NaPi2b) in human cancer cells. This conclusion is based on several lines of experimental evidence, including 1) identification of SLC34A2, the gene coding for NaPi2b, by immunoscreening of an ovarian cancer cell line derived cDNA expression library with mAb MX35; 2) mass spectrometry sequencing of peptides obtained by fragmentation from mAb MX35 affinity-purified antigen, which showed complete sequence homology to amino acid sequences in NaPi2b; 3) selective down-regulation of SLC34A2 gene expression by RNA interference and the resulting loss of mAb MX35 binding to MX35-expressing human cancer cells; and 4) demonstrating specific mAb MX35 reactivity with recombinant fusion proteins and with synthetic peptides of the putative largest extracellular loop of NaPi2b. We further showed that NaPi2b in cancer cells is expressed on the cell surface as a heavily N-glycosylated protein, with evidence of additional post-translational modifications, such as palmitoylation and formation of di-sulfide bridges in the major extracellular loop. Membrane transporter molecules, such as NaPi2b, represent a new family of potential cell surface targets for immunotherapy of cancer with monoclonal antibodies.

Materials and Methods

Cell Lines and Antibodies:

All cell lines were obtained from the cell bank of the Ludwig Institute for Cancer Research, New York Branch at Memorial Sloan-Kettering Cancer Center. Murine mAb MX35 (IgG1) was purified from hybridoma supernatant by protein G chromatography.

Immunoscreening of OVCAR-3 cDNA Library:

The cDNA expression library from OVCAR-3 cell line has been described (19). A total of $1\times10^6$ recombinants phages were screened with MX35 monoclonal antibody (5 μg/ml TBS with 0.2% non-fat dried milk) for 15 hrs at room temperature. MX35 positive clones were further confirmed by secondary and tertiary screening. Isolated positive phages were converted into pBK-CMV phagemid using the Stratagene (La Jolla, Calif.) in vivo excision protocol. Rescued plasmid DNAs were purified using a miniprep kit (Qiagen, Valencia, Calif.) and subjected to restriction analysis and DNA sequencing.

Metabolic Radiolabeling of Cultured Cells:

Cultured cells were metabolically labeled with Tran $^{35}$S-label mixture (MP Biomedicals, Inc. Irvine, Calif.) and $^3$H-Glucosamine (Amersham Biosciences UK, Buckinghamshire, UK) as described previously (20). Metabolic palmitoylation using $^3$H-palmitic acid was performed as described (21).

Radioimmunoprecipitation, SDS-PAGE, Autoradiography and Immunoblotting:

Radioimmunoprecipitation, SDS-PAGE, autoradiography and immunoblotting were performed as described (21).

MALDI-TOF/TOF Mass Spectrometry:

Metabolic labeling, immunoprecipitation, SDS-PAGE and detection of $^{35}$S-labeled proteins were performed as described earlier. In-gel tryptic digestion and peptide mass fingerprinting were performed as described (22) with additional treatment of excised protein bands with DTT before destaining and digestion. In parallel experiments, extracted peptides were subjected to labeling of lysine amino acid residues using 2-methoxy-4,5 dihydro-1H-imidazole (23) and to sulphonation of the N-terminus of peptides to improve fragmentation (Ettan CAF MALDI sequencing kit, GE healthcare Amersham Biosciences AB, Uppsala, Sweden). Peptides were subjected to "de-novo" sequencing by fragmentation using post-source decay in a Bruker Ultraflex MALDI TOF/TOF instrument (Bruker Daltonics, Bremen, Germany). The PSD spectra were interpreted manually. Experiments were performed with two different cell lines, OVCAR-3 and SK-RC-18, and three repeats for each cell line.

RNA Interference Assay:

Two different sets of SLC34A2 specific SMARTpool siRNA (ON-Targetplus™ and siGENOME) and nontargeting SMARTpool siRNA controls (ON-Targetplus™ siCONTROL and standard siCONTROL) were purchased from Dharmacon, Inc. (Lafayette, Colo.). The transfection of siRNA was performed in the presence of Lipofectamine 2000 and Opti-MEM media (Invitrogen, Carlsbad, Calif.) according to the manufacturer's instructions at a final concentration of 40 nM. Cells treated with Lipofectamine 2000 only and non-targeting siRNA pools were used as controls. Seventy two hours after the transfection, cells were processed for MHA, real-time PCR and western blot analysis.

RNA Isolation, Reverse Transcription (RT)-PCR Analysis and Real-Time PCR:

RNA isolation, reverse transcription (RT)-PCR analysis (24) and real-time PCR was performed using standard molecular biology techniques. Gene specific primers used to amplify SLC34A2 by RT-PCR were 5'-TCA GCC AAA TTG CAA TGA AC-3' and 3'-ATC ATG ATC AGG CAA CCA CA-5'.

Cloning, Expression and Purification of GST/NaPi2b Fusion Proteins:

Various regions of the human NaPi2b large extracellular loop were PCR amplified and cloned into pGEX4T1 vector in frame with GST. Expression of GST/NaPi2b fusions in BL21 DE3 cells was induced by 1 mM IPTG for 3 hours at 37° C. Cell pellets were disrupted by sonication in lysis buffer (25 mM TrisHCl, pH 7.5, 150 mM NaCl, 1 mM EDTA, 0.5% Triton and protease inhibitor cocktail (Boehringer Mannheim, Germany) and GST fusion proteins were purified from clarified supernatants by affinity chromatography using GST-Sepharose as recommended by the manufacturer. Expression details of His-NaPi2b-ECD in Sf9 insect cells is given in SI-text.

Mixed Hemadsorption Assays:

The mixed hemadsorption assay (MHA), which detects surface-bound IgG by adherence of rabbit anti-mouse IgG coated human red blood cells (blood group O) to target cells, was performed as described (25).

Synthetic Peptide Microarray:

Membrane arrays of synthetic peptides overlapping amino acids 312-340 of the NaPi2b protein sequence were custom prepared (JPT Peptide Technologies, Inc., Springfield, Va.).

For epitope mapping, membranes were incubated for 3 hours with 1 ug/ml primary antibody, followed by incubation with HRP-labeled goat anti-mouse polyclonal antibodies (Jackson ImmunoResearch Laboratories, West Grove, Pa.) for 2 hours. Bound antibody was visualized by chemiluminescence (Western Lightning Plus). For epitope mapping under reducing condition, membranes were incubated in 1 mM DTT for 1 hour at room temperature, and then washed extensively prior to antibody incubation.

Peptide Blocking and Peptide ELISA:

A peptide corresponding to amino acids 312-340 of NaPi2b was chemically synthesized (Bio-Synthesis, Inc. Lewisville, Tex.) and co-incubated at varying concentrations with mAb MX35 prior assaying mAb MX35 binding to MX35-positive and MX35-negative cells by MHA. Binding of mAb MX35 to the synthetic peptide 312-340 was also assayed by ELISA using NUNC Maxisorp plates, to which the peptide (10 ug/ml in water) was adsorbed for 2 hours at RT.

Triton X-114 Extraction and Glycosidase Treatments and Acylation Analysis:

Triton X-114 extraction of membrane proteins is described in detail in SI-text. Aliquots of $^{35}$S-labeled or $^{3}$H-glucosamine-labeled immune complexes were subjected to treatment with various glycosidases: N-Glycanase; PNGaseF (5 mU), Sialidase A (5 mU), O-Glycanase (1.25 mU), β(1-4) Galactosidase (3 mU), and β-N-Acetylglucosaminidase (40 mU) using the Prozyme Enzymatic Deglycosylation Kit (Glyko, San Leandro, Calif.) according to manufacturer's instruction. Deglycosylation was monitored by SDS-PAGE, autoradiography and Western blot analysis as described above. $^{3}$H-palmitoyl-labeled NaPi2b was obtained by immunoprecipitation from SK-RC-18 cells cultured in the presence of $^{3}$H-palmitic acid, separated by 4-12% Bis-Tris SDS-PAGE gel, and visualized by autoradiofluorography. To test for thioester bound palmitic acid SDS-PAGE gels were preincubated with 0.2 M potassium hydroxide in methanol, methanol, or 1 M hydroxylamine-hydrochloric acid, pH 7.5 or 1 M Tris, pH 7.5, followed by autoradiography (21).

Results

Molecular Cloning of the MX35 Antigen by Immunoscreening of an OVCAR-3 cDNA Expression Library Screening of a cDNA library generated from the ovarian cancer cell line OVCAR-3, which expresses MX35 antigen on its cell surface, identified three distinct mAb MX35-reactive clones (N1, N4 and N6). Reactivity of the three clones was confirmed in a secondary screening. Subsequent cDNA restriction analysis and sequencing identified the strongest mAb MX35-reactive clone N1 as encoding a N-terminally truncated form of the sodium-dependent phosphate transport protein 2b (gene SLC34A2, size 3394 bp; fragment 742 bp-4135 bp), clone N4 a N-terminally truncated form of Zinc-finger protein 638 (ZN638, size 4637 bp; fragment 1798 bp-6434 bp), and clone N6 a N-terminally truncated form of the same Zinc-finger protein 638 (size 3585 bp; fragment 2850 bp-6434 bp).

Confirmation of the Identity of MX35 Antigen as the Sodium-Dependent Phosphate Transport Protein 2b (Gene SLC34A2)

(i) Co-Typing of mRNA Expression and MX35 Antigen Cell Surface Expression

A panel of cancer cell lines was co-typed for SLC34A2 mRNA expression by RT-PCR and for cell surface expression of MX35 protein antigen in a mixed hemadsorption assay (MHA) using mAb MX35 as probe. In addition, cell lysates were probed by Western blot analysis for MX35 expression. A panel of cancer cell lines with known expression of MX35 antigen was included. Strong expression of SLC34A2 mRNA correlated with MX35 antigen cell surface expression in all cells analyzed (Table 1). No such correlation was found for the Zinc-finger protein 638 (data not shown).

TABLE 1

SLC34A2 mRNA and MX35 protein expression in a panel of different cancer cell lines

| Cell Lines | Tumor type | RT-PCR | MHA | WB | Cell Lines | Tumor type | RT-PCR | MHA | WB |
|---|---|---|---|---|---|---|---|---|---|
| SK-LC-1 | lung | +++ | +++ | +++ | BT 20 | breast | + | − | − |
| SK-LC-17 | lung | + | − | − | SK-BR-3 | breast | + | − | − |
| SK-MEL-37 | melanoma | ++ | − | − | MCF 7 | breast | + | − | − |
| SK-RC-1 | renal | − | − | − | BT-474 | breast | + | − | − |
| SK-RC-18 | renal | +++ | +++ | +++ | HCT 15 | colon | + | − | − |
| SK-RC-33 | renal | +++ | +++ | ++ | U251 | glioma | + | − | − |
| A10 | ovary | +++ | +++ | − | U87MG | glioma | + | − | − |
| SK-OV-6 | ovary | +++ | +++ | + | SK-MG-1 | glioma | + | − | − |
| OVCAR3 | ovary | +++ | +++ | +++ | U373 | glioma | + | − | − |
| SW626 | ovary | + | − | − | | | | | |

(ii) Mass Spectrometry Sequencing by Fragmentation of Peptides

Immunoprecipitation of the MX35 antigen from two different MX35 antigen-positive cell lines, OVCAR-3 and SK-RC-18, following metabolic labeling of proteins with [$^{35}$S] methionine and [$^{35}$S] cysteine showed one major (~90 kDa) and one minor (~180 kDa) band on SDS-PAGE (FIG. 1A). Subsequently, preparative quantities of the MX35 immune complexes were separated by SDS-PAGE and $^{35}$S-labeled protein bands were excised and subjected to tryptic digestion followed by sequencing by fragmentation of peptides using mass spectrometry. Fragmentation of four selected peptides provided amino acid sequences VITKPFTK, LIVQLDKK, IWCK and SLKPWDAVVSK (FIG. 1B), which showed complete alignment to amino acids 266-273, 274-281, 301-304 and 599-609 in the NaPi2b protein sequence (FIG. 1C). The NaPi2b peptides were identified in both protein bands. This identifies sodium-dependent phosphate transport protein 2b as the MX35 antigen, rather than the Zn-finger protein also selected in the initial molecular screen.

(iii) RNA Interference

Two different sets of SLC34A2-specific "on-target" siRNAs were prepared to analyze if selective down-regulation of SLC34A2 gene expression by RNA interference would result in a loss or reduced binding of MX35 antibody in MX35-expressing cancer cells. Both SLC34A2-specific siRNA sets selectively down-regulated SLC34A2 mRNA in SK-RC-18 and OVCAR-3 cells as determined by real-time RT-PCR (FIG. 2A). Binding of MX35 antibody to cell surface expressed MX35 antigen was significantly reduced as determined in MHA (data not shown). Specific down-regulation of MX35 protein antigen levels was confirmed by Western blot analysis (FIG. 2B). "Non-targeting" siRNA had no effect on the expression levels of SLC34A2 mRNA and MX35 protein antigen in both cell lines. These results further validate NaPi2b as the MX35 antigen.

Mapping of the Antibody Binding Site in NaPi2b

Figure 3:
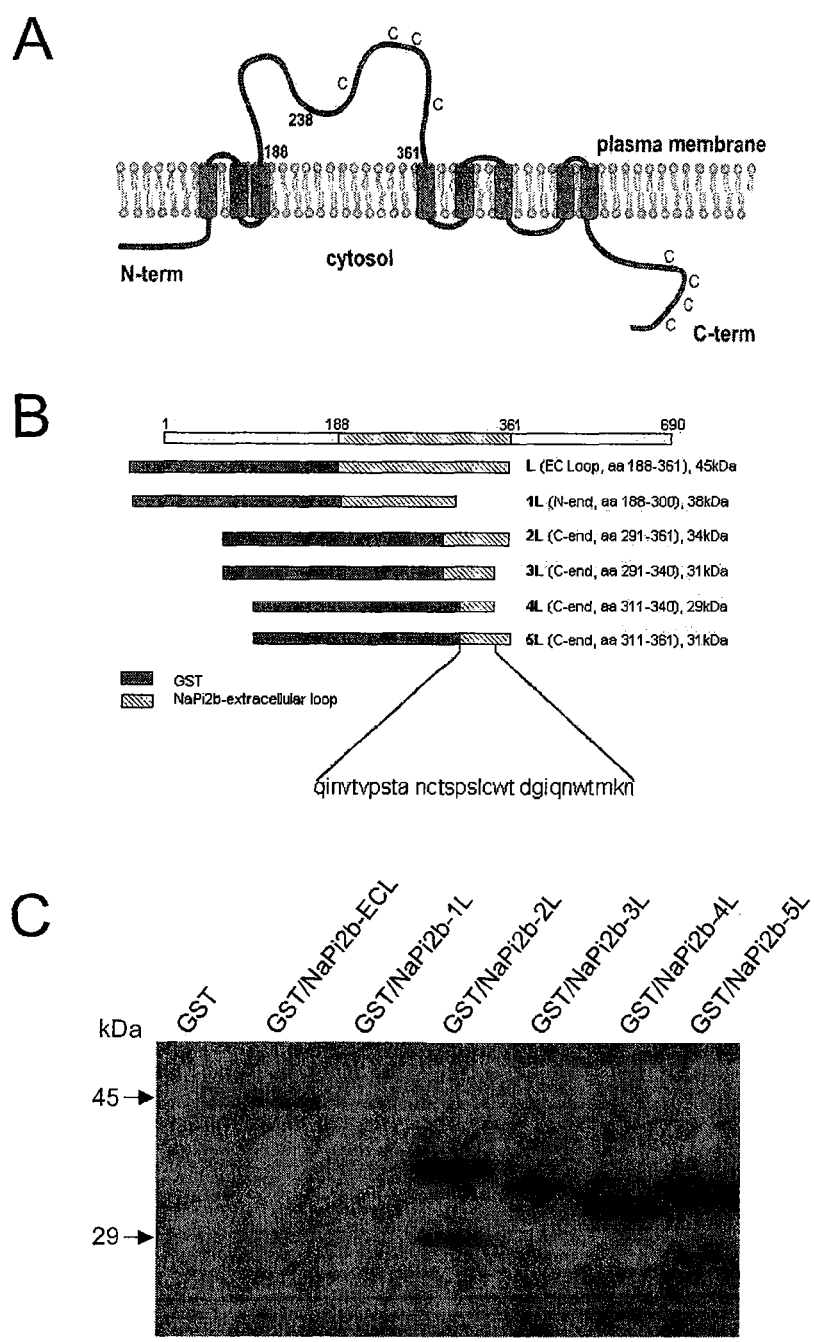
FIG. 3: (A) Schematic diagram of the predicted membrane topology of the sodium dependent phosphate transporter 2b protein; (B) Schematic presentation of the NaPi2b protein and fusion proteins derived from the potentially largest extracellular region aa188-361 and the location of MX35 epitope; (C) NaPi2b fusion proteins expressed in bacteria and immunoblotted with MAb MX35 after separation by SDS-PAGE.

Bioinformatic analysis suggested that the protein encoded by SLC34A2 has at least 8 potential transmembrane domains, 5 putative intracellular domain sites and 4 putative extracellular domain loops with both the N- and C-terminal regions facing the cytoplasm (FIG. 3A). Taking into account that mAb MX35 recognizes an epitope expressed on the cell surface, the potentially largest potential ECD loop was expressed as a GST-fusion protein (covering aa 188-361 of NaPi2b) (FIG. 3B) in E. coli and as a His-tagged protein in Sf9 insect cells using a baculovirus expression system, and were probed for reactivity with Mab MX35 in Western blots. Both fusion proteins were recognized by mAb MX35. Preincubation mAb MX35 with the bacterial fusion protein could selectively block binding of mAb MX35 to naturally expressed MX35 antigen in ovarian cancer tissue by immunocytochemistry (data not shown). Subsequently, shorter fusion proteins, truncated from the N-terminus and the C-terminus (FIG. 3B) were studied and the mAb MX35-binding epitope was narrowed down to a fusion protein containing amino acids 311-340 of the NaPi2b protein sequence (FIG. 3C). Binding of mAb MX35 to this peptide sequence was further confirmed by ELISA and dot blot immune stain using as the antigen a synthetic 29mer peptide representing amino acids 312-340 of the NaPi2b protein. This peptide was further truncated from the N-terminus and the C-terminus and the MX35-reactive epitope was narrowed to amino acids 324-338 as determined in a peptide spot analysis (Table 2). Within this region the WTM sequence (aa 336-338) seems to be highly critical for antibody recognition. Although the amino acid region 324-338 (SPSLCWTDGIQNWTM) of the human protein is highly homologous to the murine counterpart (SPSYCWTDGIQNWTI) in the NaPi2b protein, the murine protein was not recognized by mAb MX35 in a Western blot analysis of various mouse tissues, further confirming WTM as critical for MX35 antibody recognition (data not shown). Interestingly, the Cys residues at position 322 and 328 are not required, as they could be replaced with Ala residues, even though antibody reactivity with the full length wild type NaPi2b is reduction sensitive. These amino acids are probably not involved in the cysteine loop postulated to stabilize the epitope; this loop probably spans aa 303 to aa 350 (FIG. 1C; UniProtKB/Swiss-Prot entry O05436).

TABLE 2

MAb MX35 epitope mapping using a series of synthetic peptides located in a putative extracellular domain (aa 312-340) of the NaPi2b protein

| NaPi2b aa Position | Amino Acid Sequence | Reactivity with mAb MX35 |
|---|---|---|
| 312-340 | Ac-INVTVPSTANCTSPSLCWTDGIQNWTMKN-amide | +++ |
| 312-340 | Ac-INVTVPSTANATSPSLCWTDGIQNWTMKN-amide | + |
| 312-340 | Ac-INVTVPSTANCTSPSLAWTDGIQNWTMKN-amide | + |
| 312-340 | Ac-INVTVPSTANATSPSLAWTDGIQNWTMKN-amide | +++ |
| 317-340 | Ac-PSTANCTSPSLCWTDGIQNWTMKN-amide | + |
| 320-340 | Ac-ANCTSPSLCWTDGIQNWTMKN-amide | ++ |
| 323-340 | Ac-TSPSLCWTDGIQNWTMKN-amide | + |
| 312-335 | Ac-INVTVPSTANCTSPSLCWTDGIQN-amide | − |
| 312-331 | Ac-INVTVPSTANCTSPSLCWTD-amide | − |
| 312-327 | Ac-NVTVPSTANCTSPSL-amide | − |
| 317-331 | Ac-PSTANCTSPSLCWTD-amide | − |
| 312-326 | Ac-INVTVPSTANCTSPS-amide | − |
| 315-329 | Ac-TVPSTANCTSPSLCW-amide | − |
| 318-332 | Ac-STANCTSPSLCWTDG-amide | − |
| 321-335 | Ac-NCTSPSLCWTDGIQN-amide | − |
| 324-338 | Ac-SPSLCWTDGIQNWTM-amide | + |

Further Biochemical Characterization of the MX35 Antigen (NaPi2b)

(i) General Characteristics

Western blot analysis and radioimmunoprecipitation experiments with mAb MX35 showed that the protein is expressed in OVCAR-3 and SK-RC-18 cells in at least two major forms, one migrating in a SDS-PAGE at ~90 kDa and a second migrating at about 180 k (FIG. 1A); these could be monomeric and dimeric forms of the protein. While mAb MX35 recognition of its antigen is sensitive to reduction, immunoprecipitation of metabolically labeled MX35 antigen showed no obvious difference in the SDS-PAGE migration pattern between reducing and non-reducing conditions.

Extraction of protein from OVCAR-3 cells with Triton-X114 detergent showed that almost all of the mAb MX35-reactive protein partitioned into the lower, detergent enriched fraction, confirming that NaPi2b is an integral membrane protein (data not shown).

(ii) Glycosylation Characteristics

Sequence analysis of the SLC34A2 gene product predicts 5 potential N-glycosylation sites at N295, N308, N313, N321 and N340 (FIG. 1C). Interestingly, all 5 putative glycosylation sites appear clustered within a rather short peptide region (aa 295-340) located in the largest predicted extracellular domain loop to which the mAb MX35 epitope was also mapped (FIG. 1C). Metabolic labeling of SK-RC-18 cells with $^3$H-glucosamine followed by immune precipitation with mAb MX35 showed that NaPi2b is indeed heavily glycosylated (FIG. 4B) and treatment with N-glycanase but not O-glycanase removed most of this label. Treatment of [$^{35}$S] Met- and Cys-labeled immunoprecipitates with various glycosidases showed that the glycan chains were sensitive to N-glycosidase confirming that almost all sugars in MX35 antigen were N-linked as predicted. Only a minor proportion of the carbohydrate was sensitive to O-glycosidase and sialidase or to a mixture of O-glycosidase, sialidase, β-galactosidase and N-acetylglucosaminidase. Treatment with a combination of N- and O-glycosidases resulted in a migration shift of the MX35 reactive bands in SDS-PAGE from ~90 kDa to 55-60 kDa and from ~180 kDa to 130-140 kDa. The former figure is much lower than the peptide size predicted for the unprocessed protein from its cDNA sequence (75.7 kDa) but the protein may migrate anomalously on SDS-PAGE because of its many hydrophobic regions.

(iii) Acylation Characteristics

Figure 4:
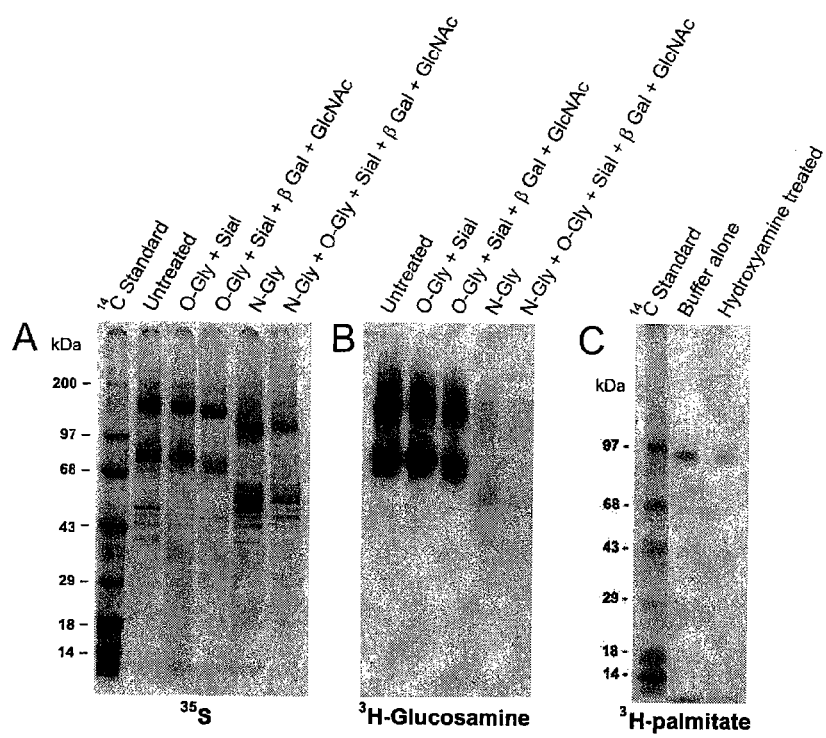
FIG. 4: NaPi2b/MX35 antigen biochemical characterization. MAb MX35 immune precipitations from metabolically labeled SK-RC-18 cell lysates separated by SDS-PAGE under reducing conditions and visualized by autoradiography. (A) Enzymatic deglycosylation analysis of $^{35}S$-labeled immune complexes analyzed; (B) Enzymatic deglycosylation analysis of immune complexes derived from $^{3}H$-glucosamine labeled cells; (C) Acylation analysis of immune complexes from $^{3}H$-palmitate labeled cells.
Figure 8:
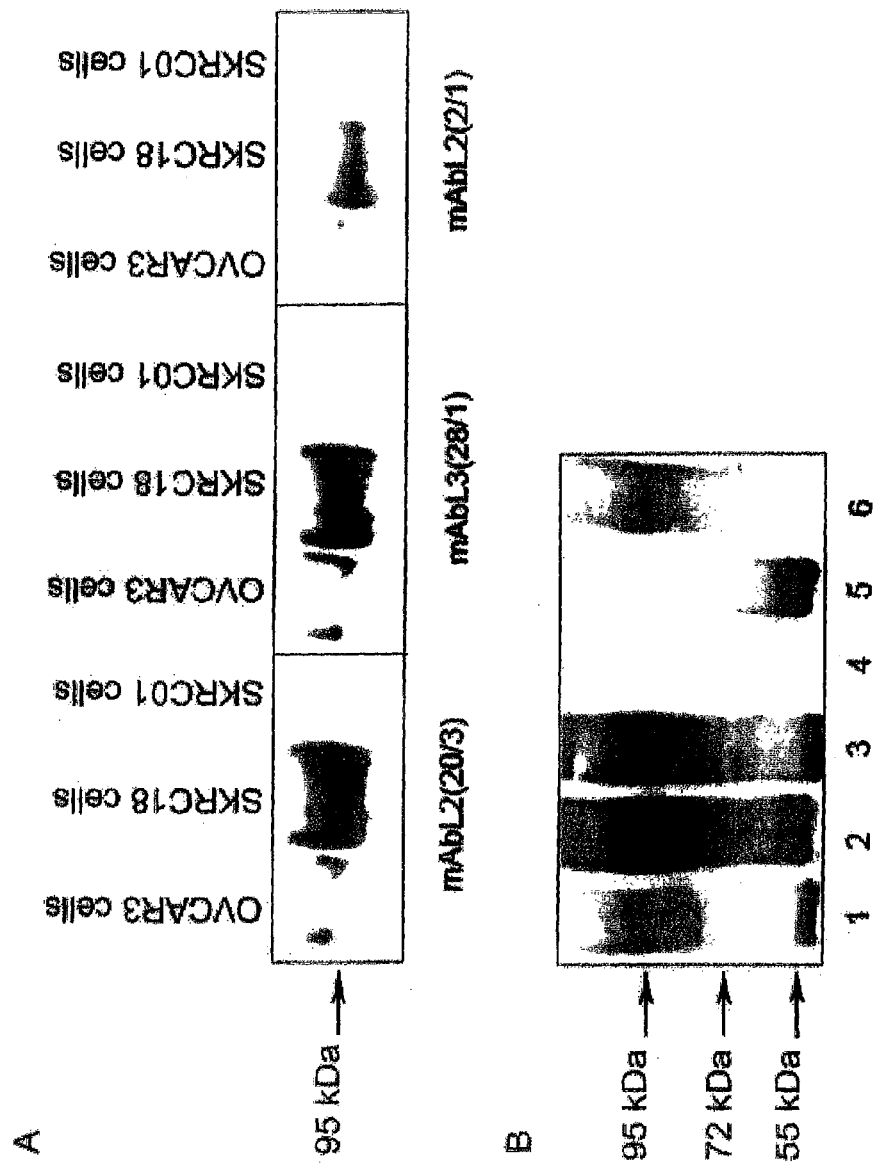
FIG. 8 shows Western blot analysis (A) and immunoprecipitation (B) of transiently overexpressed and endogenous NaPi2b. (A) Specific recognition of endogenous NaPi2b by generated antibodies in Western blot analysis. Total cell lysates (10 μg) from OVCAR3, SKRC18 and SKRC01 cell lines were separated by SDS-PAGE under non-reducing (without DTT) conditions and probed with generated monoclonal antibodies. (B). Immunoprecipitation of transiently overexpressed myc-NaPi2b. Hek293 cells were transiently trasnfected with pcDNA3.1/myc-NaPi2b. The supernatants of transfected cells were incubated with Protein A Sepharose containing IgGs from L2(2/1), L2(20/3), L3(28/1) hybridoma clones. The immune complexes were resolved by SDS-PAGE and immunoblotted with L2(20/3) MAb.
Figure 9:
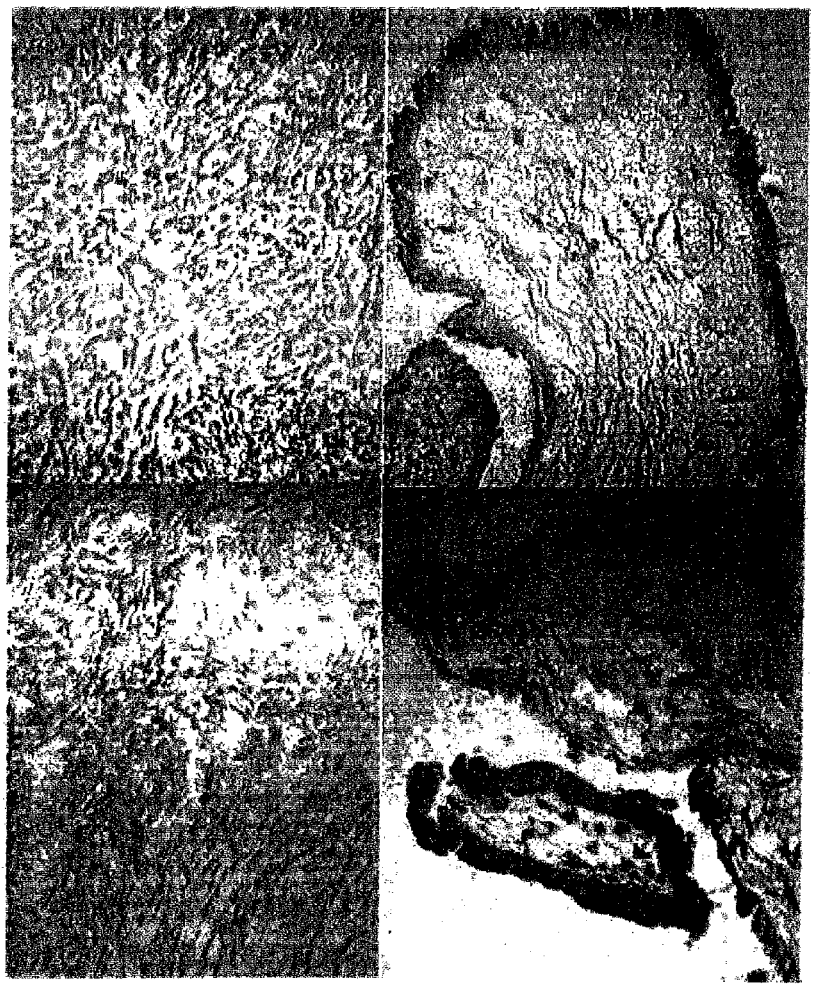
FIG. 9 provides immunohistochemical analysis of ovarian tissues with NaPi2b/(20/3) and NaPi2b/(28/1) MAb. Immunohistochemical staining of paraffin-embedded sections of normal ovary and ovarian carcinoma with L2(20/3) (A) and L3(28/1) (B) antibodies.
Figure 12:
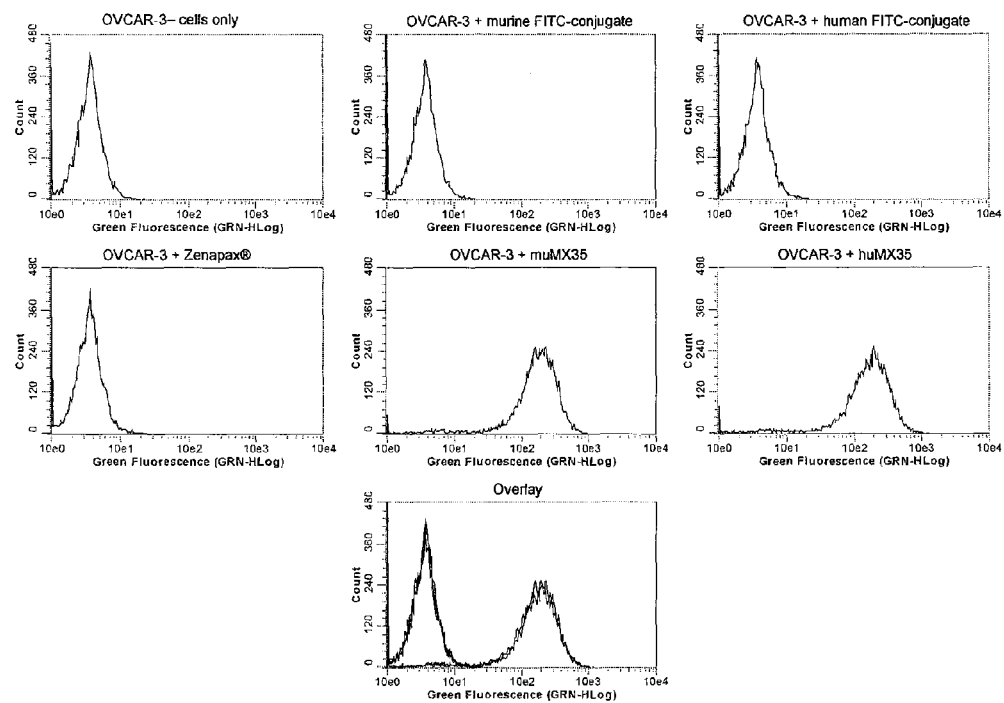
FIG. 12 provides flow cytometry analysis assessing binding of the humanized MX35 antibody to OVCAR-3 cells from ovarian carcinoma. Results are compared to those obtained with "cells only", "murine FITC-conjugate control", "Zenapax®" and "murine MX35" controls.
Figure 13:
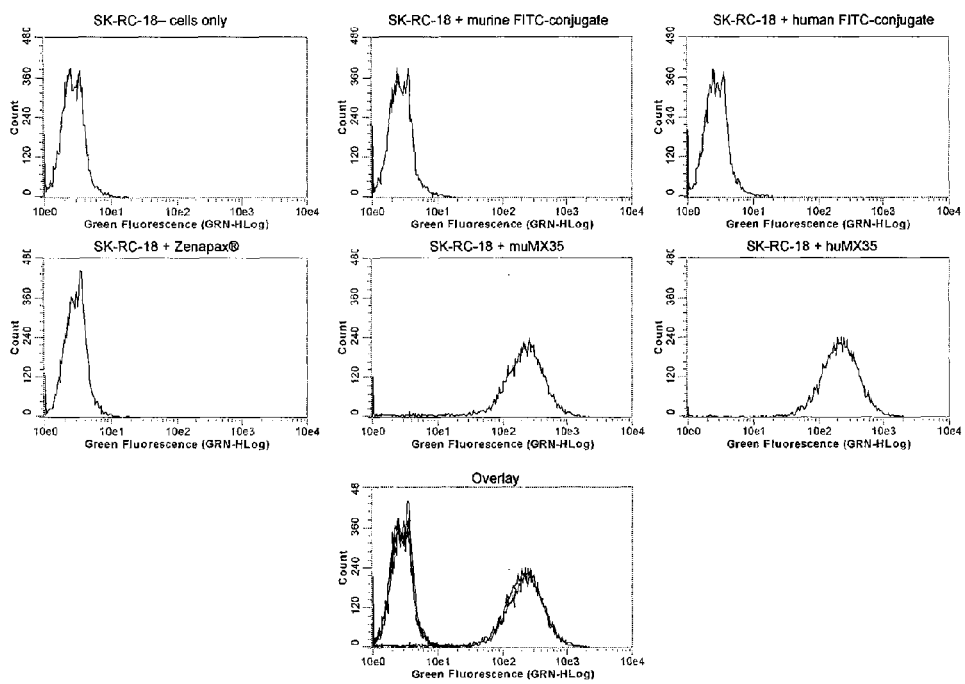
FIG. 13 provides flow cytometry analysis assessing binding of the humanized MX35 antibody to SK-RC-18 cells from renal carcinoma. Results are compared to those obtained with "cells only", "murine FITC-conjugate control", "Zenapax®" and "murine MX35" controls.
Figure 14:
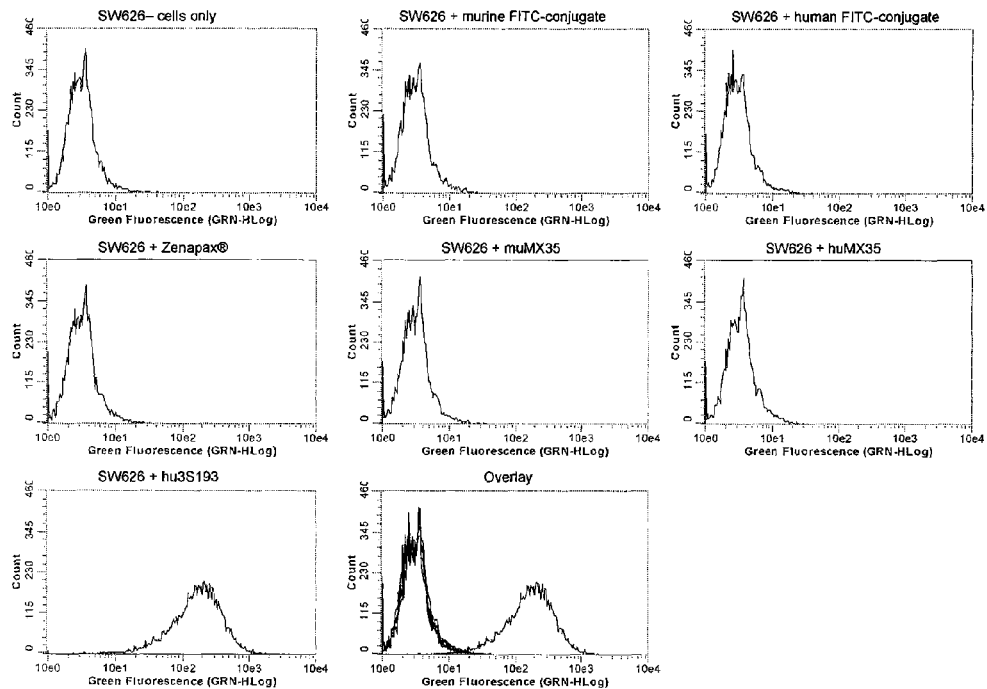
FIG. 14 provides flow cytometry analysis assessing binding of the humanized MX35 antibody to SW626 cells, derived from an ovarian metastasis (primary tumor is at colon). Results are compared to those obtained with "cells only", "murine FITC-conjugate control", "Zenapax®", "murine MX35" and "huH3S193" controls.
Figure 15:
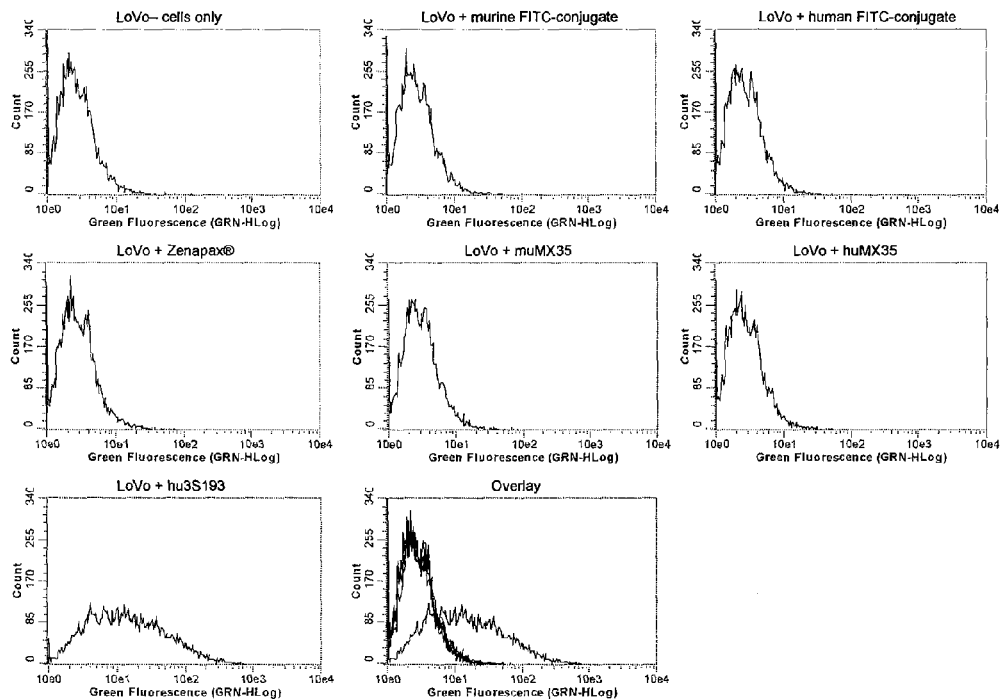
FIG. 15 provides flow cytometry analysis assessing binding of the humanized MX35 antibody to LoVo cells from colorectal carcinoma. Results are compared to those obtained with "cells only", "murine FITC-conjugate control", "Zenapax®", "murine MX35" and "huH3S193" controls.

Bioinformatic studies revealed a cysteine-rich region at the C-terminal end, which could be potential sites for palmitoylation. Indeed, metabolic labeling of SK-RC-18 cells with $^3$H-palmitic acid followed by immune precipitation with mAb MX35 and SDS-PAGE analysis suggests that MX35 protein is acylated (FIG. 4C). Treatment with base showed that acylation is partially reversible.

Discussion:

MAb MX35 was developed as a therapeutic reagent for the treatment of ovarian cancer. In phase I clinical trials radiolabeled murine antibody MX35 targeted well to tumors in patients with ovarian cancer (2, 3) and the antibody is currently being studied in a phase I clinical trial as carrier of alpha-particle-emitting radionuclide astatine-211 for radio-immunotherapy of ovarian cancer (6). Although, there has been this clinical exploration of mAb MX35 it had been difficult to define the molecular identity of the MX35 antigen. We now have unambiguously identified the sodium-dependent phosphate transport protein 2b (NaPi2b) as the molecular target recognized by mAb MX35. This conclusion is based on the following experimental evidence:

1) A clone encoding for a N-terminally truncated form of NaPi2b (gene SLC34A2, size 3394 bp; fragment 742 bp-4135 bp) was isolated from a cDNA library generated from the ovarian cancer cell line OVCAR-3, which expresses MX35 on its cell surface; 2) Co-typing of a panel of cancer cell lines showed a good correlation of SLC34A2 RNA expression by RT-PCR and MX35 cell surface expression as determined by mixed hemadsorption assays; 3) Isolation of MX35 from MX35-expressing cancer cell lines OVCAR-3 and SK-RC-18 and subsequent protein sequencing by fragmentation of peptides using mass spectrometry provided amino acid sequences that showed complete alignment to amino acid sequences in NaPi2b; 4) Selective down-regulation of SLC34A2 gene expression in MX35-expressing cancer cells by RNA interference resulted in the loss or reduced binding of mAb MX35; 5) The largest putative extracellular loop of the multi-transmembrane protein NaPi2b was expressed in *E. coli* and in insect cells and both expression products were recognized by mAb MX35 in Western blot assays and blocked binding of mAb MX35 to ovarian cancer tissues in immunohistochemistry; 6) A small synthetic peptide with 100% sequence homology to amino acids 312-340 of the major extracellular loop of NaPi2b was reactive with mAb MX35 in dot blot assays and by ELISA.

SLC34A2 is a member of the solute carrier gene family (8, 9) and the gene maps to chromosome 4p15.2. The SLC34A2 gene codes for a multi-pass membrane protein of 690 amino acids (FIG. 3A). This protein has been reported to mediate transport of inorganic phosphate into epithelial cells via sodium ion co-transport and may have a role in phosphate homeostasis (for review see (10, 11)) and in the synthesis of surfactants in lung alveoli (12). The human protein, sodium-dependent phosphate transport protein 2b (NaPi2b) or solute carrier family 34 member 2, has also several other synonyms. SLC34A2 cDNA was at first isolated and cloned from a human small intestine and lung cDNA library (8, 9) and subsequent gene expression analysis by Northern Blot showed that SLC34A2 was highly expressed in the lung and at low to moderate levels in several other normal human tissues including trachea, kidney, small intestine, ovary, placenta, uterus, testis, prostate, pancreas, mammary gland, thyroid gland, salivary gland. An EST database search confirmed expression of the SLC34A2 gene in thyroid, ovary, lung, trachea and mammary gland but showed only a few EST counts for kidney, small intestine, placenta, uterus, testis and prostate. Expression in the lung was further confirmed by genome scans (13, 14) and mRNA visualization by "in-situ" hybridization showed the highest expression in alveolar type II cells (13). Increased SLC34A2 gene expression has been reported for ovarian cancer (15) and papillary thyroid cancer (16).

So far, the human SLC34A2 has been characterized largely on the gene level and NaPi2b transporter activities were generally studied with recombinant protein expressed in xenopus oocytes (8, 9, 13, 17, 18). Little has been reported on the biochemistry of the naturally expressed protein product of SLC34A2. In this report, we provide experimental evidence that NaPi2b is naturally expressed as a heavily glycosylated plasma membrane protein in cancer cells. We could show that the predicted potentially largest ECD (aa 188-361) of NaPi2b is indeed expressed on the cell surface, or at least the major part of it, as the antigenic epitope recognized by mAb MX35 (aa 324-338) is located within the predicted ECD and mAb MX35 bound to NaPi2b expressing cancer cells in a MHA cell surface binding assay. We also provide experimental evidence that the predicted disulfide bridge in the ECD of NaPi2b is formed between C303 and C350 and does not involve C322 and C328. This is based on the observation that mAb MX35 can only react with non-reduced, naturally expressed NaPi2b, but recognized the synthetic peptide 311-340 (containing C322 and C328) in both, reduced and non-reduced form. NaPi2b is heavily glycosylated and we have shown by exoglycosidase cleavage that the vast majority of the carbohydrates are N-linked. Predicted N-glycosylation sites are located in the ECD at amino acids N295, N308, N313, N321 and N340. It is of interest that all predicted glycosylations sites are within or are in close proximity to the amino acid epitope recognized by mAb MX35 (aa 324-338) but do not interfere with binding of the antibody as both glycosylated and non-glycosylated NaPi2b bound equally well to mAb MX35 in Western blot assays and immune precipitation assays. We also provide experimental evidence for further posttranslational modifications of NaPi2b, showing by metabolic labeling that palmitate was incorporated into the protein indicating that NaPi2b is likely to be naturally palmitoylated. Potential palmitoylation sites may be located within the C-terminal cytoplasmic domain, which contains a cysteine rich stretch of 17 cysteines within amino acids 613-645. Acylation of NaPi2b was partially reversible by treatment with hydroxylamine suggesting that NaPi2b may be palmitoylated both transiently and permanently. The protein appears to be expressed in the plasma membrane in at least two major forms distinguishable by their apparent molecular weight (90 kDa and 180 kDa) by SDS-PAGE, and which probably represent monomeric and dimeric forms of the protein as determined by mass spectrometry. Presence of homodimeric forms of NaPi2b have been proposed based on freeze fracture microphotograph analysis of oocytes expressing recombinant flounder NaPi2b (11).

With the identification of mAb MX35 recognizing a protein product of SLC34A2 it has now become possible to link mRNA expression profiles of the SLC34A2 gene with its gene products on the protein level and to study NaPi2b expression in normal tissues and in cancer. Whether the SLC34A2 gene products in cancer and in normal tissues are the same or are different will need to be determined as anomalous SLC34A2 gene expression has recently been reported. Exon mutations in SLC34A2 (the gene contains 13 exons of which 12 are coding exons) have recently been described to occur in patients with pulmonary alveolar microlithiasis (13, 14). These mutations were predicted to affect translation, potentially resulting in various altered gene products including, expression of truncated proteins or proteins with amino acid substitutions, and aberrant splicing or inability to express the protein. Several of those aberrant translations resulted in a functional loss of the NaPi2b protein, when expressed as recombinant protein in-vitro. Since SLC34A2 is apparently the only known phosphate transporter highly expressed in the lung, inactivating mutations of the SLC34A2 gene were associated with accumulations of calcium phosphate microliths in the alveolar space and SLC34A2 has been reported to be the causative gene for pulmonary alveolar microlithiasis in two independent studies (13, 14). We now have initiated a mutational analysis of the SLC34A2 gene in various MX35 antigen-expressing cancer types, including ovarian, lung and kidney cancer, to investigate if mutated forms of the gene may also be present in cancer in certain tumor types.

The MX35 antibody, which we now have shown to recognize NaPi2b, had initially been developed against ovarian cancer and the antibody showed homogeneous reactivity with approximately 90% of human ovarian epithelial cancers but with only a limited number of normal tissues by immunohistochemistry. In frozen tissue sections, mAb MX35 reactivity was detected with epithelial cells of normal lung, bronchus, thyroid, uterus, cervix, Fallopian tube, sweat glands and the collecting ducts in the kidney (1). Although this tissue expression profile of MX35 on the protein level appears to correlates well with the gene expression profile reported for SLC34A2, the NaPi2b protein expression analysis in human tissue will need to be revisited with more advanced immunohistochemical methodologies. We have now embarked on a comprehensive study investigating NaPi2b tissue expression in normal human tissue and in a wide range of different human cancer types employing novel antigen retrieval techniques, which facilitate the reactivity of MX35 in archival material.

What are the prospects for NaPi2b as a target for antibody-based cancer therapies in humans? The main concern would be expression in normal tissue, particularly the lung. However, in the initial biodistribution/pharmacokinetics analysis of mAb MX35 in humans, there was good tumor localization with no evidence for accumulation in the lung or other normal tissues. From other studies with monoclonal antibody targeting in clinical trials "in-vitro" expression of antigen by immunohistochemistry does not necessarily predict antibody localization "in-vivo", and this is best explained by inaccessibility of antigen-expressing cells to blood-borne antibody. The other issue that needs to be addressed is the relative impact of this phosphate pump and other related SLC members in cancer cells compared to normal cells with regard to viability and proliferation. Resolving these questions of in-vivo accessibility and the role of these genes in cancer cells will be critical in determining the optimal therapeutic strategies for mAb MX35. With the identification of NaPi2b as the molecular target of mAb MX35 it became evident that the MX35 antigen is not only expressed in ovarian cancers but also in a series of other epithelial cancers, including lung cancer, thyroid cancer and renal cancer potentially expending the therapeutic application of the MX35 antibody to those and other types of cancer. NaPi2b is the first example of a phosphate transporter that can be targeted as cancer antigen with a monoclonal antibody. It is conceivable that also other members of the large solute transporter family, most of them like SLC34A2/NaPi2b under tight regulatory control become abnormally expressed in cancer, and thus turn into potential targets for immunotherapy of cancer with antibodies and vaccines.

REFERENCES

1. Mattes, M. J., Look, K., Furukawa, K., Pierce, V. K., Old, L. J., Lewis, J. L., Jr., and Lloyd, K. O. (1987) Mouse monoclonal antibodies to human epithelial differentiation antigens expressed on the surface of ovarian carcinoma ascites cells. *Cancer Res* 47, 6741-50. (PMID: 3677104)
2. Rubin, S. C., Kostakoglu, L., Divgi, C., Federici, M. G., Finstad, C. L., Lloyd, K. O., Larson, S. M., and Hoskins, W. J. (1993) Biodistribution and intraoperative evaluation of radiolabeled monoclonal antibody MX35 in patients with epithelial ovarian cancer. Gynecol Oncol 51, 61-6. (PMID: 8244176)
3. Finstad, C. L., Lloyd, K. O., Federici, M. G., Divgi, C., Venkatraman, E., Barakat, R. R., Finn, R. D., Larson, S. M., Hoskins, W. J., and Humm, J. L. (1997) Distribution of radiolabeled monoclonal antibody MX35 F(ab')2 in tissue samples by storage phosphor screen image analysis: evaluation of antibody localization to micrometastatic disease in epithelial ovarian cancer. *Clin Cancer Res* 3, 1433-42. (PMID: 9815829)
4. Back, T., Andersson, H., Divgi, C. R., Hultbom, R., Jensen, H., Lindegren, S., Palm, S., and Jacobsson, L. (2005) 211At radioimmunotherapy of subcutaneous human ovarian cancer xenografts: evaluation of relative biologic effectiveness of an alpha-emitter in vivo. *J Nucl Med* 46, 2061-7. (PMID: 16330571)
5. Elgqvist, J., Andersson, H., Back, T., Claesson, I., Hultbom, R., Jensen, H., Lindegren, S., Olsson, M., Palm, S., Warnhammar, E., and Jacobsson, L. (2006) Fractionated radioimmunotherapy of intraperitoneally growing ovarian cancer in nude mice with 211At-MX35 F(ab')2: therapeutic efficacy and myelotoxicity. *Nuclear Med Biol* 33, 1065-72. (PMID: 17127181)
6. Hultborn R, A. H., Bäck T, Divgi C, Elgqvist J, Himmelman J, Horvath G, Jensen H, Lindegren S, Palm S, Jacobsson L (2006) Pharmacokinetics and dosimetry of 211at-MX35 F(ab')2 in therapy of ovarian cancer—preliminary results from an ongoing phase I study [abstract]. *Cancer Biother Radiopharm* 21, 373-81.
7. Welshinger, M., Yin, B. W., and Lloyd, K. O. (1997) Initial immunochemical characterization of MX35 ovarian cancer antigen. *Gynecol Oncol* 67, 188-192
8. Feild, J. A., Zhang, L., Brun, K. A., Brooks, D. P., and Edwards, R. M. (1999) Cloning and functional characterization of a sodium-dependent phosphate transporter expressed in human lung and small intestine. *Biochem Biophys Res Commun* 258, 578-82. (PMID: 10329428)
9. Xu, H., Bai, L., Collins, J. F., and Ghishan, F. K. (1999) Molecular cloning, functional characterization, tissue distribution, and chromosomal localization of a human, small intestinal sodium-phosphate (Na+-Pi) transporter (SLC34A2). *Genomics* 62, 281-4. (PMID: 10610722)
10. Murer, H., Forster, I., and Biber, J. (2004) The sodium phosphate cotransporter family SLC34. *Pflugers Arch* 447, 763-7. (PMID: 12750889)
11. Forster, I. C., Hernando, N., Biber, J., and Murer, H. (2006) Proximal tubular handling of phosphate: A molecular perspective. *Kidney Intl* 70, 1548-59. (PMID: 16955105)
12. Traebert, M., Hattenhauer, O., Murer, H., Kaissling, B., and Biber, J. (1999) Expression of type II Na—P(i) cotransporter in alveolar type II cells. *Am J Physiol* 277, L868-73. (PMID: 10564169)
13. Huqun, Izumi, S., Miyazawa, H., Ishii, K., Uchiyama, B., Ishida, T., Tanaka, S., Tazawa, R., Fukuyama, S., Tanaka, T., Nagai, Y., Yokote, A., Takahashi, H., Fukushima, T., Kobayashi, K., Chiba, H., Nagata, M., Sakamoto, S., Nakata, K., Takebayashi, Y., Shimizu, Y., Kaneko, K., Shimizu, M., Kanazawa, M., Abe, S., Inoue, Y., Takenoshita, S., Yoshimura, K., Kudo, K., Tachibana, T., Nukiwa, T., and Hagiwara, K. (2007) Mutations in the SLC34A2 gene are associated with pulmonary alveolar microlithiasis. *Am J Respi Crit. Care Med* 175, 263-8. (PMID: 17095743)
14. Corut, A., Senyigit, A., Ugur, S. A., Altin, S., Ozcelik, U., Calisir, H., Yildirim, Z., Gocmen, A., and Tolun, A. (2006) Mutations in SLC34A2 cause pulmonary alveolar microlithiasis and are possibly associated with testicular microlithiasis. *Am J Hum Genet.* 79, 650-6. (PMID: 16960801)
15. Rangel, L. B., Sherman-Baust, C. A., Wernyj, R. P., Schwartz, D. R., Cho, K. R., and Morin, P. J. (2003) Characterization of novel human ovarian cancer-specific transcripts (HOSTs) identified by serial analysis of gene expression. *Oncogene* 22, 7225-32. (PMID: 14562052)
16. Jarzab, B., Wiench, M., Fujarewicz, K., Simek, K., Jarzab, M., Oczko-Wojciechowska, M., Wloch, J., Czarniecka, A., Chmielik, E., Lange, D., Pawlaczek, A., Szpak, S., Gubala, E., and Swierniak, A. (2005) Gene expression profile of papillary thyroid cancer: sources of variability and diagnostic implications. *Cancer Res* 65, 1587-97. (PMID: 15735049)
17. Xu, H., Uno, J. K., Inouye, M., Xu, L., Drees, J. B., Collins, J. F., and Ghishan, F. K. (2003) Regulation of intestinal NaPi-IIb cotransporter gene expression by estrogen. *Am J Physiol* 285, G1317-24. (PMID: 12893629)
18. Matsuo, A., Negoro, T., Seo, T., Kitao, Y., Shindo, M., Segawa, H., and Miyamoto, K. (2005) Inhibitory effect of JTP-59557, a new triazole derivative, on intestinal phosphate transport in vitro and in vivo. *Eur J Pharmacol* 517, 111-9. (PMID: 15961073)
19. Yin, B. W., and Lloyd, K. O. (2001) Molecular cloning of the CA125 ovarian cancer antigen: identification as a new mucin, MUC16. *J Biol Chem* 276, 27371-5. (PMID: 11369781)
20. Yin, B. W., Finstad, C. L., Kitamura, K., Federici, M. G., Welshinger, M., Kudryashov, V., Hoskins, W. J., Welt, S., and Lloyd, K. O. (1996) Serological and immunochemical analysis of Lewis y (Ley) blood group antigen expression in epithelial ovarian cancer. *Int J Cancer* 65, 406-12. (PMID: 8621218)
21. Ritter, G., Cohen, L. S., Nice, E. C., Catimel, B., Burgess, A. W., Moritz, R. L., Ji, H., Heath, J. K., White, S. J., Welt, S., Old, L. J., and Simpson, R. J. (1997) Characterization of posttranslational modifications of human A33 antigen, a novel palmitoylated surface glycoprotein of human gastrointestinal epithelium. *Biochem Biophys Res Commun* 236, 682-6. (PMID: 9245713)
22. Iwahana, H., Yakymovych, I., Dubrovska, A., Hellman, U., and Souchelnytskyi, S. (2006) Glycoproteome profiling of transforming growth factor-beta (TGFbeta) signaling: nonglycosylated cell death-inducing DFF-like effector A inhibits TGFbeta1-dependent apoptosis. *Proteomics* 6, 6168-80. (PMID:17080483)
23. Peters, E. C., Horn, D. M., Tully, D. C., and Brock, A. (2001) A novel multifunctional labeling reagent for enhanced protein characterization with mass spectrometry. *Rapid Commun Mass Spectrom* 15, 2387-92. (PMID: 11746907)
24. Gure, A. O., Chua, R., Williamson, B., Gonen, M., Ferrera, C. A., Gnjatic, S., Ritter, G., Simpson, A. J., Chen, Y. T., Old, L. J., and Altorki, N. K. (2005) Cancer-testis genes are coordinately expressed and are markers of poor outcome in non-small cell lung cancer. *Clin Cancer Res* 11, 8055-62. (PMID: 16299236)
25. Pfreundschuh, M., Shiku, H., Takahashi, T., Ueda, R., Ransohoff, J., Oettgen, H. F., and Old, L. J. (1978) Serological analysis of cell surface antigens of malignant human brain tumors. *Proc Natl Acad Sci USA* 75, 5122-6. (PMID: 283420)

EXAMPLE 2

The nucleotide and polypeptide sequence of the mouse MX35 antibody has now been determined. The heavy chain variable region sequence is provided in FIG. 5. The heavy chain variable region sequence includes the sequences of the three CDR domains, CDR1 (GYTFTGYNIH), CDR2 (AIYPGNGDTSYKQKFRG) and CDR3 (GETARATFAY). The light chain variable region sequence is provided in FIG. 6. The light chain variable region sequence includes the sequences of the three CDR domains, CDR1 (SASQDIGNFLN), CDR2 (YTSSLYS) and CDR3 (QQYSKLPLT).

EXAMPLE 3

Development of Monoclonal Antibodies Specific Towards Sodium-Dependent Phosphate Co-Transporter NaPi2b The homeostasis of inorganic phosphate in human body is maintained by regulated absorption, metabolism and excretion. Sodium-dependent phosphate transporters (NaPi) mediate the transport of inorganic phosphate ($P_i$) inside of cells in response to dietary phosphate consumption, hormones, and growth factors. NaPi2b is a member of sodium-dependent phosphate transporters family with a distinct pattern of expression and regulation. Signaling pathways activated by mitogens, glucocorticoids and metabolic factors have been implicated in regulating $P_i$ transport via NaP2b. Inactivation of NaPi2b function by mutations has been linked to human pathologies, such pulmonary alveolar microlithiasis. In this study, we describe the production and characterization of monoclonal antibodies directed against NaPi2b. Generated antibodies were shown to recognize specifically transiently overexpressed and endogenous NaPi2b in commonly used immunoassays, such as Western blotting, immunoprecipitation and immunohistochemistry. These properties make them particularly valuable for elucidating NaPi2b function in health and disease.

Introduction

Cellular concentration of inorganic phosphate (P) should be maintained constant for proper regulation of growth, metabolism and signaling pathways, as well as for bone formation. Inorganic phosphate homeostasis is maintained by various mechanisms, mainly through the regulation of its absorption and metabolism. Cellular intake of P, is mediated by sodium dependent phosphate transporters (belong to solute carrier series, SLC) which could be grouped into three subtypes based on sequence identity: NaPi-I (SLC17), NaPi-II (SLC34) and NaPi-III (SLC20). NaPi2b (NaPi-IIb, SLC34A2, NaPi3b, NPT-2) belongs to type II family of sodium-dependent phosphate transporters which also includes NaPi2a (NaPi-IIa) and NaPi2b (NaPi-IIc). Type II Na/Pi cotransporters are expressed in various tissues and play a major role in the homeostasis of inorganic phosphate. NaPi2b was identified by two independent laboratories by employing bioinformatic homology screens (1, 2). NaPi2b is a transmembrane protein that is anchored to the cellular membranes through at least 8 highly hydrophobic □-helical regions. In the predicted topology of NaPi2b, both N- and C-terminal tails face the cytoplasm, exposing various length loops to the extracellular and intracellular compartments. The largest extracellular loop contains several potential sites of glycosylation and a region rich in cysteine residues which might be involved in disulfide bond formation. On the SDS-PAGE gel, NaPi2b runs as a diffused band of approximately 95-108 kDa (3). Furthermore, NaPi2b can also exist as a dimer (4). Expression studies indicated that NaPi2b is expressed in small intestine, lung, testis, liver, ovary, secreting mammary glands, salivary glands and osteoblasts (1, 5-9). The level of NaPi2b was found to be controlled by many hormones and metabolic factors according to the body's P, needs. It has been reported that the increased level NaPi2b is induced by low phosphate diet, vitamin D, estrogens (10, 11,). Downregulation of NaPi2b level in response to FGF 23, EGF and glucocorticoids was demonstrated in cellular models (12, 13, and 14). In addition, Pi and carbonate are known to buffer protons in blood during metabolic acidosis. To serve in proton buffering, Pi is released from bone together with carbonate or replenished by NaPi2b intestinal absorption (15). Immunohistochemical studies showed that NaPi2b is localised mainly in brush borders of enterocytes or in apical membranes of mammary epithelial cells (2,16). NaPi2b transports divalent P, together with three Na$^+$ ions by electrogenic mechanism. Signaling pathways which regulate the function of NaPi2b are not well understood. Recently, the ability of the serum and glucocorticoid inducible kinase (SGK1) to stimulate phosphate transport via NaPi2b was demonstrated (17). Furthermore, the activity of NaPi2b was shown to be inhibited by rapamycin, indicating the involvement of mTor signalling pathway in the regulation of phosphate homeostasis (18).

Deregulation of NaPi2b function has been linked to human pathologies. It has been recently demonstrated that mutations in NaPi2b cause pulmonary alveolar microlithiasis (19). Furthermore, the overexpression of NaPi2b was observed in ovarian, breast and papillary thyroid tumors (20, 21, 22). Further link of NaPi2b to cancer has been recently established. The consortium led by the Ludwig Institute for Cancer Research identified NaPi2b as MX35 cancer antigen, which has been associated with ovarian cancer for many years (23).

In this study, we describe the production and characterization of monoclonal antibodies specific towards NaPi2b. A fragment of NaPi2b was expressed in bacteria as GST fusion protein and used for immunization and screening procedures. Several rounds of screening allowed us to select two monoclonal antibodies, termed L2(20/3) and L3(28/1), which recognize specifically endogenous NaPi2b in various immunological assays, including Western blotting, immunoprecipitation and immunohistochemistry. Generated and characterized antibodies would be useful and available for academic community to study the function of NaPi2b.

Materials and Methods

Cell Lines.

All cell lines were obtained from the cell bank of the Ludwig Institute for Cancer Research, New York Branch at Memorial Sloan-Kettering Cancer Center.

Production and Purification of GST-NaPi2b Fusion Protein.

The extracellular domain (loop) of human NaPi2b (L, loop, 188-361aa) and various fragments of this domain (1L, 188-300aa; 2L 291-361aa; 3L, 291-340aa; 4L, 311-340aa; 5L, 311-361aa) were PCR amplified using specific oligonucleotide primers with BamHI and EcoRI restriction sites and cloned into pGEX4T1 vector (Novagen) in frame with the C-terminal GST-tag sequence. The resulting constructs, designated as pGEX-4T1-NaPi2b-L, pGEX-4T1-NaPi2b-1L, pGEX-4T1-NaPi2b-2L, pGEX-4T1-NaPi2b-3L, pGEX-4T1-NaPi2b-4L, pGEX-4T1-NaPi2b-5L were transformed into BL21(DE3) *E. coli* strain cells. The expression of recombinant proteins were induced with 1 mM iso-propyl-b-D(2)-thiogalactopyranoside (IPTG) for 1-3 h at 30° C. Purification of GST-NaPi2b recombinant proteins from the soluble fraction of bacterial lysate was carried out using GST Agarose (Qiagen, UK) according to the manufacturer's recommendations. Purification of GST-NaPi2b-L from the insoluble fraction was performed out using electro-elution from the gel.

Production of Hybridoma Cells.

6-8 weeks old female BALB/c mice were immunized by intraperitoneal injection (i.p.) with 15 μg of recombinant GST-NaPi2b-L(188-361 aa) fusion protein in complete Freund's adjuvant 4 times in two weeks interval. Then, immunized mice (with serum titer no less than $10^{-5}$-$10^{-6}$) were boosted with 20 μg of antigen in PBS by i.p. injection. Three day later splenocytes from immunized mice were fused in the presence of PEG (MW2000, Merck, Germany) with SP2/0 myeloma cells cultured in RPMI 1640 medium containing 20% fetal calf serum (FCS). Primary screening of hybridoma supernatants was performed using ELISA technique and isolated positive clones were subcloned by limiting dilution method using GST-NaPi2b-L as antigen (24).

Western Blot Analysis of Recombinant Proteins.

For hybridoma screening bacterially expressed GST-NaPi2b recombinant proteins: GST-NaPi2b-L 188-361aa, or GST-NaPi2b-1L 188-300 aa, or GST-NaPi2b-2L 291-361aa were separated by a 10% SDS/PAGE and electrotransferred to Immobilon-P membrane (Millipore, USA). The membrane was blocked by 5% nonfat milk in PBS, containing 0.1% Tween 20 (PBST) for 1 h at room temperature and divided into strips followed by a single wash with PBST. Strips were incubated with PBS, post-immune serum (1:1000), hybridoma media from positive clones, or cell culture media alone for 2 h at room temperature. Peroxidase-conjugated secondary antibody (Promega, USA) was added to the strips after three washes and incubated for 1 h at room temperature.

Strips were washed three times, and the immunoreactivity was detected by ECL system (Amersham, Sweden).

For mAbs epitope mapping recombinant peptides (GST-NaPi2b-L, GST-NaPi2b-1L, GST-NaPi2b-2L, GST-NaPi2b-3L, GST-NaPi2b-4L, GST-NaPi2b-5L) have been analysed in WB as described above and incubated with L2(2/1), L2(20/3) and L3(28/1) mAbs. Anti-GST mAbs were used as a control for recombinant proteins expression.

Purification of mAbs.

BALB/c mice were injected with 0.5 ml of pristane and 7-10 days later inoculated with $5 \cdot 10^6$ of hybridoma cells (18). The ascitic fluid was collected after 7-10 days, and after centrifugation for at 14000 rpm, 20 min and filtration by 0.4 μm filter (Millipore, USA) used for affinity purification by Protein A-Sepharose CL-4B (Amersham, Sweden) chromatography. The IgG fractions were pulled together and dialyzed in a phosphate-buffered saline (PBS), pH 7.4. The aliquots of purified antibodies were stored at −20° C.

Cell Lysate Preparation and Immunoblotting.

OVCAR3, SK-RC-18, SK-RC-01 cells were lysed in buffer containing 10 mM Tris-HCl, pH 7.5, 150 mM NaCl, 10 mM $MgCL_2$, 0.5% NP-40,) and a mixture of Halt Protease Inhibitor Cocktail (Pierce). Protein concentration was estimated by BSA assay (Pierce), and equal amounts of proteins (10 μg) were resolved in 8% SDS-PAGE. Gels were transferred to polyvinylidene difluoride (PVDF) membrane (Millipore, USA). The membrane was blocked with 5% BSA in 1×PBST for 1 h at RT. Anti-NaPi2b mAbs were incubated with membranes at 4° C. overnight. After washing with PBST, HRP-conjugated goat anti-mouse IgG 1:5000 (Promega, USA) was added to the membrane for 1 h at RT. Western blots were developed using the ECL system (Amersham, Sweden) and then exposed to Agfa X-ray film.

Immunohistochemical Analysis.

Anti-NaPi2b mAbs were used for immunohistochemical analysis of ovarian cancer samples according to a standard protocol. Briefly, representative sections of ovarian tumors were prepared from paraffin blocks. Endogenous peroxidase was quenched with $H_2O_2$ (3%) in 0.01% PBS. After blocking non-specific staining with avidin-biotin blocking solution (Vector Laboratories, Burlinghame, Calif., USA), tissue sections were incubated overnight at 4° C. with anti-NaPi2b mAb (10 mkg/ml). Then sections were incubated with biotinylated secondary antibodies for 2 hours at room temperature (1:400, goat anti-mouse biotinylated IgG, Sigma), followed by incubation with avidin-biotin-peroxidase complex (Vector Laboratories, Burlinghame, Calif., USA; 30 min, room temperature) and developed with diaminobenzidine solution. Haematoxylin was used for counterstaining. Standard microscopy was performed using a Zeiss Universal microscope (Zeiss, Germany), and images were captured using digital Axiocam software.

Transient Transfection of Hek293 Cells.

Transfection of Hek293 cells was performed with FuGene transfection reagent (Roshe, Switzerland) according to manufacture's instruction. Briefly, for each transfection 5 mkg of plasmid DNA (pcDNA3.1/Glu-Napi2b or empty vector) and 10 mkl of FuGene was used. After 48 h incubation cells were lysed and analysed.

Immunoprecipitation.

25 μl of 50% suspension of Protein A-Sepharose CL-4B (Amersham, Sweden) was incubated with hybridoma media from selected positive clones for 1 h at 4° C. at rotation and then analysed by lysis buffer. Supernatants (500 μg of total protein) from Hek 293 cells transfected with pcDNA3.1/NaPi2b or pcDNA3.1 alone were added to beads. After incubation on the wheel at 4° C. for 3 h, beads were washed four times with 1 ml of lysis buffer as described above. Beads were boiled in Laemmli sample buffer and immune complexes were separated by 8% SDS-PAGE for further immunoblotting or Coomassie staining.

Mixed Hemadsorption Assays.

The mixed hemadsorption assay (MHA), which detects surface-bound IgG by adherence of rabbit anti-mouse IgG coated human red blood cells (blood group j) to target cells, was performed as described (25).

Isotype Antibody Detection.

Isotypes of antibodies were defined with mouse monoclonal isotyping test kit (AbD Serotec, UK) using cultures supernatants of KL2(2/1), KL2(20/3), KL3 (28/1) clones.

Results and Discussion

Membrane transport of Pi by NaPi cotransporters is recognized as a key regulatory event in maintaining phosphate homeostasis in organisms as diverse as bacteria and human. Phosphate transporter NaPi2b is responsible for mediating of epithelial Pi transport in several human tissues. Deregulation of NaPi2b function has been link to pulmonary alveolar microlithiasis. Recently overexpression of NaPi2b in breast, thyroid and ovarian cancer has been established. The mechanism and the importance of NaPi2b overexpression in human tumors, especially ovarian cancer, are not known. These findings identify NaPi2b as a suitable candidate for the development of novel diagnostic and therapeutic interventions in human pathologies.

Figure 1B:
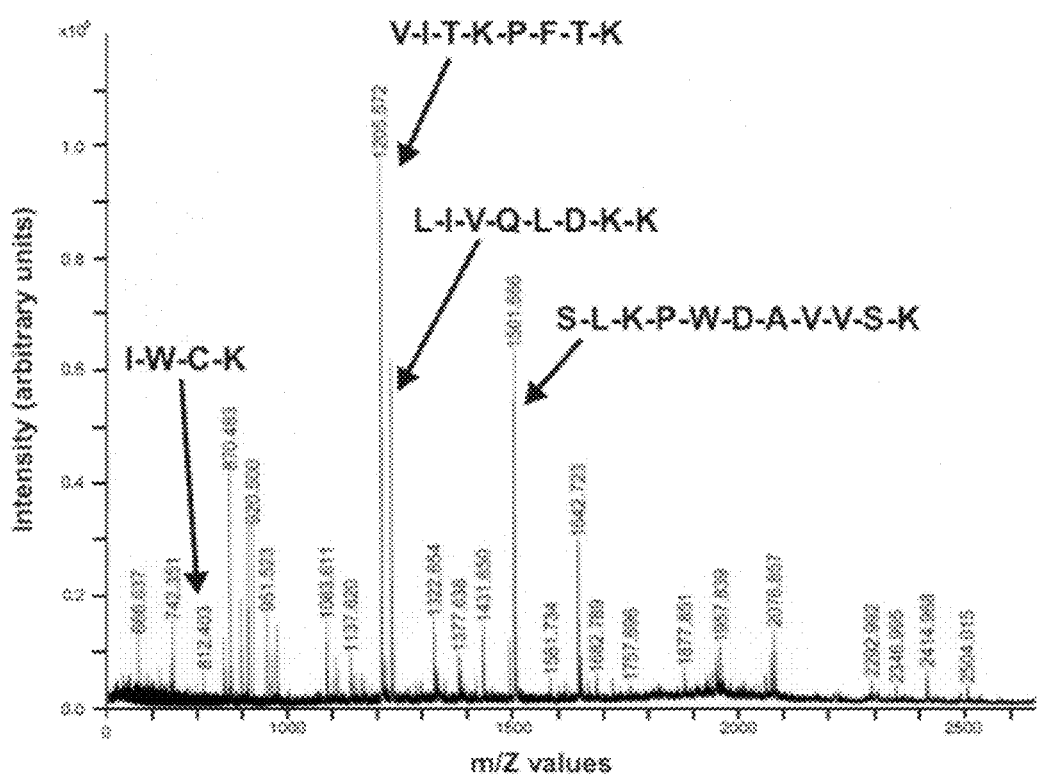

The main focus of this study was to generate monoclonal antibodies which can specifically recognize NaPi2b in various immunological assays, including Western blotting, immunoprecipitation and immunohistochemistry. In order to obtain the antibody which can have the epitope in the extracellular region of NaPi2b, we selected the largest extracellular loop (188-361aa) for expression studies and immunization. The fragment of NaPi2b, corresponding to amino residues 188-361 was amplified by PCR and cloned into pGEX4T1 vector in frame with the N-terminally located GST sequence. The expression of the fusion protein from the resulting plasmid pGEX4T1/NaPi2b-L was carried out in BL21 (DE3) cells. Expression analysis indicated that GST/NaPi2b-L was expressed at a very high level after induction with IPTG. However, the fusion protein was insoluble and unstable (FIG. 1A). Our attempts to increase the solubility of the GST/NaPi2b-L protein by changing the conditions of expression were not successful. Therefore, the purification of GST/NaPi2b-L was performed under denatured conditions from the insoluble fraction as described in Material and Methods. This approach allowed us to purify GST/NaPi2b-L fusion protein with at least 80% purity in quantities sufficient for immunization and ELISA screening (FIG. 1A). In addition, the N- and C-terminal regions of the largest extracellular loop were expressed in bacteria as GST fusion and designated as GST/NaPi2b-1L (188-300aa) and GST/NaPi2b-2L (291-361aa). As shown in FIGS. 1B and C, both fusion proteins expressed well, but were only partially soluble. Affinity purification on Glutathione Sepharose allowed us to obtain significant quantities of recombinant GST/NaPi2b-1L and GST/NaPi2b-2L of approximately 95% purity (FIGS. 1B, C).

Generation of hybridomas was performed by a standard procedure as described in Materials and Methods. Primary ELISA screening of hybridoma media from generated hybrids with GST/NaPi2b-L fusion protein led to the detection of 110 positive clones. In a second round screening, the specificity towards GST/NaPi2b-L was further confirmed for 83 selected clones. Subsequent ELISA screening against GST alone indicated that 27 clones possessed epitopes located in GST sequences of GST/NaPi2b-L.

The specificity of remaining 56 positive hybrid clones was examined by Western blotting towards GST/NaPi2b-L. This analysis identified 24 clones which recognized specifically, but with different efficiency, a 45 kDa band corresponding to GST/NaPi2b-L (data not shown). Positive clones that showed the strongest reactivity towards GST/NaPi2b-L were further tested by immunoblotting against GST/NaPi2b-1L and GST/NaPi2b-2L. Interestingly, none of the selected clones recognized the GST/NaPi2b-1L fusion protein (data not shown). This data clearly indicate that the C-terminal region of the NaPi2b extracellular loop is much more immunogenic than its N-terminal region. This finding correlates with bioinformatic analysis of NaPi2b immunogenicity (www.imtech.res.in/raghava/bcepred). The best responders (7 hybridoma clones) were subcloned to monoclonality and confirmed again by ELISA and Western blotting.

Figure 2:
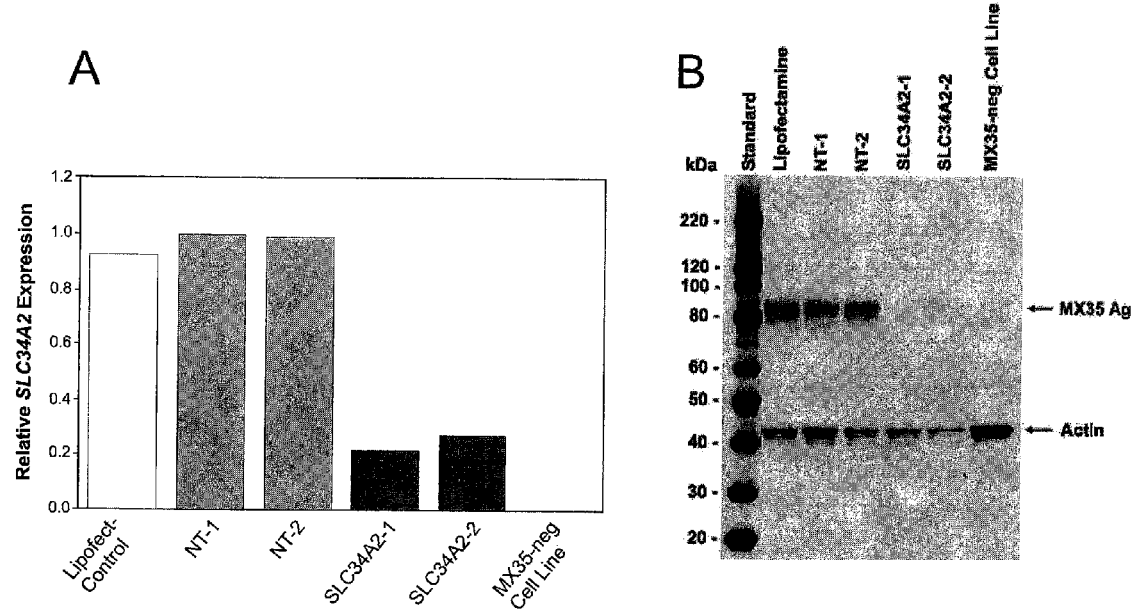
FIG. 2: Effects of siRNA interference on the level of SLC34A2 mRNA and MX35 protein expression in SK-RC-18 cells. Cells were transfected with SLC34A2 siRNA or control siRNA in the presence of Lipofectamine 2000. Cells were assayed 72 hours after transfection. (A) Total RNA was extracted and SLC34A2 mRNA levels were determined by real-time RT-PCR. (B) Cells were lysed and the level of protein expression was analyzed by SDS-PAGE and Western blotting using mAb MX35 and an anti-actin antibody.

To determine whether selected mAbs can recognize endogenous NaPi2b, we tested their specificity in Western blotting, immunoprecipitation, mixed hemadsorption assay and immunohystochemistry using mammalian cell lines and tissues. Initially, the lysates of NaPi2b positive (OVCAR3 and SK-RC-18) and negative (SK-RC-01) cell lines were probed in Western blotting with hybridoma medium from selected clones. All three cell lines have been typed previously by RT-PCR for the expression of SLC34A2 mRNA (23). This analysis allowed us to identify three clones which recognized specifically endogenous NaPi2b in immunoblotting. As shown in FIG. 2A, monoclonal antibodies termed L2(20/3), L3(28/1) and to the less extent L2(2/1) detect a diffuse band of approximately 95 kDa in OVCAR3 and SK-RC-18 cells, but not in SK-RC-01 cells under non-reduced conditions (FIG. 2, A). When total cell extracts were resolved under reduced conditions and probed with NaPi2b mAbs, the 95 kDa band of recognition of endogenously expressed NaPi2b in OVCAR3 and SK-RC-18 cells lysates was less diffuse and observed only with mAbs L2(20/3), L3(28/1) but not with mAb L2(2/1) (data not shown). These results indicate that all three monoclonal antibodies recognize conformational epitope(s) in the C-terminal region of the largest extracellular loop.

Then, we tested the ability of selected hybrid clones to immunoprecipitate transiently overexpressed NaPi2b. In this experiment, Hek293 cells were transiently transfected with pcDNA3.1/Glu-NaPi2b or pcDNA3.1 alone. We found that monoclonal antibodies L2(20/3) and L3(28/1) were particularly good in immunoprecipitating transiently overexpressed NaPi2b (FIG. 2 B). Furthermore, we found that both monoclonal antibodies L2(20/3) and L3(28/1) can specifically immunoprecipitate endogenous NaPi2b from SK-RC-18 cells (data not shown). We have tested monoclonal antibodies L2(20/3) and L3(28/1) in mixed hemadsorption assay where they showed strong reactivity with the cell lines OVCAR-3 and SK-RC-18, which expressed NaPi2b on their cell surface but did not react with SK-RC-1, which does not express NaPi2b (Table 3).

TABLE 3

Mixed hemadsorption assay of new monoclonal antibodies against Napi2b

| Antigen | Titer (ug mAb/ml) | | Secondary Ab |
|---|---|---|---|
| Cell line | L2(20/3) | L3(28/1) | Only |
| OVCAR-3 | 0.04 | 0.16 | negative |
| SK-RC-18 | 0.04 | 0.04 | negative |
| SK-RC-01 | negative | negative | negative |

The efficiency of generated antibodies was also examined by immunohistochemistry. Taking into account that NaPi2b overexpression was observed in human ovarian cancer, we probed the samples of normal ovary and ovarian carcinoma with generated monoclonal antibodies. The results presented in FIGS. 3A and B indicate that clones L2(20/3) and L3(28/1) recognize corresponding antigen in paraffin-embedded sections of ovarian carcinoma with positive staining localized mostly on the luminal edge of tumor sample. No or very little immunoreactive signal is detected in normal ovary under the same experimental conditions. These results supports previously published data indicating that NaPi2b is overexpressed in ovarian cancer (20).

To narrow down the epitopes of generated monoclonal antibodies we used a panel of GST/NaPi2b fusion constructs, expressing various regions of the largest extracellular loop. The schematic presentation of generated fusion proteins used in this study is shown in FIG. 4A. GST/NaPi2b fusion proteins and GST alone were resolved by SDS-PAGE under non-reduced conditions, transferred to the PVDF membrane and probed with L2(2/1), L2(20/3) and L3(28/1) mAbs. This study clearly indicated that the binding sites for all thee generated antibodies are located in the region between amino acid residues 311 and 340. FIG. 4B shows the epitope mapping for monoclonal antibody L2(20/3). Bioinformatic analysis confirmed this region as antigenic in NaPi2b sequence. Moreover, it also contains two cysteine residues (C322 and C328) which might be involved in disulfide bond formation. The presence of three potential sites of glycosylation (N313, N321 and N340) within the 311-340aa region has been also predicted by the bioinformatic analysis. Therefore, the pattern of glycosylation, as well as the formation of disulfide bridges, might determine the efficiency and the specificity of epitope's recognition in this highly antigenic region under physiological and pathological conditions.

Finally, we determined the isotypes of generated antibodies. By using Serotec's monoclonal antibody isotyping kit, we found that L2(2/1) and L3(28/1) clones produce IgG1, while L2(20/3) clone is IgG2b specific.

In summary, we have generated a panel of monoclonal antibodies against bacterially expressed extracellular domain of sodium-dependent phosphate transporter NaPi2b. Two hybrid clones, termed L2(20/3) and L3(28/1), recognize specifically and with high efficiency endogenous NaPi2b in various immunoassays, including Western blotting, immunoprecipitation and immunohistochemistry. The properties of both antibodies make them particularly useful for studying the function of NaPi2b under physiological and pathological conditions.

REFERENCES

1. Feild J A, Zhang L, Brun K A, Brooks D P, Edwards R M. Cloning and functional characterization of a sodium-dependent phosphate transporter expressed in human lung and small intestine. Biochem Biophys Res Commun. 1999; 258(3):578-82.
2. Xu H, Bai L, Collins J F, Ghishan F K. Molecular cloning, functional characterization, tissue distribution, and chromosomal localization of a human, small intestinal sodium-phosphate ($Na^+$-Pi) transporter (SLC34A2). Genomics 1999; 62(2):281-4.
3. Hilfiker H, Hattenhauer O, Traebert M, Forster I. Murer H, Biber J. Characterization of a new murine type II sodium-phosphate cotransporter expressed in mammalian small intestine. Proc Natl Acad Sci USA 1998; 95:14564-14569.
4. Forster I C, Hernando N, Biber J, Murer H, Proximal tubular handling of phosphate: A molecular perspective. Kidney International 2006; 70:1548-1559.

5. Traebert M, Hattenhauer O, Murer H, Kaissling B, Biber J. Expression of type II Na-P(i) cotransporter in alveolar type II cells. Am J Physiol 1999; 277:868-73.
6. Homann V, Rosin-Steiner S, Stratmann T, Arnold W H, Gaengler P, Kinne R K. Sodium-phosphate cotransporter in human salivary glands: molecular evidence for the involvement of NPT2b in acinar phosphate secretion and ductal phosphate reabsorption. Arch Oral Biol. 2005; 50(9):759-68.
7. Xu Y, Yeung C—H, Setiawan I, Avram C, Biber J, Wagenfeld A, Lang F, and Cooper T G. Sodium-Inorganic Phosphate Cotransporter NaPi2b in the Epididymis and Its Potential Role in Male Fertility Studied in a Transgenic Mouse Model. Biology of reproduction. 2003; 69:1135-1141.
8. Frei P, Gao B, Hagenbuch B, Mate A, Biber J, Murer H, Meier P J, Stieger B. Identification and localization of sodium-phosphate cotransporters in hepatocytes and cholangiocytes of rat liver. Am J Physiol Gastrointest Liver Physiol. 2005; 288:G771-G778.
9. Lundquist P, Murer H, Biber J. Type II $Na^+$-P cotransporters in osteoblast mineral formation; regulation by inorganic phosphate. Cell Physiol Biochem 2007; 19:43-56.
10. Katai K, Miyamoto K, Kishida S, Segawa H, Nii T, Tanaka H, Tani Y, Arai H, Tatsumi S, Morita K, Taketani Y, and Takeda E. Regulation of intestinal $Na^+$-dependent phosphate co-transporters by a low-phosphate diet and 1,25-dihydroxyvitamin D3. Biochem J 1999; 343:705-712.
11. Xu H, Uno J K, Inouye M, Xu L, Drees J B, Collins J F, and Ghishan F K. Regulation of intestinal NaPi2b cotransporter gene expression by estrogen. Am J Physiol Gastrointest Liver Physiol 2003; 285:G1317-61324.
12. Miyamoto K-I, Ito M, Kuwahata M, Kato S and Segawa H. Inhibition of intestinal sodium-dependent inorganic phosphate transport by fibroblast growth factor 23. Ther Apher Dial. 2005; 9 (4):331-5.
13. Xu H, Collins J F, Bai L, Kiela P R, Ghishan F K. Regulation of the human sodium-phosphate cotransporter NaPi2b gene promoter by epidermal growth factor. Am J Physiol 2001; 280:C628-C636.
14. Arima K, Hines E R, Kiela P R, Drees J B, Collins J F, Ghishan F K. Glucocorticoid regulation and glycosylation of mouse intestinal type IIb Na-Pi cotransporter during ontogeny. Am J Physiol 2002; 283:G426-G434.
15. Stauber A, Radanovic T, Stange G, Murer H, Wagner C A, Biber J. Regulation of intestinal phosphate transport. II. Metabolic acidosis stimulates Na(+)-dependent phosphate absorption and expression of the Na(+)—P(i) cotransporter NaPi2b in small intestine. Am J Physiol Gastrointest Liver Physiol. 2005; 288(3):G501-6.
16. Miyoshi K, Shillingford J M, Smith G H, Grimm S L, Wagner, K U, Oka T, Rosen J M, Robinson G W, Hennighausen L. Signal transducer and activator of transcription (Stat) 5 controls the proliferation and differentiation of mammary alveolar epithelium. J Cell Biol 2001; 155:531-542.
17. Palmada M, Dieter M, Speil A, Bohmer C, Mack A F, Wagner H J, Klingel K, Kandolf R, Murer H, Biber J, Closs E I and Lang F. Regulation of intestinal phosphate cotransporter NaPi IIb by ubiquitin ligase Nedd4-2 and by serum- and glucocorticoid-dependent kinase 1, Am. J. Physiol. Gastrointest. Liver Physiol. 2004; 287:G143-G150.
18. Shojaiefard M, Lang F. Stimulation of the intestinal phosphate transporter SLC34A2 by the protein kinase mTOR. Biochem Biophys Res Commun. 2006; 345(4):1611-4.
19. Corut A, Senyigit A, Ugur S A, Altin S, Ozcelik U, Calisir H, Yildirim Z, Gocmen A, Tolun A. Mutations in SLC34A2 cause pulmonary alveolar microlithiasis and are possibly associated with testicular microlithiasis. Am J Hum Genet. 2006; 79 (4):650-6.
20. Rangel L B, Sherman-Baust C A, Wernyj R P, Schwartz D R, Cho K R, Morin P J Characterization of novel human ovarian cancer-specific transcripts (HOSTs) identified by serial analysis of gene expression. Oncogene. 2003; 22(46):7225-32.
21. Blanchard A, Shiu R, Booth S, Sorensen G, DeCorby N, Nistor A, Wong P, Leygue E, Myal Y. Gene expression profiling of early involuting mammary glands reveals novel gene potentially relevant to human breast cancer. Frontiers in Bioscience 2007; 12:2221-32.
22. Jarzab B, Wiench M, Fujarewicz K, Simek K, Jarzab M, Oczko-Wojciechowska M, Wloch J, Czarniecka A, Chmielik E, Lange D, Pawlaczek A, Szpak S, Gubala E, Swierniak A. Gene expression profile of papillary thyroid cancer: sources of variability and diagnostic implications. Cancer Res. 2005; 65(4):1587-97.
23. Beatrice W. T. Yin, Ramziya Kiyamova, Ramon Chua, Otavia L. Caballero, Ivan Gout, Vitalina Gryshkova, Nimesh Bhaskaran, Serhiy Souchelnytskyi, Ulf Hellman, Valeriy Filonenko, Achim A. Jungbluth, Kunle Odunsi, Kenneth O. Lloyd, Lloyd J. Old, G. Ritter. Monoclonal antibody MX35 detects the membrane transporter NaPi2b (SLC34A2) in human carcinomas; a new target for cancer immunotherapy. Accepted for publication in cancer Immunity, MS No. 080103
24. Harlow, E. & Lane, D. Antibodies: A Laboratory Manual 1998; Cold Spring Harbor Lab. Press, Plainview, N.Y.
25. Pfreundschuh M, Shiku H, Takahashi T, Ueda R, Ransohoff J, Oettgen H F, Old L J. Serological analysis of cell surface antigens of malignant human brain tumors. Proceedings of the National Academy of Sciences of the United States of America. 1978; 75:5122-6.

EXAMPLE 4

Humanized MX35 (huMX35) Monoclonal Antibody

Design and Synthesis of Humanized MX35 (huMX25) Monoclonal Antibody:

The light and heavy chains variable regions of murine MX35 mAb were humanized in silico following veneering procedures as outlined by Dauherty et al. (U.S. Pat. No. 6,797,492 B2) and Gonzalez et al. (Tumour Biol., v. 26, n. 1, pp. 31-43, 2005), resulting in the nucleotide sequences set forth in SEQ ID NO: XX (humanized light chain variable region) and SEQ ID NO: YY (humanized heavy chain variable region). From these nucleotide sequences, the encoded light and heavy chains variable regions having, respectively, the amino acid sequences of SEQ ID NO: ZZ and PP may be expressed. FIG. 11 shows sequence alignment analysis (Clustal 2.0.1 program) between the humanized and murine light and heavy chain variable regions. The CDR regions of both light and heavy chains are boxed. The light chain CDRs of the humanized MX35 correspond to the CDRs of the mouse MX35 antibody and are set forth in SEQ ID NOs: 31-33. The heavy chain CDRs of the humanized MX35 correspond to the CDRs of the mouse MX35 antibody and are set forth in SEQ ID NOs: 26-28.

After the in silico veneering process, the Clustal alignment showed the lack of leader signal sequences for both heavy and light chains. To design the whole sequences, conserved peptide signals were searched and checked by virtual processing testing. The correct processing of the leader sequence was checked by the SignalP 3.0 Server algorithm (Center for Biological Sequence Analysis) available at the SignalP website.

The humanized MX35 antibody was constructed so as to have the murine heavy and light variable regions connected to the human constant regions IgG1 and kappa (Crucell, Netherlands), respectively. Several sequences of human IgG1 constant regions were analyzed, all displaying a high homology index and could also be used for the complete heavy chain construction. Restriction sites, HpaI for 3' ending and AscI for 5' ending of the light chain, NheI for 3' ending and BamHI for 5' ending of the heavy chain were added in the gene design in order to allow their efficient cloning in the vector pcDNA3002Neo (Jones et al, Biotechnol. Prog. V. 19, pp. 163-168, 2003) for expression in mammalian cells. The choice of the restriction enzymes was made to allow the cloning of the genes into the pcDNA3002Neo vector. Kozak consensus sequences were also added to allow adequate translation.

The exon sequences were optimized for human host cells taking into consideration the codons most used by human cells to synthesize proteins and so avoid low protein expression for the lack or shortage of specific codons available in the human species when using human cells as the expression system.

The final DNA sequence was analyzed by the software Genscan (MIT, USA), which predicts splicing sites at the exon-intron boundaries. The complete nucleotide sequences of both heavy and light chains were synthetically synthesized (GeneArt, Switzerland).

Cloning of Humanized MX35 Monoclonal Antibody:

The two vectors, each containing either the gene for light or heavy chain of the huMX35 were digested with the restriction enzymes (New England Biolabs) described above. The void pcDNA3002Neo vector (Crucell, Netherlands) was digested with the same enzymes so to receive the MX35 light and heavy chain genes, in a sequence order detailed below.

To check correctness, DNA sequencing of light and heavy antibody chains was performed by PCR cycle sequencing reactions with fluorescent dideoxy chain terminators (Big Dye® Terminator V3.1 Cycle Sequencing Kit, Applied Biosystems) according to the manufacturer's instructions. The sequencing reactions were analyzed on an ABI 3130 XL DNA Sequencer (Applied Biosystems).

For the cloning of the light chain of MX35 monoclonal antibody humanized version, the void pcDNA3002Neo vector and the transport vector containing the humanized MX35 light gene sequence were both cleaved with HpaI and AscI restriction enzymes (New England Biolabs) and analyzed by 1% agarosis gel electrophoresis. The void vector and the light chain fragment were both purified with Wizard SV Gel and PCR Clean-Up System (Promega) from the agarosis gel bands and used for ligation reaction with T4 DNA Ligase (Invitrogen) between the vector and the light chain gene. The product was used for bacteria transformation ("Heat Shock Transformation" described by Sambrook and Russell. (Molecular Cloning: A Laboratory Manual, Cold Spring Harbor Laboratory Press, 3$^{rd}$ edition, 2001)). Clones were amplified and analyzed by digestion with appropriate restriction enzymes confirming the expected insertion. The resulting clone containing the light chain of MX35 antibody was identified as pcDNA3002Neo-MX35-LC and used for the cloning of the humanized MX35 heavy chain. The transport vector containing the humanized MX35 heavy chain gene and the pcDNA3002Neo-MX35-LC were both cleaved with the restriction enzymes NheI and BamHI (New England Biolabs) at 3' and 5' endings respectively and the above protocol was used for cloning the humanized MX35 heavy chain gene into the pcDNA3002Neo-MX35-LC. After final analysis confirming the correct insertion, the final vector was identified by pcDNA3002Neo-MX35-LC-HC.

An endo-free maxi-prep kit (Endo-Free Plasmid Purification, Qyagen) was used for the extraction and purification of the vector pcDNA3002Neo-MX35-LC-HC containing the sequences of complete humanized MX35 gene. A similar procedure was used to purify the void pcDNA3002Neo vector meant for the Per.C6® cells transfection control. A complete DNA sequencing was carried out for both light and heavy chains of the humanized MX35, as described above, confirming the cloning precision. The nucleotide sequence for the light and heavy variable chains of the humanized MX35 are set forth in SEQ ID NOS: 34 and 36 and the amino acid sequence for the light and heavy variable chains of the humanized MX35 are set forth in SEQ ID NOS: 35 and 37.

Human Cell Transfection:

For the transfection, one vial of adherent Per.C6® frozen cells, passage 41 (Crucell, Netherlands), was thawed and maintained in culture medium DME-F12 (Invitrogen) supplemented with 10% fetal calf serum and 10 mM magnesium chloride, and allowed to expand. For the transfection, the cells were plated one day ahead in P60 petri dishes with 2×10E6 cells per dish. On the day of transfection the cells were 50% confluent. A mixture of DNA (2.5 µg), serum free medium culture with 10 mM $MgCl_2$, and 10 uL of Lipofectamine™ LTX solution (Invitrogen) was distributed in Eppendor® tubes. The tubes were maintained at room temperature for 30 min to allow the formation of liposome-DNA complexes.

The adherent cells were washed three times with serum free medium, with 2 mL of medium volume at the end of the washes. The mixture DNA-liposome was gently added over the medium with cells Per.C6® (Crucell, Netherlands). The plates were incubated and after 48 h a selection medium containing geneticin (G418) (Invitrogen) (500 µg/mL) was added with the objective of generate a stable pool. Every 3-4 days the medium was removed, centrifuged and kept frozen for further use. Fresh medium was added to the cells. This regimen lasted for over 30 days, when the cells were frozen with the label "Per.C6 huMX35 Pool 1". After 48 h a sample was taken for analysis. ELISA testing using separated heavy and light chain detection (Goat anti-human IgG (γ-chain specific) and goat anti-human kappa α-chain specific) (Southern Biotech) confirmed the synthesis of the humanized MX35 monoclonal antibody. Flow cytometry analysis confirmed that the produced antibody could bind to the cell line OVCAR-3, known by previous results (see prior examples) to be a positive cell for the murine version of MX35 monoclonal antibody.

With these positive results, this stable pool of adherent cells was then adapted to suspension growth in serum free medium (CDM4PerMab® medium, Hyclone, Thermo Scientific).

Production of Humanized MX35 Monoclonal Antibody:

A vial from the "Per.C6 huMX35 Pool 1" with cells producing humanized MX35 was thawed and the cells were expanded for suspension growth adaptation. Using a T-75 culture flask with 80% confluence, the cells were trypsinized, spun down, ressuspended in CDM4PerMab® medium (Hyclone, Thermo Scientific) without serum and kept in a T-75 flask in static culture conditions for 4 days. The cells in suspension were transferred to shaker flasks under orbital shaker conditions, with cell concentrations at least $0.6 \times 10^6$/ mL. The conditioned medium collected between medium changes was kept at temperature 4° C.-8° C.

Purification of the conditioned medium was performed in a cold room using a Hytrap® Protein A (GE Healthcare). The conditioned medium was filtered and diluted 1:1 with a buffer 1.5M glycine, 3M NaCl, pH 9.0. Ten column volumes of the diluted supernatant were applied onto the column. When the sample application was over, the column was washed with ten volumes of the above buffer. A buffer 50 mM citrate, 150 mM NaCl, pH 6.0 was used as first elution for the remotion of protein contaminants. The antibody was eluted with the buffer 50 mM citrate, 150 mM NaCl, pH3.0.

Material eluted from pH 6.0 and 3.0 were dialysed against phosphate buffered saline. Samples from each step of the protein A chromatography were applied onto SDS-PAGE gels, 7% for non-reduced electrophoresis and 12% for reduced electrophoresis. The antibody was eluted at pH 3.0 with no contaminants and the concentration was determined by Bradford method.

Binding Properties of Humanized MX35 Monoclonal Antibody:

The binding efficacy of humanized MX35 antibody, synthesized and purified as described above, was compared with the murine version of the MX35 antibody, using fluorescein isothiocyanate—FITC—marker to assess the specific binding to different cells lines in flow cytometry. The cell lines listed in TABLE 4 were trypsinized, adjusted to a concentration of $2.5 \times 10^5$ cells and distributed in 1.5 mL test tubes. After centrifugation the pellet was resuspended in 100 uL of primary antibody (either murine MX35, humanized MX35, hu3S193 or Zenapax®) diluted in the same culture medium used to cultivate the cells in the concentration of 20 µg/ml. In the case of controls "cells only" and FITC-conjugates, the cells were resuspended in 100 µL of medium culture. The mixtures were incubated for 1 h at 4° C. and then washed twice with 200 µL of phosphate buffered saline. The cells were resuspended in 100 µL of secondary antibody-FITC conjugated, either murine or human depending on the MX35 antibody version used. The control "cells only" tube received medium culture only. The secondary antibody FITC-conjugates were "anti-mouse IgG (whole molecule) F(ab')$_2$ fragment produced in sheep" and "anti-human IgG (γ-chain specific) F(ab')$_2$ fragment produced in goat", both from Sigma Aldrich. The mixtures of cells-FITC conjugates were incubated for 30 min at 4° C. and then washed twice with phosphate buffered saline. The pelleted cells were resuspended in 300 µL of fixation solution (glucose 3.2%, formaldehyde 1% in phosphate buffered saline). Staining of the cells with the fluorescent probes was measured in a fluid stream in the flow cytometry Guava® ExpressPro (Guava EasyCyte Mini System). For each individual experiment 10,000 events were acquired and counted. Built-in equipment software was used to analyze the results, with certain exemplary results presented in FIGS. 12 to 15.

TABLES 4 and 5 summarize the results of cytometry analysis of different cell lines with either humanized or murine MX35 antibody. The results of human tumor origin cells are tabulated in TABLE 4. The results of normal cells, human and rhesus monkey are tabulated in TABLE 5.

Besides the humanized and murine antibodies, the flow cytometry analyses utilized and depict two other humanized antibodies. One (hu3S193) targets the Lewis$^Y$ antigen, present in a great number of human epithelial carcinomas, and herein used as a positive control. A commercial humanized IgG1 antibody (Zenapax®, Roche) that targets the high affinity form of IL-2Rα present only on the membrane of activated lymphocytes was chosen as a paired negative control.

The overall results obtained by flow cytometry analyses confirmed the specificity of MX35 antibody binding to ovarian and renal human tumor cells. The MX35 antibodies, each and both mouse and human, did not show detectable binding by flow cytometry with various other cancer cell lines, DLD-1 cells from colorectal carcinoma, H358 cells from lung carcinoma, LNCaP cells from prostate carcinoma, MCF-7 cells from breast carcinoma, SK-MEL-28 cells from melanoma, MKN45 cells from gastric carcinoma, HeLa cells from cervical carcinoma. These cells were cell lines and not primary cancer or tumor cells. The humanized version of MX35 antibody followed the same profile shown by the original murine version of MX35 antibody. As the murine version has been already in Phase I clinical trials (cited references), the humanized version of MX35, having the same binding properties to the cell surface antigen, may be useful in clinical intervention against ovarian cancer.

TABLE 4

Results of huMX35 antibody binding to human tumor cells from different origins

| TUMOR CELL LINES | Cancer TISSUE SOURCE | Human MX35 BINDING | Mouse MX35 antibody |
|---|---|---|---|
| SK-RC-18 | Kidney | Positive | Positive |
| OVCAR-3 | Ovary | Positive | Positive |
| SW626 | Ovary (metastasis) Primary tumor: colon | Negative | Negative |
| LoVo | Colon | Negative | Negative |
| DLD-1 | Colon | Negative | Negative |
| H358 | Lung | Negative | Negative |
| LNCaP | Prostate | Negative | Negative |
| MCF-7 | Breast | Negative | Negative |
| SK-MEL-28 | Skin | Negative | Negative |
| MKN45 | Stomach | Negative | Negative |
| HeLa | Cervix | Negative | Negative |

TABLE 5

Results of MX35 binding to normal cells from different origins (3 human and 1 primate)

| NORMAL CELL LINES | Normal TISSUE SOURCE | Human MX35 BINDING | Mouse MX35 antibody |
|---|---|---|---|
| HEK 293 | Kidney | Negative | Negative |
| LLC-MK2 | Kidney (Rhesus) | Negative | Negative |
| MRC-5 | Lung | Negative | Negative |
| PER.C6 | Retina | Negative | Negative |

REFERENCES

Daugherty et al. Method for reducing the immunogenicity of antibody variable domains. U.S. Pat. No. 6,797,492 B2; Sep. 28, 2004.

Gonzalez, N. R. et al. "Minimizing the immunogenicity of antibodies for clinical application". Tumour Biol., 26(1): 31-43, 2005.

Rubin S C, K J A Kairemo, A L Brownell, F Daghighian, M G Federici, Kans. Pentlow, R D Finn, R M Lambrecht, W J Hoskins, J L Lewis & S M Larson. High-resolution positron emission tomography of human ovarian cancer in nude rats using $^{124}$I-labeled monoclonal antibodies. Gynecol. Oncol. 1993; 48: 61-67.

Rubin S C, L Kostakoglu, C Divgi, M G Federici, C L Finstad, K O Lloyd, S M Larson & W J Hoskins. Biodistribution and intraoperative evaluation of radiolabeled monoclonal antibody MX35 in patients with epithelial ovarian cancer. Gynecol. Oncol. 1993; 51: 61-66.

Finstad C L, K O Lloyd, M G Federici, C Divgi, E Venkatraman, R R Barakat, R D Finn, S M Larson, W J Hoskins & J L Humm. Distribution of radiolabeled monoclonal antibody MX35 F(AB')$_2$ in tissue samples by storage phosphor screen image analysis: Evaluation of antibody localization to micrometastatic disease in epithelial ovarian cancer. Clin. Cancer Res. 1997; 3: 1433-1442. Elgqvist J, Andersson H, Bäck T, Hultborn R, Jensen H, Karlsson B, Lindegren S, Palm S, Warnhammar E & Jacobsson L. Therapeutic efficacy and tumor dose estimations in radioimmunotherapy of intraperitoneally growing OVCAR-3 cells in nude mice with $^{211}$At-labeled monoclonal antibody MX35. J Nucl Med 2005; 46:1907-1915.

Bäck T, Andersson H, Divgi C R, Hultborn R, Jensen H, Lindegren S, Palm S & Jacobsson L. $^{211}$At radioimmunotherapy of subcutaneous human ovarian cancer xenografts: Evaluation of relative biological effectiveness of an α-emitter in vivo. J Nucl Med 2005; 46:2061-2067.

Elqqvist J, Andersson H, Bäck T, Claesson I, Hultborn R, Jensen J, Lindegren S, Olsson M, Palm S, Warnhammar E & Jacobsson L. Fractioned radioimmunotherapy of intraperitoneally growing ovarian cancer in nude mice with $^{211}$At-MX35 F(ab')$_2$: therapeutic efficacy and mielotoxicity. Nuclear Med Biol 2006; 33:1065-1072.

Elqqvist J, Andersson H, Bäck T, Claesson I, Hultborn R, Jensen J, Johansson B, Lindegren S, Olsson M, Palm S, Warnhammar E & Jacobsson L. α-radioimmunotherapy of intraperitoneally growing OVCAR-3 tumors of variable dimensions: outcome related to measured tumor size and mean absorbed dose. J Nucl Med 2006; 47:1342-1350.

Elgqvist J, Andersson H, Bernhardt P, Bäck T, Claesson I, Hultborn R, Jensen H, Johansson B, Lindegren S, Olsson M, Palm S, Warnhammar E & Jacobsson L. Administered activity and metastatic cure probability during radioimmunotherapy of ovarian cancer in nude mice with $^{211}$At-MX35 F(ab')$_2$. Int. J. Radiation Oncology Biol. Phys. 2006; 66(4):1228-1237.

Howard M. Shapiro. Practical Flow Cytometry. 4th Edition, 2003. Jones et al. High-level expression of recombinant IgG in the human cell line per.c6. Biotechnol. Prog. V. 19, pp. 163-169, 2003.

Sambrook, J. and Russell, D. W. Molecular Cloning: A Laboratory Manual, Cold Spring Harbor Laboratory Press, 3$^{rd}$ edition, 2001.

EXAMPLE 5

Construction of Single-Chain MX35 Antibodies

We sought to create single-chain (ScFv) versions of the veneered MX35 (vMX35) antibody and a chimeric codon-optimized MX35 (chMX35) antibody, and to use these ScFv antibodies to confirm that vMX35 and chMX35 can bind MX35 peptide in ELISA. Single-chain antibodies were produced, and single-chain antibodies based on both a veneered and chimeric MX35 antibody recognize the MX35 peptide (corresponding to amino acids 324-338 of NaPi2b (SLC34A2) (SEQ ID NO:8)).

Variable region amino acid sequences of the veneered MX 35 antibody are provided in SEQ ID NO: 38 (heavy chain) and SEQ ID NO: 39 (light chain variable region). Variable region amino acid sequences of the chimeric codon-optimized MX 35 antibody are provided in SEQ ID NO: 40 (heavy chain) and SEQ ID NO: 41 (light chain variable region). ScFv Primer Design Primers were designed to create single-chain versions of the veneered and chimeric antibodies. Single-chain variable fragment (ScFv) antibodies are composed of the variable heavy-chain coding sequence attached to a flexible linker region (Gly$_4$Ser)$_3$, followed by the variable light-chain coding sequence, and closing with an E-tag. The E-tag sequence was encoded in the pCANTAB 5E plasmid. This plasmid, along with the TG1 cells used to produce soluble ScFv, was part of the Recombinant Phage Antibody System (GE Biosciences).

MX35 ScFv primers were as follows:

vH coding sequence primers, start of vH sequence is BOLD

```
HCupstreamPD:
                                           (SEQ ID NO: 46)
CACGGCCCAGCCGGCCCAGGTGCAGCTCCAAGAGAG vMX35vHup-PD:
                                           (SEQ ID NO: 47)
CACGGCCCAGCCGGCCCAGGTGCAGCTGGTGCAGAGC chMX35vHup-PD:
                                           (SEQ ID NO: 48)
CACGGCCCAGCCGGCCCAGGTGCAATTGAAGCAGTCT
```

Primers for vH coding sequence to linker; end of vH sequence is BOLD, linker primer overlap is underlined

```
HCdownstreamPD:
                                           (SEQ ID NO: 49)
CCACCTCCGCCTGAACCGCCTCCACCGCTGCTCACTGTCACTAGGG
RC:
                                           (SEQ ID NO: 50)
CCCTAGTGACAGTGAGCAGCGGTGGAGGCGGTTCAGGCGGAGGTGG vMX35vHdown-PD:
                                           (SEQ ID NO: 51)
CCACCTCCGCCTGAACCGCCTCCACCGGATGATACAGTCACCAGGG
RC:
                                           (SEQ ID NO: 52)
CCCTGGTGACTGTATCATCCGGTGGAGGCGGTTCAGGCGGAGGTGG chMX35vHdown-PD:
                                           (SEQ ID NO: 53)
CCACCTCCGCCTGAACCGCCTCCACCGGATGACACGGTCACCAGGG
RC:
                                           (SEQ ID NO: 54)
CCCTGGTGACCGTGTCATCCGGTGGAGGCGGTTCAGGCGGAGGTGG
```

Primers for linker to vL coding sequence; linker primer is underlined, start of vL sequence is BOLD

```
LCupstreamPD:
                                           (SEQ ID NO: 55)
CAGGCGGAGGTGGCTCTGGCGGTGGCGGATCGGATATTCAGATGACTCA
GAGTC vMX35vLup-PD:
                                           (SEQ ID NO: 56)
CAGGCGGAGGTGGCTCTGGCGGTGGCGGATCGGACATCCAGATGACCCA
GAGCC chMX35vLup-PD:
                                           (SEQ ID NO: 57)
CAGGCGGAGGTGGCTCTGGCGGTGGCGGATCGGATATCCAGATGACCCA
GACCA
```

Primers for end of vL; end of vL coding sequence is BOLD.

```
LCdownstreamPD:
                                         (SEQ ID NO: 58)
CCTGCGGCCGCTTTGATTTCCAGTTTTGTGCCGCC RC:
                                         (SEQ ID NO: 59)
GGCGGCACAAAACTGGAAATCAAAGCGGCCGCAGG vMX35vLdown-PD:
                                         (SEQ ID NO: 60)
CCTGCGGCCGCTTTGAGTTCCAGTTTGGTGCCCTG RC:
                                         (SEQ ID NO: 61)
CAGGGCACCAAACTGGAACTCAAAGCGGCCGCAGG chMX35vLdown-PD:
                                         (SEQ ID NO: 62)
CCTGCGGCCGCTTTCAGCTCCAGCTTGGTGCCGGC RC:
                                         (SEQ ID NO: 63)
GCCGGCACCAAGCTGGAGCTGAAAGCGGCCGCAGG
```

Production of vMX35 and chMX35 ScFv Genes

Creating the complete ScFv sequence required two rounds of PCR. The final product was then digested with SfiI and NotI, and ligated into the pCANTAB 5E plasmid.

| vMX35 | chMX35 |
|---|---|
| PCR1-vH | |
| 2 µl vMX35vHup-PD (10 µM) | 2 µl chMX35vHup-PD (10 µM) |
| 2 µl vMX35vHdown-PD (10 µM) | 2 µl chMX35vHdown-PD (10 µM) |
| 2 µl vMX35 variable heavy template | 2 µl chMX35 variable heavy template |
| 25 µl Master Mix | 25 µl Master Mix |
| 19 µl H$_2$O | 19 µl H$_2$O |
| PCR1-vL | |
| 2 µl vMX35vLup-PD (10 µM) | 2 µl chMX35vLup-PD (10 µM) |
| 2 µl vMX35vLdown-PD (10 µM) | 2 µl chMX35vLdown-PD (10 µM) |
| 2 µl vMX35 variable light template | 2 µl chMX35 variable light template |
| 25 µl Master Mix | 25 µl Master Mix |
| 19 µl H$_2$O | 19 µl H$_2$O |
| PCR Protocol: | |
| 94° C.-15 min | Run PCR1 products on 1.5% agarose + EtBr Gel and extract ~400 bp band. Elute in 50 µl H$_2$O |
| 94° C.-60 sec\ | |
| 63° C.-30 sec| - x25 cycles | |
| 72° C.-60 sec/ | |
| 72° C.-10 min | |
| PCR2- | |
| 2 µl vMX35vHup-PD (10 µM) | 2 µl chMX35vHup-PD (10 µM) |
| 2 µl vMX35vLdown-PD (10 µM) | 2 µl chMX35vLdown-PD (10 µM) |
| 5 µl PCR1-vH product | 5 µl PCR1-vH product |
| 5 µl PCR1-vL product | 5 µl PCR1-vL product |
| 25 µl Master Mix | 25 µl Master Mix |
| 19 µl H$_2$O | 19 µl H$_2$O |

PCR2 Protocol is identical to that of PCR1. Run products through reaction clean-up column (Qiagen Qiaspin column), elute in 50 µl H$_2$O and proceed with Restriction Digestion. Digest PCR2 products using SfiI and NotI, ligate into pCANTAB 5E plasmid.

| PCR2 SfiI-NotI double-digest | pCANTAB 5E SfiI-NotI double-digest |
|---|---|
| 0.5 µl SfiI (10U) | 0.5 µl SfiI (10U) |
| 2.0 µl NotI (20U)* | 2.0 µl NotI (20U)* |
| 5.0 µl 10x NEBuffer 2 | 5.0 µl 10x NEBuffer 2 |
| 0.5 µl BSA (100x) | 0.5 µl BSA (100x) |
| 41 µl PCR2 product | 1.0 µl CIP |
| | 10 µl pCANTAB 5E plasmid |
| | 31 µl H$_2$O |

*use twice as much because NotI has only 50% reactivity in NEB2

Incubate double-digests for one hour at 37° C. Isolate digested bands for insert and plasmid by 1% agarose gel electrophoresis. Purify DNA on minicolumn (Qiagen MinElute column) and elute in 10 µl H$_2$O.

MX35ScFv+pCANTAB 5E Ligation

1 µl T4 DNA Ligase
2 µl T4 DNA Ligase Buffer
2 µl Digested Insert (vMX35 or chMX35 PCR2)
6 µl Digested Vector (pCANTAB 5E)
9 µl H$_2$O Incubate Ligation Reaction for 15 min at 22° C. Clean-up DNA by minicolumn prep and elute in 10 µl H$_2$O.

Transform chemically competent Top10 cells with ScFv plasmids according to published protocol (Invitrogen Top10 Chemically Competent E. coli).

Check isolated colonies for presence of plasmid by colony PCR. Pick isolate colonies, and using a sterile toothpick, transfer bacteria from each colony to separate tubes containing 100 µl sterile water. Lyse the cells by incubating at 95° C. for 5 minutes. Use 5 ul from each tube in the following PCR reaction:

Colony PCR 0.5 µl vMX35vLup-PD or chMX35vLup-PD
0.5 µl R2
5.0 µl Template DNA from lysed cells
7.0 µl RedTaq Master Mix
1.0 µl H$_2$O PCR Protocol is identical to that of PCR1. After PCR, run entire PCR reaction (140) in one well of a 1.5% agarose gel. Colonies that have been transformed with plasmid containing ScFv insert will have a band at ~450 bp. Grow 10 ml liquid cultures derived from PCR-verified colonies on LB+Amp overnight. Prepare glycerol stocks: To 1 ml of overnight culture, add 75 µl glycerol, vortex to mix, and store at −80° C. Purify plasmid from remaining 9 ml of each culture using a plasmid DNA-purification spin-column (Promega Wizard Plus Miniprep).

Sequence plasmids using primers R1 & R2, which bracket the ScFv sequence, annealing ~80 bases upstream or downstream, respectively.

Sequencing Primers:

```
R1:
                                         (SEQ ID NO: 64)
5'-CCATGATTACGCCAAGCTTTGGAGCC-3'

R2:
                                         (SEQ ID NO: 65)
5'-CGATCTAAAGTTTTGTCGTCTTTCC-3'
```

Note:

The region in and around sfiI site is GC-rich. This was the likely cause of errors during the PCR and ligation reactions. As a result, the transformation efficiency was low for these constructs, and there was a relatively high frequency of insertion or deletion errors within this part of the sequence. Only one perfect clone was found for vMX35 ScFv; clone #6. As for chMX35, all clones had errors in the initial round of sequencing. ChMX35 ScFv clone #5 was subsequently modified to correct a frame-shift mutation in this region. Primers were designed to take advantage of unique MunI/NMI site within the early chMX35 ScFv sequence. A corrected sequence was obtained by PCR of chMX35 ScFv clone #5 using the following primers:
cMX35 scfv Modification Primers:

PD HindIII up:
(SEQ ID NO: 66)
5'-GATTACGCCAAGCTTTGGAG-3'

Ch5 sfiI munI:
(SEQ ID NO: 67)
5'-CTTCAATTGCACCTGGGCCGGCTGGGCCGCATAGAAAGGAAC-3'

After digestion on HindIII and MfiI, this sequence was ligated into the HindIII-MfiI digested and CIP'd chMX35 ScFv clone #5. Two clones derived from the subsequent ligation and transformation, chMX35 ScFv clone #6 and chMX35 ScFv clone #8 proved to have identical, perfect sequences. Clone #8 was used in downstream applications.
Clones Containing Correct Sequences.
  used for ELISA: vMX35 ScFv clone #6
  chMX35 ScFv clone #8

The amino acid sequence for the vMX35 ScFv clone #6 is shown in FIG. 16 (SEQ ID NO: 42). The nucleic acid sequence for the vMX35 ScFv clone #6 is shown in FIG. 16 (SEQ ID NO: 43). The amino acid sequence for the chimericMX35 ScFv clone #8 is shown in FIG. 17 (SEQ ID NO: 44). The nucleic acid sequence for the chimericMX35 ScFv clone #8 is shown in FIG. 17 (SEQ ID NO: 45).
Electroporation of TG1 Cells Sequence-verified, purified plasmid from vMX35 ScFv clone #6 and chMX35 ScFv clone #8 were then used to transform electrocompetent TG1 *E. coli*. These cells were part of the RPAS kit, and could be used to produce both phage-displayed antibodies, as well the soluble single-chain antibodies which could then be used in ELISA.

Protocol:
Thaw electrocompetent TG1 vial on ice. Transfer 50 WI of cells to a pre-chilled 0.2 cm cuvette. Add 50 µl d.i.water and 2 µl of purified salt-free pCANTAB 5E plasmid with ScFv sequence. Shake to the bottom of the cuvette. Place on ice for 1 minute. Program the electroporator to give 25 µF, 2.5 kV at 200 ohms. Dry the cuvette with a tissue and place it in the electroporation chamber. Pulse once. Immediately add 1 ml of fresh LB-G or 2×YT-G medium to the cuvette and cover and invert to resuspend the cells. Incubate the remaining electroporated cells for 1 hour at 37° C. with shaking at 250 rpm. Plate 100 µl of the undiluted transformed cells as well as 1:100 and 1:10,000 dilutions onto separate SOBAG plates using a sterile spreader. When dry, invert the plates and incubate overnight at 37° C. Prepare frozen stocks from an overnight culture of a single colony in 10 ml 2×-YT-AG, cultured at 37° C. To 1 ml of this culture, add 75 µl glycerol and store at −80° C.
Periplasmic Extract Soluble E-tagged ScFv antibodies can be extracted from the periplasmic space of TG1 or HB2151 *E. coli* transfected with a single-chain antibody sequence inserted in a pCANTAB 5E plasmid and cultured in media containing IPTG. Although the literature suggests that ScFv antibodies can also be harvested from the supernatant or from the intracellular fractions of such cultures, it had been determined in previous experiments that periplasmic extracts gave the greatest yield. Thus, soluble E-tagged ScFv's were extracted for use in ELISA.

Protocol:
Grow TG1 clone containing plasmid encoding ScFv gene (vMX35 #6, and chMX35 #8) for three hours in 10 ml 2×-YT-AG media. Incubate at 37° C., shaking a 250 rpm. Pellet cells by centrifugation for 20 minutes at 1000×g. Discard supernatant and resuspend cell pellet in 10 ml 2×-YT-AI media. Incubate overnight at 30° C. or 37° C., shaking a 250 rpm. Pellet cells by centrifugation for 20 minutes at 1000×g. Discard supernatant. Resuspend cell pellet in 0.5 ml of ice-cold ⅕×TES buffer and transfer contents to a 1.5 ml microcentrifuge tube. Immediately add 0.75 ml of ice-cold ⅕×TES buffer (one part 1×TES, four parts d.i. water), and vortex to induce mild osmotic shock. Incubate on ice for 30 minutes. Centrifuge at 14000 rpm for 10 minutes. Retain supernatant, which contains ScFvs and will be used for dot-blots and ELISAs. At this point, DNA may be extracted from the cell pellet by boiling, and the presence of the sequence of interest may be detected by colony PCR.
Dot-Blot Dot-Blots were performed as a simple means of determining the presence of ScFvs from periplasmic extracts. Although this assay, as outlined, could show nothing of the ability of the ScFv antibodies to bind peptide, it did give an indication of whether ScFv antibody had been extracted, as well as a rough idea of the concentration.

Protocol:
Blot 2 ul of each periplasmic extract sample on nitrocellulose and let dry.
Samples: (C)—Positive Control; veneered 806 ScFv harvested from HB2151 cells
  (V)—vMX35 ScFv (from clone #6)
  (CH)—chMX35 (from clone #8)

Block blot for one hour in PBS+3% BSA (10 ml). Incubate for one hour on HRP-conjugated anti E-tag antibody diluted 1:1000 in PBS+3% BSA. Wash 5× with PBS+0.05% Tween20 at one minute per wash. Follow with one deionized water wash. Develop in 4Cn development buffer for <20 minutes. Stop color reaction with water wash. (4Cn Buffer: Dissolve one crushed 4Cn tablet in 500 µl 100% Ethanol; Add 75 ml PBS; Filter sterilize; Add 100 µl $H_2O_2$ immediately prior to use). Results indicate presence of soluble E-tagged ScFv antibody in periplasmic extracts.
ELISA The results of this peptide ELISA established that soluble ScFv antibodies, vMX35 ScFv #6, and chMX35 ScFv #8, do indeed recognize MX35 peptide (SEQ ID NO:8).

Protocol:
ELISA plate (NUNC) is coated with 100 µl per well of 4 ug/ml MX35 peptide (or EMEE (806) peptide for negative control) dissolved in Carbonate-Bicarbonate buffer at pH 9.6 and incubated overnight at 4° C. Peptide is removed and plate is blocked using 250 µl/well PBS+3% BSA for one hour at room temperature. A dilution plate is blocked in the same manner. Blocking Buffer is removed from dilution plate and antibody dilutions are prepared. 100 µl of dilution buffer (PBS+3% BSA+0.05% Tween20) is added to each well of the dilution plate (except for the most concentrated wells of the positive control, A1 and B1). 100 µl of periplasmic extract is added to the starting well for each dilution series (labeled "2"). The sample is mixed by pipetting up and down, and 100 µl of the mixed sample is transferred to the next well, where the process is repeated. The series continues for 11 dilutions. No antibody is added to the $12^{th}$ well, this is a negative control well. The positive control is also diluted as described, but an initial concentration of 2 µg/ml is prepared and added to the first wells. Negative controls are only diluted to 1:32.

The peptide-coated and blocked ELISA plate is emptied, and 100 µl from each well of the dilution plate is added to the corresponding well in the ELISA plate. The plate is incubated for 1.5 hours at room temperature. The plate is washed 4× using PBS+0.05% Tween20. 100 µl of HRP-conjugated secondary antibody is added to each well of the ELISA plate. In the case of the positive control, this is HRP-conjugated goat anti-mouse gamma Fc diluted 1:20000 in PBS+3% BSA+0.05% Tween20. For the E-tagged ScFv antibodies, the secondary antibody is an HRP-conjugated anti-E-tag antibody (GE Biosciences) diluted to 1:8000 in the PBS+3% BSA+0.05% Tween20. The plate is incubated for 1 hour at room temperature. The plate is washed 4× using PBS+0.05% Tween20.

Signal is detected using 100 µl/well of Dako© TMB+ substrate. Color developed within 10 minutes, and the reaction was stopped with 100 µl/well 1M Sulfuric Acid. The Absorbance at 450 nm is read and is recorded.

Figure 18:
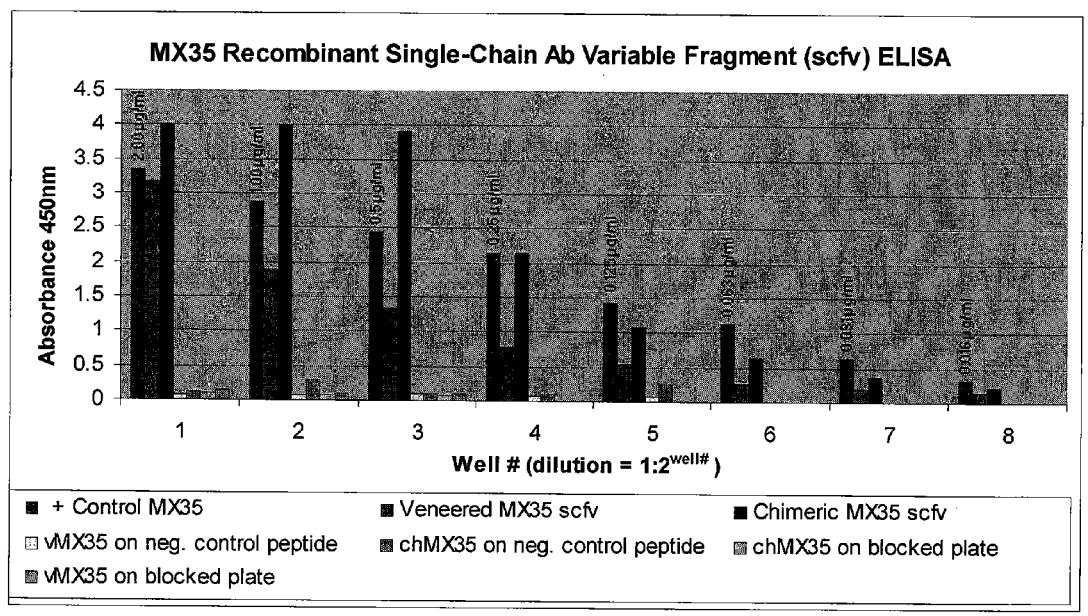
FIG. 18 depicts the results of the MX35 recombinant single chain antibody ELISA showing dilutions of MX35, veneered MX35 ScFv and chimeric MX35 ScFv versus MX35 peptide, or with negative control peptide or a blocked plate.
Figure 19:
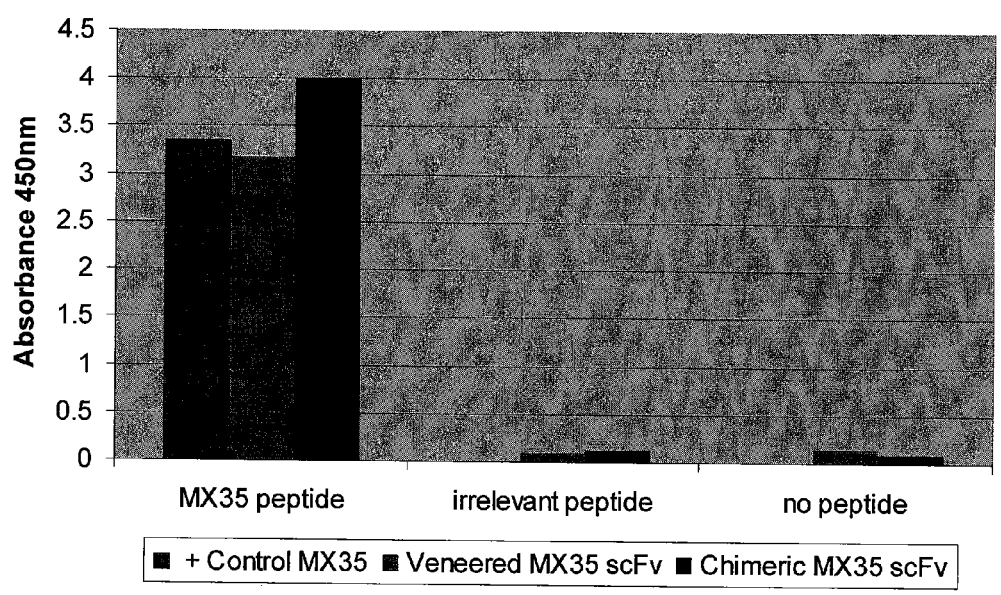
FIG. 19 shows 450 nM absorbance of ELISA of control MX35, veneered MX35 ScFv or chimeric MX35 ScFv versus MX35 peptide, irrelevant peptide, and no peptide.

A comparison of the first eight dilutions is depicted in FIG. 18. ELISA results of control MX35 antibody, veneered and chimeric scFv antibodies versus MX35 peptide, irrelevant peptide and no peptide, at a single antibody concentration are provided in FIG. 19. The single chain Fv chimeric and veneered antibodies reacted with SK-RC-18 cells (renal cell line) by mixed hemagglutination assay (data not shown).

EXAMPLE 6

SLC34A2 Variant T330 M is not Recognized by MX35 Antibody

Figure 20:
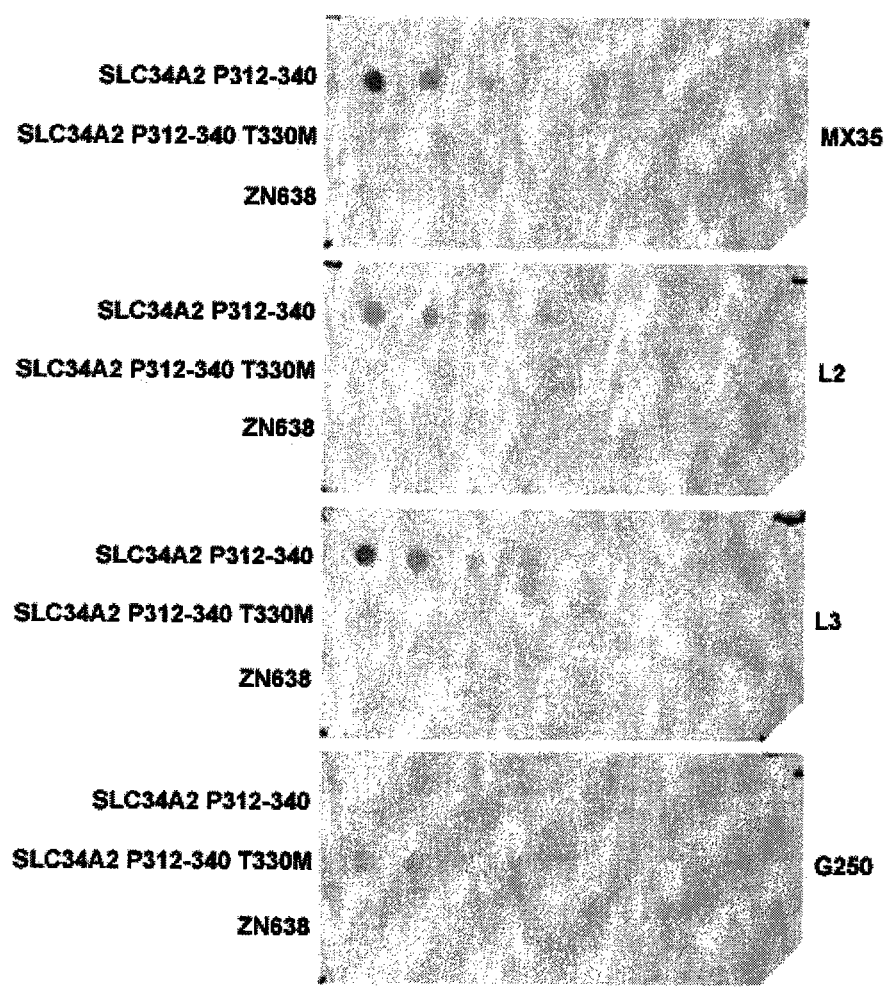
FIG. 20 shows a dot blot of antibodies MX35, L2, L3 and control G250 versus S2L34AZ peptide, including wild type 312-340 and 312-340 T330M.

SLC34A2, involved in phosphate homeostasis in several organs, has been found to be the gene responsible for pulmonary alveolar microlithiasis (PAM), a rare disease characterized by the deposition of calcium phosphate microliths throughout the lungs. Corut et al have studied and identified mutations in SLC34A2 that are predicted to cause pulmonary alveolar microlithiasis and are possibly also associated with testicular microlithiasis (Corut, A. et al (2006) AM J. Hum Genet. 79:650-656). While analyzing normal controls, Corut identified a novel variant c.989C-T (p. T330M) in an unaffected female, whereby threonine is replaced with methionine, substituting a polar residue with a non-polar residue. This is presumed to inactivate the SLC34A2 protein. This T330M mutation is located within the MX35 epitope peptide region of SLC34A2. To test whether the MX35 antibody is capable of binding to or recognizing the mutant and presumed inactive T330M SLC34A2 variant, MX35 antibody binding to T330M variant 312-340 peptide (SLC34A p312-340 T330M) (SEQ ID NO: 68) versus wild type 312-340 peptide (SEQ ID NO: 8) was assessed by dot blot. The results are shown in FIG. 20. While MX35, L2 and L3 antibodies bind p312-340 peptide SEQ ID NO: 8, none of these antibodies bind T330M P312-340 peptide by dot blot analysis.

EXAMPLE 7

Establishing Cellular Models for the Analysis of Sodium-dependent phosphate transporter NaPi2b, A Potential Marker for Ovarian Cancer The aim of present study was to establish a model for functional analysis of a recently identified marker of ovarian cancer—sodium-dependent phosphate transporter NaPi2b. For this purpose, we have created HEK293 stable cell lines expressing wild type and mutant forms of NaPi2b (T330V substitution in a large extracellular loop and a 6 amino acid residues deletion in the C-terminal cytoplasmic tail) that were revealed in ovarian cancer cell lines. The expression of wild type and mutant forms NaPi2b in created stable cell lines was confirmed by Western-blot analysis with monoclonal antibody against NaPi2b. The established cellular models described here will be useful for studying the function of sodium-dependent phosphate transporter NaPi2b in health and disease.

Epithelial ovarian cancer (EOC) is one of the leading causes of cancer-related death in women and the leading cause of gynecologic cancer death. The lack of specific markers for EOC makes it difficult to achieve the clinical objective for early detection and therapy. Thus, the identification and characterization of novel ovarian cancer markers is crucial for the development of novel diagnostic and immunotherapeutic approaches in gynecologic oncology and for understanding the molecular mechanisms of malignant growth.

Recent findings suggest that sodium-dependent phosphate transporter NaPi2b could be considered as a potential prospective marker of ovarian cancer. Firstly, NaPi2b is overexpressed in ovarian cancer in comparison to normal tissues and other types of cancer [1]. Secondly, NaPi2b was recently identified as MX35 cancer antigen by two independent approaches: a) screening of ovarian cancer cell line OVCAR3 cDNA expression library with monoclonal antibody MX35; and b) affinity purification of MX35 antigen followed by mass spectrometry analysis [2]. MX35 MAb was generated more than 20 years ago at Memorial Sloan-Kettering Cancer Center by immunizing mice with fresh ovarian carcinoma cells and screening generated hybridomas with a panel of ovarian cancer cell lines [3]. Further studies showed that MX35 antigen is expressed at high level in approximately 90% of human ovarian epithelial cancers, which created the base for using humanized MX35 MAb in early phase clinical trials [3, 4]. In normal tissues, the expression of sodium-dependent phosphate transporter 2b at the protein level is restricted to small intestine [5], lung [6], liver [7], mammary and salivary glands [8, 9].

The human sodium-dependent phosphate transporter NaPi2b is encoded by SLC34A2 gene which belongs to type II family of sodium-dependent phosphate transporters (SLC34 family). It is involved in regulating homeostasis of inorganic phosphate in human body by intestinal Pi absorption, whereas homologous sodium-dependent phosphate cotransporter NaPi2a is critical for renal Pi reabsorption [10].

NaPi2b is a transmembrane protein with molecular weight in 76-110 kDa range depending on the state of glycosylation [6-9, 11, 12]. It is predicted to be anchored to the plasma membrane through at least 8 highly hydrophobic α-helical regions [13]. It has been previously proposed that NaPi2b possesses a large extracellular loop (188-360aa), 8 transmembrane domains and the N- and C-therminal cytoplasmic tails. The largest extracellular loop contains several potential sites of glycosylation and a region rich in cysteine residues, which might be involved in disulfide bond formation [2]. We have recently described the production of several monoclonal antibodies directed against NaPi2b extracellular loop (188-360aa) and narrowed down their epitopes between amino residues 311 and 340 [14]. These antibodies might have a therapeutic value, since NaPi2b is a membrane protein and is overexpressed in ovarian cancer.

Recent studies provided the evidence that mutations in SLC34A2 gene are associated pulmonary alveolar microlithiasis (PAM) which is characterized by the deposition of calcium phosphate microliths in lungs [15]. To date, there are no data which could link mutations in SLC34A2 gene to malignant transformation.

In this study we describe two mutations in NaPi2b gene that could be potentially associated with ovarian cancer: T330V in a large extracellular loop and a 6 aa deletion in the C-terminal end of transporter. These mutations, as well as others were identified by bioinformatic analysis of NaPi2b sequences in various DNA data bases. Furthermore, we have created expression constructs of wild type and mutant forms of NaPi2b suitable for making stable cell lines. High level of expression of wild type and mutant forms of NaPi2b in established HEK293 stable cell lines was confirmed by Western-blot analysis. Generated cell lines will be used to study the regulation of NaPi2b under various experimental conditions, such as mitogenic stimulation, treatment of cells with signal transduction inhibitors, exposure to cellular stresses etc.

Material and Methods

Bioinformatic Approaches

GeneBank data bases were searched for potential mutations in sodium-dependent cotransporter Napi2b. CLUSTALW (1.82) program (www.eblac.uk/clustalw/) was used for multiple sequence alignment of different EST clones corresponding to Napi2b.

Cloning of Wild Type Napi2b into pcDNA3.1

The full length cDNA clone of human Napi2b (Napi2b_WT) was amplified from the original clone DKFZp6860655Q2 (received from RZPD gene bank) with primers containing cloning sites and sequences for the EE-tag (Table 6). The amplified cDNA fragment was then ligated into mammalian expression vector pcDNA3.1+ (Invitrogen, USA) that allows the expression of cloned cDNA in mammalian cells under the control of the CMV promoter. Generated cDNA plasmids were confirmed by restriction analysis and DNA sequencing. Plasmid DNA used in subsequent studies was purified by DNA purification kit (Promega, USA).

TABLE 6

Oligonucleotide primers used for cloning and site-directed mutagenesis

| | |
|---|---|
| FNapi2b_WT | AGTGGATCCATGGCTCCCTGGCCTGA (SEQ ID NO: 69) |
| RNapi2b_WT | CGGAATTCCTACTCCATCGGCATGAACTCCATCAA GGCCGTGCATTCGGTCT (SEQ ID NO: 70) |
| FNapi2b_del6 | GCC GAA GAA ACT CCA GAA CTG GAT GCG CTC GCT GAA GCC CTG GG (SEQ ID NO: 71) |
| RNapi2b_del6 | CCC AGG GCT TCA GCG AGC GCA TCC AGT TCT GGA GTT TCT TCG GC (SEQ ID NO: 72) |
| FNapi2b_T330V | CTC CCC TTC CCT CTG TTG GGT GGA TGG CAT CCA AAA CTG GAC (SEQ ID NO: 73) |
| RNapi2b_T330V | GTC CAG TTT TGG ATG CCA TCC ACC CAA CAG AGG GAA GGG GAG (SEQ ID NO: 74) |

Site-Directed Mutagenesis 20 ng of the pcDNA3.1/NaPi2b plasmid was amplified with 2.5 U of Pfu DNA polymerase in the presence of overlapping primers for mutagenesis (9 pmol of each). The primers contained a mutation (ac 988 gt for T330V and del1768-1785 nt for del6aa, see table1) in the middle of the sequence. PCR amplification was performed in 50 µl with 18-22 thermal cycles (95° C. for 30 s, 55° C. for 1 min and 68° C. for 16 min). Amplified DNA was precipitated, redissolved in 15 µl of water and then the parental dam-methylated DNA was digested with IOU of DpnI for 1 h at 37° C. 100 µl of XL1-Blue ultracompetent cells were transformed with 4 µl of the reaction mixture, grown for 45 min in SOC medium and plated onto LB-ampicillin plates. Plasmid DNA was purified by DNA purification kit (Promega, USA). Generated mutations were verified by sequencing analysis.

Production of Stable HEK293 Cells

Initially, produced DNA constructs were linearized with Sca1 restriction enzyme (Fermentas, Lithuania) according to manufacturer's recommendations. Transfection of HEK293 cells with FuGene (Roche, Switzerland) was performed in 6 cm plates when cell density reached 60-70%. 5 µg of each plasmid DNA (pcDNA3.1/NaPi2b-WT, pcDNA3.1/NaPi2b-T330V, pcDNA3.1/NaPi2b-Δ6aa or empty vector) was mixed with 500 µl of standard DMEM medium. FuGene reagent (10 µl) was added to each sample and incubated at room temperature for 10 min before the addition to cells. After 24 h incubation, the medium was replaced with complete DMEM medium (10% FBS, 1 mM Glutamine, penicillin (50 U/ml)/streptomycin (0.25 mkg/ml) antibiotics). After 48 h, the medium was replaced with complete DMEM medium containing 1 mg/ml G418 antibiotic (Gibco, USA). Transfected cells were cultured in the presence of G418 for 7-10 days in order to eliminate nontransfected cells. Generated stable cell lines were cultured in the presence of G418.

Cell Lysis and Western-Blot Analysis

Stably transfected HEK293 cells were lysed in buffer containing 10 mM Tris-HCl, pH 7.5, 150 mM NaCl, 10 mM MgCL$_2$, 0.5% NP-40, and a mixture of Halt Protease Inhibitor Cocktail (Pierce, USA). Protein concentration was measured by Bradford assay (Pierce, USA), and equal amounts of proteins (10 µg) were separated in 8% SDS-PAGE and blotted to polyvinylidene difluoride (PVDF) membrane (Millipore, USA). The membrane was blocked with 3% BSA in PBS (phosphate-saline buffer) containing 0.1% Tween-20 (PBST) for 1 h. Anti-NaPi2b and anti-EE-tag antibodies were incubated with membranes at 4° C. overnight. Generation of monoclonal antibodies against the extracellular loop of transporter was previously described [5]. After washing with PBST, HRP-conjugated goat anti-mouse IgG 1:5000 (Promega, USA) was added to the membrane for 1 h at RT. Western blots were developed using the ECL system (Amersham, Sweden) and then exposed to Agfa X-ray film.

Results and Discussion

We have recently identified sodium-dependent phosphate cotransporter NaPi2b as MX35 antigen which is overexpressed in 90% cases of human epithelial ovarian cancer [2, 3]. In normal cells, NaPi2b mediates the trans-epithelial efflux of inorganic phosphate and sodium ions across the apical membrane of entherocytes in small intestine and plays an important role in the maintenance of phosphate homeostasis in human body [16]. NaPi2b is also expressed on the apical surface of epithelial cells in other organs to provide appropriate inorganic phosphate level in alveolar surfactant [6], bile [7], saliva [9], and epididymal fluid [11]. Notably, NaPi2b is expressed at a very low level in normal ovary, in contrary to high expression in epithelial ovarian cancer [1, 5]. So far, the rationale for high level expression of NaPi2b transporter in ovarian cancer is not clear. This might reflect the increased demand in cancer cells for inorganic phosphate which is required for biosynthetic processes and signal transduction. The function of phosphate transporter is known to be regulated by diverse extracellular stimuli, including FGF 23, EGF, glucocorticoids, vitamin D and estrogens [17-21]. Therefore, deregulation of signaling pathways induced by oncogenic transformation may lead to the augmentation of nutrients uptake through the increased expression of transporters at the level of transcription and translation.

We have performed detailed bioinformatic analysis of potential mutations in SLC34A2 gene in available databases and composed the map of sequence variations in human NaPi2b sequence (data not shown). This study allowed us to identify 15 differences in the coding sequence of human NaPi2b: seven of them were found in genomic DNA of patients suffering from pulmonary alveolar microlithiasis; one in genomic DNA of patient with testicular microlithiasis; three in cDNA clones from ovarian cancer cell lines and four from apparently normal tissues.

Figure 21:
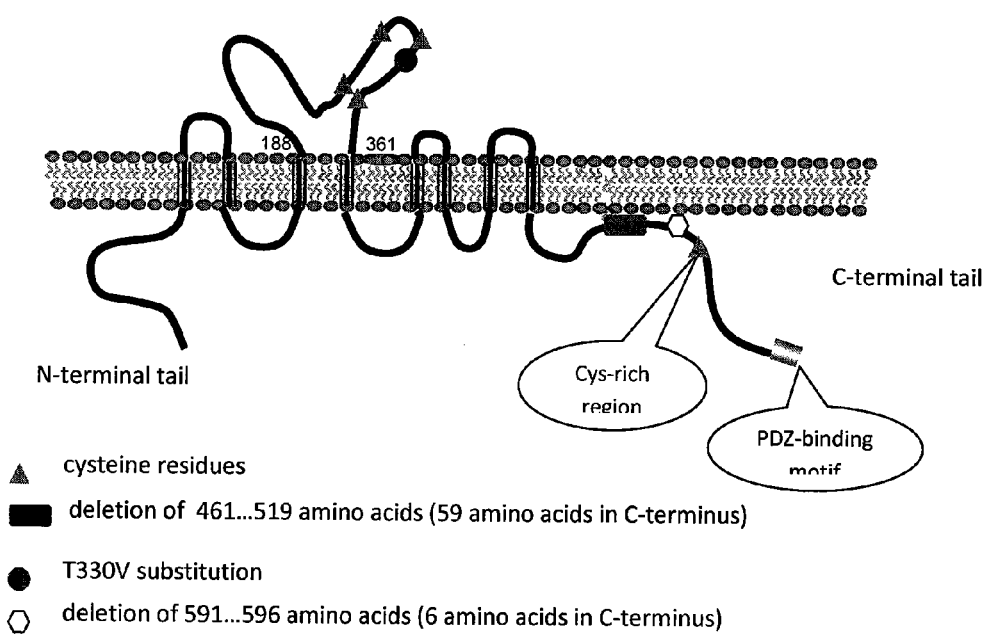
FIG. 21 providing a schematic representation of Napi2b domain organization and the location of T330V substitution, 59 and 6 aa deletion.

Bioinformatic analysis of NaPi2b sequences from ovarian cancer cell lines revealed three potentially ovarian cancer associated mutations: a) a single amino acid substitution T330V in a large extracellular loop; b) 6 as deletion (591-596aa); and c) a 56 as deletion (461-519aa) in C-terminus of transporter (FIG. 21).

Point mutation T330V is located in a large extracellular loop of Napi2b protein and therefore could influence antigenic properties of transporter. Corut et al have described T330M substitution in NaPi2b and have indicated that this mutation might inactivate NaPi2b transporter due to the substitution of polar residue to non-polar one [15]. So, this position may represent a hot spot of mutation in NaPi2b, especially in ovarian cancer.

The identified deletions in NaPi2b are located in the C-terminus tail—this region of phosphate transporter is possibly responsible for the interaction with binding partners implicated in the regulation of cellular localization and function similarly to NaPi2a [22]. A 6aa deletion is flanked by short direct repeats, which might be involved in the mechanism of mutagenesis by replication slippage [23], site-specific recombination and others. We propose that these mutations may exist in ovarian cancer and may influence NaPi2b cellular localization and function.

We have created mutant cDNA constructs of Napi2b with a point mutation T330V and a 6aa deletion of 591 . . . 596 as by site-directed mutagenesis. Unfortunately, we were not successful in making a 59 as deletion mutant in mammalian expression plasmid. Cloning of wild type NaPi2b in frame with the N-terminally located EE-tag epitope into pcDNA3.1 vector was performed as described in Materials and Methods. All generated constructs were linearized and used for stable transfection of HEK293 cells. After 7-10 days selection of transfected cells on geneticin containing medium we have selected colonies for testing NaPi2b expression.

Figure 22:
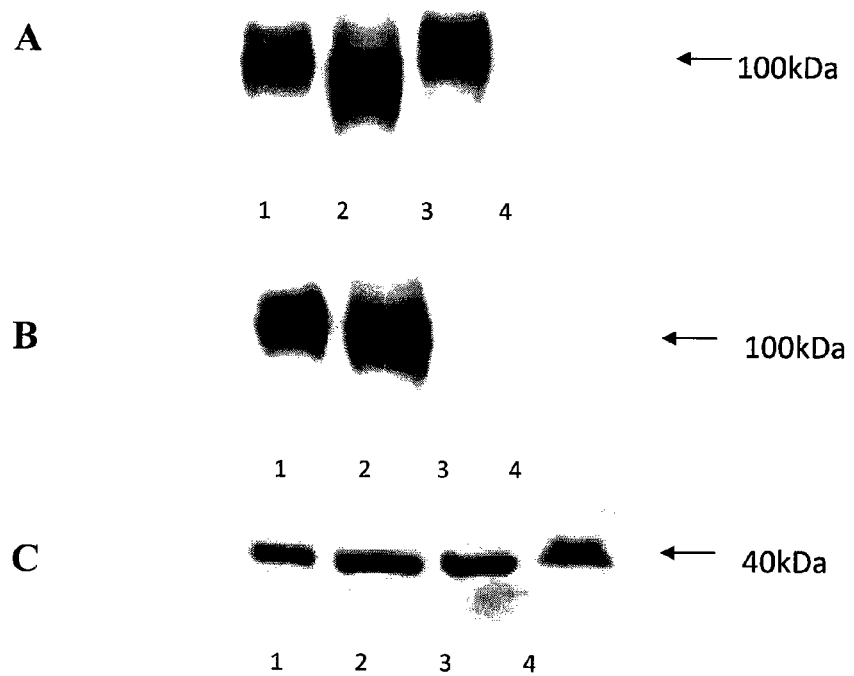
FIG. 22 shows expression of wild type and mutant forms of Napi2b in stably transfected HEK293 cells. A. WB analysis of HEK293 cells lysates with: anti-EE-tag antibody (A): anti-Napi2b antibody (L2(20/3) (B) and anti-GAPDH antibody (C). HEK293 cells transfected with pcDNA3.1/Napi2b-WT (1), pcDNA3.1/Napi2b-86aa, pcDNA3.1/Napi2b-T330V (3) and pcDNA3.1 (4).
Figure 23:
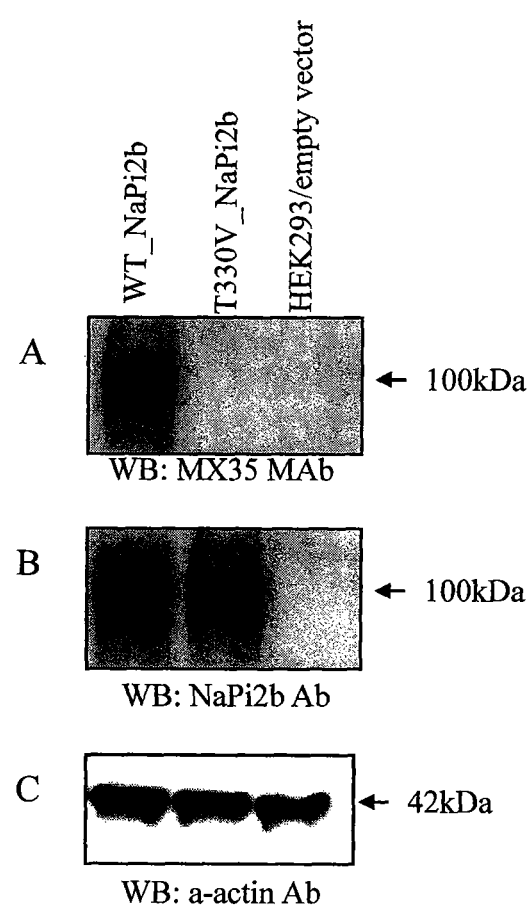
FIG. 23 shows antibody binding by Western blot to wild type and mutant form (T330V) of NaPi2b in stably transfected HEK293 cells. HEK 293 cells transfected with pcDNA3.1/NaPi2b-_WT, pcDNA3.1/NaPi2b_T330V, and pcDNA3.1 are in the lanes as noted. Western blot analysis of HEK293 lysates is shown with (A) MX35 MAb, (B) NaPi2b polyclonal antibody and (C) anti-beta actin MAb control positive.

The expression of NaPi2b (wild type and mutant forms) in HEK293 was confirmed by Western blot analysis of total cell lysates with anti-EE monoclonal antibody (FIG. 22A) or anti-NaPi2b monoclonal antibodies (FIG. 22B). Furthermore, we found that the anti-NaPi2b MAb generated against the extracellular loop of transporter (L2(20/3)) specifically recognises wild type and a 6 as deletion mutant, but does not detect the NaPi2b mutant carrying substitution T330V in the extracellular loop of NaPi2b located within a region of epitope for L2(20/3) MAb (311-340aa). These data clearly indicate that T330V substitution of hydrophilic to nonpolar amino acid could be crucial for epitope recognition by L2(20/3) MAb. The MX35 antibody epitope is also located in the same region of the large extracellular loop [2] and the MX35 MAb does not detect the NaPi2b mutant carrying substitution T330V in stably transfected HEK293 cells as assessed by Western blot (FIG. 23).

Conclusions

We have created stable cell lines expressing wild-type and mutant forms of NaPi2b phosphate transporter and have shown that T330V mutation in the extracellular loop is not recognized by anti-Napi2b L2(20/3) mAb or by MX35 antibody by Western-blot analysis. This result could be explained by the destruction or alteration of the epitope for these antibodies upon replacement of the threonine with valine in the epitope region of the NaPi2b (SLC34A2) protein and is consistent with the T330M results in Example 6 above.

Generated stable cell lines will be used for further analysis of phosphate transporter NaPi2b in normal and transformed cells. We will investigate the impact of generated mutations on the phosphate transport function and cellular processes, such as DNA biosynthesis, growth and proliferation.

REFERENCES

1. Rangel L. B., Sherman-Baust C. A., Wernyj R P., Schwartz D. R, Cho K R., Morin P. J. Characterization of novel human ovarian cancer-specific transcripts (HOSTs) identified by serial analysis of gene expression//Oncogene.—2003.—22, N 46.—P. 7225-7232.
2. Yin B. W. T., Kiyamova R., Chua R, Caballero O. L, Gout I, Gryshkova V., Bhaskaran N, Souchelnytskyi S., Hellman U, Filonenko V., Jungbluth A. A., Odunsi K, Lloyd K. O., Old L. J., Ritter G. Monoclonal antibody MX35 detects the membrane transporter NaPi2b (SLC34A2) in human carcinomas; a new target for cancer immunotherapy//Cancer Immun. [serial online].—2008.—8, N 3.—URL: http://www.cancerimmunity.org/v8p3/080103.htm.
3. Mattes M J, Look K, Furukawa K, Pierce V. K, Old L. J., Lewis J. L, Lloyd K. O. Mouse monoclonal antibodies to human epithelial differentiation antigens expressed on the surface of ovarian carcinoma ascites cells//Cancer Res.—1987.—47.—P. 6741-6750.
4. Rubin S.C., Kostakoglu L., Divgi C., Federici M G., Finstad C. L., Lloyd K O, Larson, S. M., Hoskins, W. J. Biodistribution and intraoperative evaluation of radiolabeled monoclonal antibody MX35 in patients with epithelial ovarian cancer//Gynecol. Oncol.—1993.—51.—P. 61-66.
5. Feild J A., Zhang L., Brun K A., Brooks D. P., Edwards R M. Cloning and functional characterization of a sodium-dependent phosphate transporter expressed in human lung and small intestine//Biochem. Biophys. Res. Commun.—1999.—258, N 3.—578-582.
6. Traebert M, Hattenhauer O., Murer H, Kaissling B., Biber J. Expression of a type II sodium-phosphate cotransporter in murine type II alveolar epithelial cells//Am. J. Physiol.—1999.—277.—P. L868-L873.
7. Frei P., Gao B., Hagenbuch B., Mate A., Biber J., Murer H., Meier P. J., Stieger B. Identification and localization of sodium-phosphate cotransporters in hepatocytes and cholangiocytes of rat liver//Am. J. Physiol. Gastrointest. Liver Physiol.—2005.—288.—P. G771-G778.
8. Huber K, Muscher A., Breves G. Sodium-dependent phosphate transport across the apical membrane of alveolar epithelium in caprine mammary gland//Comparative Biochemistry and Physiology.—2007.—146.—P. 215-222.
9. Homann V, Rosin-Steiner S., Stratmann T., Arnold W. H., Gaengler P., Kinne R K. Sodium-phosphate cotransporter in human salivary glands: molecular evidence for the involvement of NPT2b in acinar phosphate secretion and ductal phosphate reabsorption//Arch. Oral Biol.—2005.—50, N 9.—P. 759-768.
10. Murer H., Forster I, Biber J. The sodium phosphate cotransporter family SLC34//Pflugers Arch.—Eur. J. Physiol.—2004.—447.—P. 763-767.

11. Xu Y, Yeung C.-H., Setiawan L, Avram C., Biber J, Wagenfeld A., Lang F., and Cooper T. G. Sodium-Inorganic Phosphate Cotransporter NaPi2b in the Epididymis and Its Potential Role in Male Fertility Studied in a Transgenic Mouse Model//Biology of reproduction.—2003.—69.—P. 1135-1141.

12. Lundquist P., Murer H., Biber J. Type II Na$^+$-P cotransporters in osteoblast mineral formation; regulation by inorganic phosphate//Cell. Physiol. Biochem.—2007.—19.—P. 43-56.

13. Hilfiker H., Hattenhauer 0., Traebert M, Forster I., Murer H., Biber J. Characterization of a new murine type II sodium-phosphate cotransporter expressed in mammalian small intestine//PNAS USA.—1998.—P. 14564-14569.

14. Kiyamova R, Gryshkova V., Ovcharenko G., Lituyev D., Malyuchik S., Usenko V., Khozhayenko Yu., Gurtovyy V., Yin B., Ritter G., Old L., Filonenko V., Gout I. Development of monoclonal antibodies specific for the human sodium-dependent phosphate cotransporter NaPi2b//Hybridoma.—2008.—27, N 4.—P. 277-284.

15. Corut A., Senyigit A., Ugur S. A., Altin S., Ozcelik U, Calisir H, Yildirim Z., Gocmen A., Tolun A. Mutations in SLC34A2 cause pulmonary alveolar microlithiasis and are possibly associated with testicular microlithiasis//Am. J. Hum. Genet.—2006.—79, N 4.—P. 650-656.

16. Murer H., Hernando N., Forster I, Biber J. Molecular mechanisms in proximal tubular and small intestinal phosphate//Molecular Membrane Biology.—2001.—18.—P. 3-11.

17. Miyamoto K, Ito M, Kuwahata M, Kato S., and Segawa H. Inhibition of intestinal sodium-dependent inorganic phosphate transport by fibroblast growth factor 23//Ther. Apher. Dial.—2005.—9, N 4.—P. 331-335.

18. Xu H., Collins J., Bai L., Kiela P., Ghishan F. Regulation of the human sodium-phosphate cotransporter NaPi2b gene promoter by epidermal growth factor//Am. J. Physiol.—2001.—280.—P. C628-C636.

19. Arima K, Hines E. R, Kiela P. R., Drees J. B., Collins I F, Ghishan F. K. Glucocorticoid regulation and glycosylation of mouse intestinal type IIb Na-Pi cotransporter during ontogeny//Am. J. Physiol.—2002.—283.—P. G426-G434.

20. Katai K, Miyamoto K, Kishida S., Segawa H., Nii T., Tanaka H., Tani Y, Arai H, Tatsumi S., Morita K, Taketani Y, and Takeda E. Regulation of intestinal Na—F-dependent phosphate co-transporters by a low-phosphate diet and 1,25-dihydroxyvitamin D3//Biochem. J.—1999.—343.—P. 705-712.

21. Xu H., Uno Inouye M, Xu L., Drees I B., Collins I F, and Ghishan F. K. Regulation of intestinal NaPi2b cotransporter gene expression by estrogen//Am. J. Physiol. Gastrointest. Liver Physiol.—2003.—285.—P. GI 317-G1324.

22. Lanaspa M A., Giral H., Breusegem S. Y, Halaihel N., Baile G., Catalan J., Carrodeguas I A., Barry N P., Levi M, Sorribas V. Interaction of MAP17 with NHERF3/4 induces translocation of the renal Na/Pi Ha transporter to the transGolgi//Am. J. Physiol. Renal Physiol.—2007.—292.—P. 230-242.

23. Ball E. V., Stenson P. D., Abeysinghe S. S. Microdeletions and microinsertions causing human genetic disease common mechanisms of mutagenesis and the role of local DNA sequence complexity//Human mutation.—2005.—26, N 3.—P. 205-213.

EXAMPLE 8

Investigation of Phosphate Transporter Napi2b Expression in Different Histotypes of Epithelial Ovarian Cancer The identification of specific markers that are expressed by different histological types of epithelial ovarian cancer (EOC) may lead to the development of novel and more specific diagnostic and therapeutic strategies. Sodium-dependent phosphate transporter NaPi2b (or MX35 ovarian cancer antigen) is a novel perspective marker of EOC. To date, the studies on NaPi2b/MX35 expression in different histotypes of EOC are limited. The aim of present study was the investigation of NaPi2b/MX35 expression in different histotypes of epithelial ovarian cancer.

Methods:

Here, we describe the analysis of NaPi2b expression in serous, endometrioid, mucinous ovarian tumors by employing Western blotting, immunohistochemistry and RT-PCR.

Results:

The results of immunohistochemical and immunoblot analysis showed that benign and well-differentiated malignant papillary serous tumors as well as well-differentiated malignant endometriod tumors overexpress NaPi2b protein. However, no overexpression of NaPi2b was detected in benign and malignant mucinous tumors as well as in poorly differentiated endometriod tumors. Notably, the expression NaPi2b mRNA was detected in all investigated histological types of EOC, indicating the regulation of NaPi2b expression at the level of translation of protein stability.

Conclusion:

Since patients with well-differentiated papillary serous and endometrioid ovarian tumors have good prognosis, the expression of NaPi2b could be considered as a marker of good prognosis of these types of ovarian malignancies.

Ovarian cancer is the most common cause of death from cancers of the female genital tract [1-4]. The high fatality rate results in part from the frequent diagnosis of ovarian cancer at advanced stages. Epithelial tumors of ovary comprise 58% of all ovarian neoplasms and more than 90% of malignant tumors of ovary [5]. EOC arises from ovarian surface epithelium (OSE) that has "uncommitted" phenotype and retains the capacity to differentiate into different types of cells in response to environmental signals [6]. During ovarian cancerogenesis, the epithelium of ovary could differentiate into fallopian tube epithelium (papillary serous tumors), endomethrial epithelium (endomethrioid tumors), colonic or endocervical epithelium (mucinous tumors) and component of endometriosis (clear cell tumors). The histological analysis of EOC indicate that papillary serous tumors represent 50-60% of all ovarian cancers and the remaining tumors exhibit endometrioid (25%), mucinous (4%) and clear cell (4%) histology [7]. It is obvious that the observed tumor heterogeneity has a molecular basis and the identification of molecular markers specific for different hystologocal types of epithelial ovarian cancer can lead to the development of more effective treatment approaches.

Recently, studies from a collaborative consortium have led to the identification of sodium-dependent phosphate transporter NaPi2b as ovarian cancer antigen, termed MX35 [8]. The identity of MX35 antigen was confirmed by screening of ovarian cancer cell line OVCAR3 cDNA expression library with monoclonal antibody MX35 and by affinity purification of MX35 antigen followed by mass spectrometry. MX35 antigen was originally identified with the use of monoclonal antibody MX35, obtained from mice immunized with fresh ovarian carcinoma cells and selected by extensive analysis of normal and malignant tissues and cell lines. Biochemical and immunohistochemical studies revealed that MX35 MAb recognizes a cell surface glycoprotein of about 95 kDa which is overexpressed in 90% ovarian cancer specimens but shows restricted expression in normal tissues. Clinical studies with Fab fragments of radiolabeled MX35 antibody suggest a therapeutic potential in patients with ovarian cancer [9, 10].

The human sodium-dependent phosphate transporter NaPi2b is encoded by SLC34A2 gene which belongs to the type II family of sodium-dependent phosphate transporters (SLC34 family). It is involved in maintaining the homeostasis of inorganic phosphate in human body by regulating intestinal Pi absorption [11]. In normal tissues, the expression of NaPi2b at the protein level is restricted to small intestine [12], lung [13], liver [14], mammary and salivary glands [15, 16]. The overexpression of NaPi2b transporter in cancer was reported in epithelial ovarian carcinomas by SAGE analysis and real-time RT-PCR [17]. However, there is almost no data concerning the expression of NaPi2b/MX35 protein by different histological types of EOC. The investigation of NaPi2b expression by different histotypes of EOC might provide the insight for its prognostic value and the potential for developing immunotherapeutic approaches in ovarian cancer.

In this study, we compared the expression of NaPi2b protein between normal ovarian tissues and different histological types of EOC, such as serous, endometroid and mucinous ovarian tumors.

Materials and Methods
Tissue Samples

Tumor samples were obtained from ovarian cancer patients (28 in total) admitted for tumor resection at the Oncology Institute (NAMS of Ukraine, Kyiv, Ukraine). The types of EOC were confirmed by histopathological examination at the Department of Pathology, Oncology Institute (NAMS of Ukraine, Kyiv, Ukraine). Normal ovarian tissues were used as control samples. The mean age of patients with ovarian cancer and controls was 47 (range 22-69) and 46 (range 19-69), respectively. The study was approved by the Ethics Committee of the Institute of Molecular Biology and Genetics, and consent forms were obtained from all patients.

Western-Blot Analysis

We have analyzed NaPi2b expression in 28 ovarian cancer samples and 10 normal ovaries. Tissues samples were homogenized in RIPA buffer (20 mM TrisHCl, pH 7.5, 0, 150 mM NaCl, 1 mM EDTA, 1% NP-40, 0, 1% SDS) supplemented with PMSF (Sigma, Steinheim, Ill.), and Protease Inhibitor Cocktail (Sigma, Steinheim, Ill.) and then centrifugated at 4° C. for 30 min. Soluble fractions of lysates (50 μg per sample) were separated by 8% SDS-PAGE at non-reducing conditions. Separated proteins were transferred to a PVDF membrane for 2 hours at 80V (Perkin Elmer, Boston, Mass.) using a wet transfer cell (Pharmacia Biotech). After the transfer, the membrane was blocked in PBST buffer (1×PBS with 0, 05% Tween), containing 3% BSA and then incubated with anti-NaPi2b (0.5 mg/ml) mAb [18] at 4° C. overnight. After extensive washing in PBST buffer, the membrane was incubated with anti-mouse IgG secondary antibody (1:5000) for 1 h (Promega, Madison, Wis.). The immune complexes were detected by ECL system (Amersham, Uppsala, Sweden). GAPDH was used as a loading control.

Immunohistochemistry

Immunohistochemical analysis of ovarian cancer samples with anti-NaPi2b MAbs was performed according to a standard protocol. Briefly, representative sections of ovarian tumors were prepared from paraffin blocks. Endogenous peroxidase was quenched with $H_2O_2$ (3%) in 0.01% PBS. After blocking of non-specific binding with avidin-biotin blocking solution (Vector Laboratories, Burlingame, Calif., USA), tissue sections were incubated overnight at 4° C. with anti-NaPi2b mAb (10 mkg/ml). Then, sections were incubated with biotinylated secondary antibodies for 2 hours at room temperature in 1:400 dilution, (goat anti-mouse biotinylated IgG, Sigma, Steinheim, Germany), followed by incubation with avidin-biotin-peroxidase complex (Vector Laboratories, Burlingame, Calif., USA) for 30 min at RT and developed with diaminobenzidine solution. Haematoxylin was used for counterstaining. Standard microscopy was performed using a Zeiss Universal microscope (Zeiss, Jena, Germany), and images were captured using digital Axiocam software.

Purification of Total RNA and RT-PCR Analysis

Total RNA was isolated by acid guanidinum-thiocyanate-phenol-chloroform extraction procedure [19]. Briefly, 1 ml of denaturation solution (4M guanidinium thiocyanate, 25 mM sodium citrate, pH 7.0, 5% sarcosyl, 0.1M 2-mercaptoethanol) was added to 100 mg of homogenized tissues. Sequentially, 0.1 ml of 2M sodium acetate, pH 4, 1 ml of phenol (water saturated), and 0.2 ml of chloroform-isoamyl alcohol mixture (49:1) were added to the homogenate. After centrifugation at 10,000 g for 20 min at 4° C., total RNA was precipitated from aqueous phase with the same volume of isopropanol at −20° C. for 1 h. The pellet was resuspended in 75% ethanol, air dried and dissolved in 50 μl nuclease-free water.

Purified total RNA (5 μg) was converted to cDNA with M-MuLV Reverse Transcriptase (Fermentas) at 37° C. for 60 mM using oligo dT primers. Produced cDNA (100 ng) were amplified using following primers—forward GTCATCAC-TAAGCCCTTCACA (SEQ ID NO: 75) and reverse CAG-GCAACCACAGAGGAC (SEQ ID NO: 76)—for 30 cycles in 50 μl total volume of PCR buffer 5×PCR (Fermentas) containing 10 mM dNTP, one unit Taq polymerase, 20 pmol of each primer. The amplification was performed in DNA Thermal cycler (Perkin Elmer) under following conditions: 94° C. for 60 s, 60° C. for 30 s and 72° C. for 60 s. Amplified products were separated on a 1% agarose gel and visualised.

Results

In this study, we examined NaPi2b expression in ovarian tumors of serous, endometroid and mucinous histology. In a panel of 28 ovarian tumors, there were 17 serous tumors (3-cystadenomas, 1 papillary cystadenoma and 13 papillary carcinomas); 8 endometrioid tumors (1 cystadenoma, 4 low-grade and 3 high-grade carcinomas); and 3 mucinous tumors (1 cystadenoma, and 2 carcinomas). The techniques of Western blot, immunohistochemistry and RT-PCR were employed to examine the expression profile of NaPi2b in these tumors and to compare them with normal ovarian tissues.

Western-Blot Analysis of NaPi2b Expression

Figure 24:
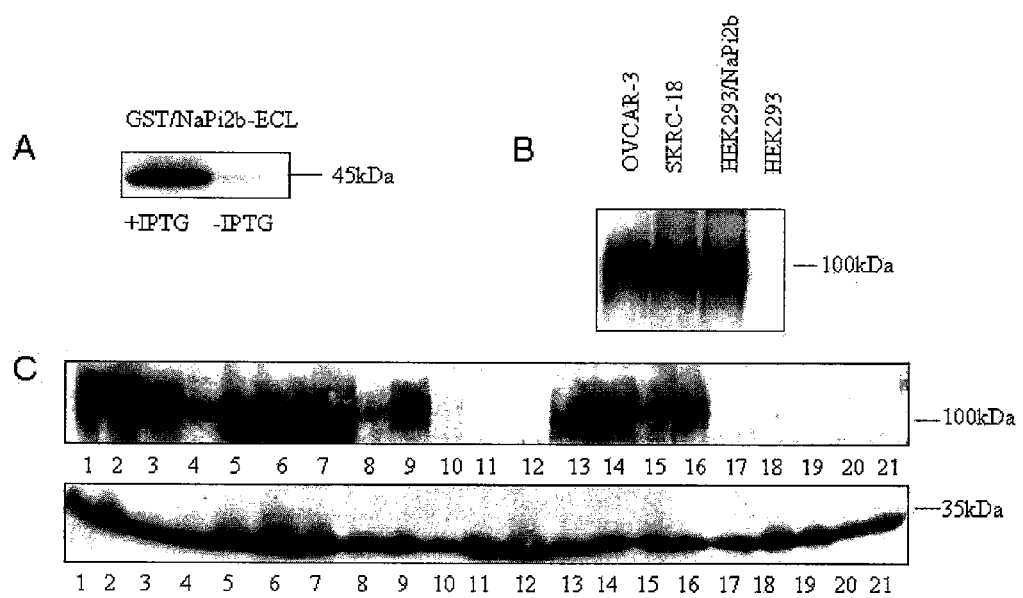
FIG. 24 shows Western-blot analysis of NaPi2b protein with anti-NaPi2b MAb generated against extracellular loop (ECL) of NaPi2b. (A) Expression of GST/NaPi2b-ECL in bacteria was induced by 1 mM IPTG. Total lysates were resolved by SDS-PAGE and probed with anti-NaPi2b MAb; B) Endogenous expression of NaPi2b protein in OVCAR-3, SKRC-18 cell lines and HEK293 cells stably expressing NaPi2b; C) Expression of NaPi2b in different types of ovarian cancer and normal ovary (upper figure), lane 1-8—papillary serous carcinoma, lane 9—papillary serous cystadenoma, lane 10—serous cystadenoma, lane 11—endometrioid cystadenoma, lane 12—poor-differentiated endometrioid carcinoma, lane 13-16—well-differentiated endometrioid cystadenoma, lane 17—mucinous cystadenoma, 18—mucinous carcinoma, lane 19-21—normal ovary. GAPDH was used as a loading control (lower figure).

Immunoblot analysis of NaPi2b expression in ovarian samples was performed under non-reduced conditions using monoclonal antibody raised against the extracellular loop of human NaPi2b (188-360aa). The specificity of anti-NaPi2b MAb was tested with the use of recombinant NaPi2b expressed in bacteria as GST fussion protein (FIG. 24A). Furthermore, we confirmed the expression of endogenous NaPi2b protein in ovarian cancer cell line (OVCAR3), kidney carcinoma cell line (SKRC18) that are MX35 positive cell lines and HEK293 stably expressing NaPi2b protein (FIG. 24B) in Western-blotting.

It has been previously demonstrated that NaPi2b protein is recognized in WB as panel of immunoreactive bands with different molecular weight, reflecting the state of glycosylation [12-16, 20-22]. The results presented in FIG. 24C show that NaPi2b is recognized in ovarian tumor lysates as band of 100 kDa. Notably, only some ovarian tumors overexpress NaPi2b.

Further analysis indicated that the expression of NaPi2b is detected in all (13/13) investigated samples of papillary serous cancers. In case of benign serous tumors NaPi2b expression was detected only in papillary cystadenoma (1/1), whereas serous cystadenomas with non-papillar structure did not express NaPi2b (3/3) (FIG. 24C).

In endometrioid tumors NaPi2b expression was found in some of tested tumors. Interestingly, low-grade endometrioid carcinomas (4/4) showed overexpression of NaPi2b, while high-grade endometrioid carcinomas (3/3) and endometrioid cystadenoma (1/1) did not express detectable level of Napi2b (FIG. 24C).

The expression of NaPi2b protein in WB was not detected in mucinous cystadenoma (1/1) and mucinous carcinomas as well as in control ovarian lysates (10/10) (FIG. 24C).

Immunohystochemical Analysis of Ovarian Tumors and Normal Tissues of the Gynaecological Tract With Anti-NaPi2b MAb We performed immunohystochemical detection of NaPi2b in all samples of ovarian cancer tumor mentioned above and normal tissues of ovary. The presence of NaPi2b by immunohystochemical staining was observed only on the apical surface of the epithelial cells that is a characteristic feature of NaPi2b expression.

Figure 25:
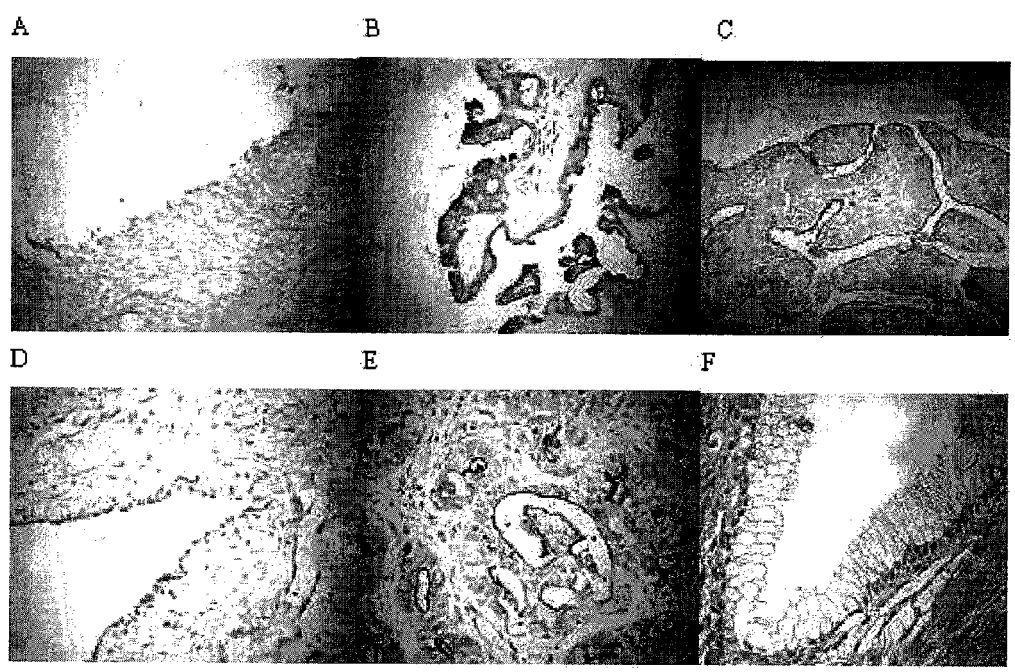
FIG. 25 provides immunohistochemistry of ovarian tumors and normal ovaries samples with anti-NaPi2b MAb. A—normal ovary, B—papillary serous carcinoma, C—papillary serous cystadenoma, D—serous cystadenoma, E—well-differentiated endometrioid carcinoma, F— mucinous cystadenoma.
Figure 26:
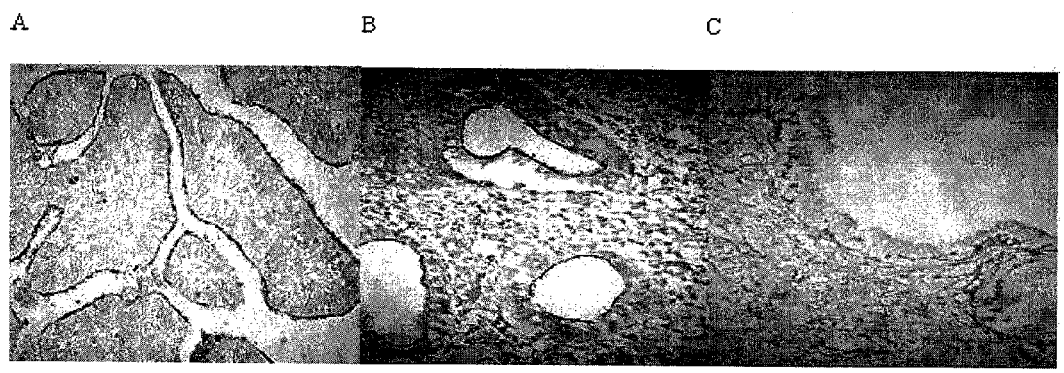
FIG. 26 provides immunohistochemistry of normal fallopian tubes (A), endometrium (B), endocervical epithelium (C) with anti-NaPi2b MAb

We found that the surface epithelium of normal ovary as well as ovary stroma were negative for NaPi2b staining (FIG. 25A). IH analysis of serous tumors showed strong staining with anti-NaPi2b MAb in papillary serous carcinomas (FIG. 25B) and papillary serous cystadenomas (FIG. 25C) but no staining was detected in serous cystadenomas with non-papillary structures (FIG. 25D). Moreover, low-grade endometrioid tumors exhibited strong staining with NaPi2b MAb (FIG. 25E) which was absent in high-grade and benign endometrioid tumors. In all examined cases, benign and malignant mucinous ovarian tumors were negative for NaPi2b (FIG. 25F). The results presented above indicate a good correlation between the expression of NaPi2b protein and the tumor type. Differential pattern of NaPi2b protein expression in various types of ovarian tumors prompted us to examine NaPi2b protein expression in normal tissues of the gynaecological tract such as fallopian tubes, endometrium and endocervics. We observed the positive staining with NaPi2b MAb in normal fallopian tube epithelium (FIG. 26A) and endometrium (FIG. 26B) but not in endocervical epithelium (FIG. 26C).

RT-PCR Analysis of SLC34A2

Figure 27:
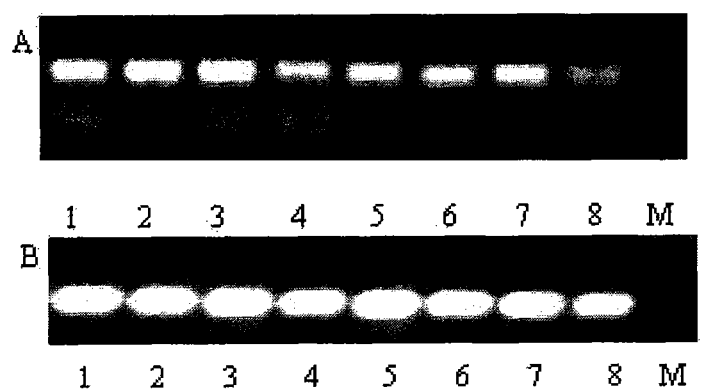
FIG. 27 shows RT-PCR analysis of ovarian tumor samples with SLC34A2 primers (A) and primers to b-actin (B). Lane 1—papillary serous carcinoma, lane 2—papillary serous cystadenoma, lane 3—serous cystadenoma, lane 4—endometrioid cystadenoma, lane 5—well-differentiated endometrioid carcinoma, lane 6—mucinous cystadenoma, lane 7—mucinous carcinoma, lane 8—normal ovary.

Total RNA derived from 28 ovarian cancer tissues and 10 normal ovaries were investigated in RT-PCR analysis with SLC34A2 specific primers (see materials and methods) which were designed for unique sequences of SLC34A2 gene. The product of amplification (350 bp) was analysed on an agarose gel. The results presented in FIG. 27A show SLC34A2 gene expression at the level of mRNA in all tissues analyzed.

Discussion

We have recently identified sodium-dependent phosphate cotransporter NaPi2b as MX35 antigen which is known to be overexpressed in 90% of human ovarian cancers [8, 9]. The pattern of NaPi2b expression in normal tissues and ovarian cancer makes NaPi2b/MX35 antigen a potential target for the development of immunotherapeutic and diagnostic approaches of EOC.

NaPi2b is a transmembrane glycoprotein that possesses 8 transmembrane domains, a large extracellular loop (188-360aa) with several potential sites of glycosylation, and the N- and C-terminal cytoplasmic tails facing the cytosol [8]. In addition to MX35 antibody, we have recently developed several monoclonal antibodies recognizing the extracellular loop of human NaPi2b [18]. To our knowledge, the expression of NaPi2b/MX35 protein in different histotypes of EOC have not been analysed so far. The elucidation of NaPi2b expression profile in various types of ovarian cancer might be useful not only for understanding molecular mechanisms of cancerogenesis, but also for the verification of diagnosis, prognosis and treatment strategies.

In this study, we have analyzed NaPi2b expression at protein and mRNA levels in different types of epithelial ovarian cancer and normal tissues of gynaecological tract. We have observed a good correlation of NaPi2b protein expression detected by WB and IH in ovarian cancer samples with different histological tumor types. Our results showed that NaPi2b protein is overexpressed in papillary serous tumors and low-grade endometrioid tumors when compared to mucinous ovarian cancer. The most common histological type of EOC is papillary serous carcinomas which are often associated with concentric rings of calcification known as psammoma bodies [23]. Notably, breast and papillary thyroid cancers, which are characterized by abberrant expression of NaPi2b, are also affected by calcifications [24, 25]. It has been demonstrated that the downregulation of the NaPi2b transport function results in the deposition of calcium phosphate microliths in patient's lungs. This phenomenon is caused by mutations in SLC34A2 gene of phosphate transporter which culminate in the development of pulmonary alveolar microlithiasis (PAM) [26]. Based on these data we propose that the calcification in papillary serous ovarian cancer could be associated with the failure of calcium phosphate homeostasis due to the aberrant expression or mutations in NaPi2b phosphate transporter gene.

Since low tumor grade has been associated with good outcome and survival [27,28], the overexpression of NaPi2b in well-differentiated papillary serous and endometrioid carcinomas could be a marker of a good prognosis. Our data correlate well those published by with Rangel et al., showing that well differentiated epithelial ovarian tumors tend to express higher level of NaPi2b [17].

Immunohistochemistry (IH) analysis of normal gynecologic tract tissues with NaPi2b MAb revealed its expression in fallopian tube epithelium and endometrium, but not in endocervical epithelium. Since ovarian surface epithelium of papillary serous tumors resembles epithelium of fallopian tube, and endometrioid tumors—endometrium epithelium and mucinous tumors—colonic or endocervical epithelium [29], it is not surprising that only papillary serous and endometrioid tumors of low grade overexpressed NaPi2b protein. So, the overexpression of NaPi2b protein in well-differentiated papillary serous and endometrioid tumors is linked to differentiation of ovarian surface epithelium into fallopian tubes epithelium and endometrium, respectively.

The expression of NaPi2b mRNA in different types of EOC showed no correlation with that of NaPi2b protein detected by IH and WB. We observed mRNA NaPi2b expression in all investigated histological types of EOC and did not reveal significant difference between samples with high and low level of NaPi2b protein expression. The absence of correlation between NaPi2b mRNA and protein expression could indicate the regulation of NaPi2b expression at the level of translation or protein stability. These results correlate with data by Rangel et. al. data showing up-regulation of SLC34A2 expression in serous, endometrioid, mucinous and clear-cell tumors of EOC by Real-time RT-PCR analysis [17].

In summary, our data demonstrate that phosphate transporter NaPi2b is overexpressed in well-differentiated papillary serous and endometrioid ovarian tumors associated with good prognosis. Moreover, we found that differential expression of NaPi2b in EOC may be the consequence of changes in ovarian epithelium differentiation during malignant process.

The findings of this study might facilitate the rational development of new diagnostic modalities and tailored therapies for ovarian malignancies.

REFERENCES

1. Jemal A, Siegel R, Ward E, et al. Cancer statistics. CA Cancer J Clin 2008; 58:71-96.
2. Cannistra SA. Cancer of the ovary. N Engl J Med 2004; 351:2519-2529.
3. Bhoola S, Hoskins W J. Diagnosis and management of epithelial ovarian cancer. Obstet Gynecol 2006; 107:1399-1410.
4. Ozols R F, Rubin S C, Thomas G M, Robboy S J. Epithelial ovarian cancer. In: Hoskins W J, Young R C, Markman M, Perez C A, Barakat R, Randall M, eds. Principles and Practice of Gynecologic Oncology. Philadelphia, Pa.: Lippincott Williams & Wilkins 2005; 895-988.
5. Zoloudek C F. Tumors of the ovary. In: Fletcher C. Diagnostic Histopathology of Tumors. New-York, N.Y.: Churchill Livingstone, third edition; 2007: 501-555.
6. Auersperg N, Wong A S, Choi K C, Kang S K, Leung P C. Ovarian surface epithelium: biology, endocrinology, and pathology. Endocr Rev. 2001; 22(2):255-88.
7. Farley J, Ozbun L L, Birrer M J. Genomic analysis of epithelial ovarian cancer. Cell Res. 2008; 18(5):538-48.
8. Yin B. W. T., Kiyamova R., Chua R., Caballero O. L, Gout I., Gryshkova V., Bhaskaran N., Souchelnytskyi S., Hellman U., Filonenko V., Jungbluth A. A., Odunsi K., Lloyd K. O., Old L J., Ritter G. Monoclonal antibody MX35 detects the membrane transporter NaPi2b (SLC34A2) in human carcinomas; a new target for cancer immunotherapy. Cancer Immun [serial online] 2008; 8:3. URL: cancerimmunity.org/v8p3/080103.htm.
9. Mattes M. J, Look K, Furukawa K, Pierce V. K, Old L. J, Lewis J. L, Lloyd K. O. Mouse monoclonal antibodies to human epithelial differentiation antigens expressed on the surface of ovarian carcinoma ascites cells. Cancer Res 1987; 47, 6741-6750.
10. Rubin S. C, Kostakoglu L, Divgi C, Federici M. G, Finstad C. L, Lloyd K. 0, Larson, S. M, Hoskins, W. J. Biodistribution and intraoperative evaluation of radiolabeled monoclonal antibody MX35 in patients with epithelial ovarian cancer. Gynecol Oncol 1993; 51, 61-66.
11. Murer H, Forster I, Biber J. The sodium phosphate cotransporter family SLC34. Pflugers Arch—Eur J Physiol 2004; 447: 763-767.
12. Feild J A, Zhang L, Brun K A, Brooks D P, Edwards R M. Cloning and functional characterization of a sodium-dependent phosphate transporter expressed in human lung and small intestine. Biochem Biophys Res Commun 1999; 258(3):578-82.
13. Traebert M, Hattenhauer 0, Murer H, Kaissling B, Biber J. Expression of a type II sodium-phosphate cotransporter in murine type II alveolar epithelial cells. Am J Physiol 1999; 277:L868-L873.
14. Frei P, Gao B, Hagenbuch B, Mate A, Biber J, Murer H, Meier P J, Stieger B. Identification and localization of sodium-phosphate cotransporters in hepatocytes and cholangiocytes of rat liver. Am J Physiol Gastrointest Liver Physiol 2005; 288:G771-G778.
15. Huber K, Muscher A, Breves G. Sodium-dependent phosphate transport across the apical membrane of alveolar epithelium in caprine mammary gland. Comparative Biochemistry and Physiology 2007; 146: 215-222.
16. Homann V, Rosin-Steiner S, Stratmann T, Arnold W H, Gaengler P, Kinne R K. Sodium-phosphate cotransporter in human salivary glands: molecular evidence for the involvement of NPT2b in acinar phosphate secretion and ductal phosphate reabsorption. Arch Oral Biol. 2005; 50(9):759-68.
17. Rangel L B, Sherman-Baust C A, Wernyj R P, Schwartz D R, Cho K R, Morin P J. Characterization of novel human ovarian cancer-specific transcripts (HOSTs) identified by serial analysis of gene expression. Oncogene 2003; 22(46): 7225-32.
18. Kiyamova R, Gryshkova V, Ovcharenko G, Lituyev D, Malyuchik S, Usenko V, Khozhayenko Yu, Gurtovyy V, Yin B, Ritter G, Old L, Filonenko V, Gout I. Development of monoclonal antibodies specific for the human sodium-dependent phosphate cotransporter NaPi2b. Hybridoma 2008; 27(4):277-284.
19. Siebert P D, Chenchik A. Modified acid guanidinium thiocyanate-phenol-chloroform RNA extraction method which greatly reduces DNA contamination. Nucleic Acids Res. 1993; 21(8):2019-20.
20. Xu Y, Yeung C—H, Setiawan I, Avram C, Biber J, Wagenfeld A, Lang F, and Cooper TG: Sodium-Inorganic Phosphate Cotransporter NaPi2b in the Epididymis and Its Potential Role in Male Fertility Studied in a Transgenic Mouse Model. Biology of reproduction 2003; 69:1135-1141.
21. Lundquist P, Murer H, Biber J. Type II Na$^+$-P cotransporters in osteoblast mineral formation;
regulation by inorganic phosphate. Cell Physiol Biochem 2007; 19:43-56.
22. Hilfiker H, Hattenhauer 0, Traebert M, Forster I., Murer H, Biber J Characterization of a new murine type II sodium-phosphate cotransporter expressed in mammalian small intestine. Proc Natl Acad Sci USA 1998; 14564-14569.
23. Maki, M.; Hirota, S.; Kaneko, Y.; Morohoshi, T. Expression of osteopontin messenger RNA by macrophages in ovarian serous papillary cystadenocarcinoma: a possible association with calcification of psammoma bodies. Pathol Int. 2000; 50(7):531-5.
24. Blanchard, A.; Shiu, R.; Booth, S. et al. Gene expression profiling of early involuting mammary gland reveals novel genes potentially relevant to human breast cancer. Frontiers in Bioscience 2007; 12: 2221-2232.
25. Gałza-Kulik M, Zebracka J, Szpak-Ulczok S, et al., Expression of selected genes involved in transport of ions in papillary thyroid carcinoma. [Article in Polish] Endokrynol Pol. 2006; 57:26-31.
26. Corut A, Senyigit A, Ugur S A, Altin S, Ozcelik U, Calisir H, Yildirim Z, Gocmen A, Tolun A: Mutations in SLC34A2 cause pulmonary alveolar microlithiasis and are possibly associated with testicular microlithiasis. Am J Hum Genet. 2006; 79 (4):650-656.
27. Makar A P, Beakeland M, Trope C G, et al. The prognostic significance of residual disease, FIGO substage, tumor histology, and grade in patients with FIGO stage Ill ovarian cancer. Gynecol Oncol 1995; 56(2): 175-180.
28. Shimuzu Y, Kamoi S, Amada S, et al. Toward the development of a universal grading system of ovarian epithelial carcinoma. 1. Prognostic significance of hystopathologic features—problems involved in the architectural grading system. Gynecol Oncol 1998; 70 (1): 2-12.
29. Seidman J D, Kurman R J. Pathology of ovarian carcinoma. Hematol Oncol Clin North Am 2003; 17:909-925.

EXAMPLE 9

MX35 antibody downregulates NaPi2b and inhibits the Transport of Phosphate

Figure 28:
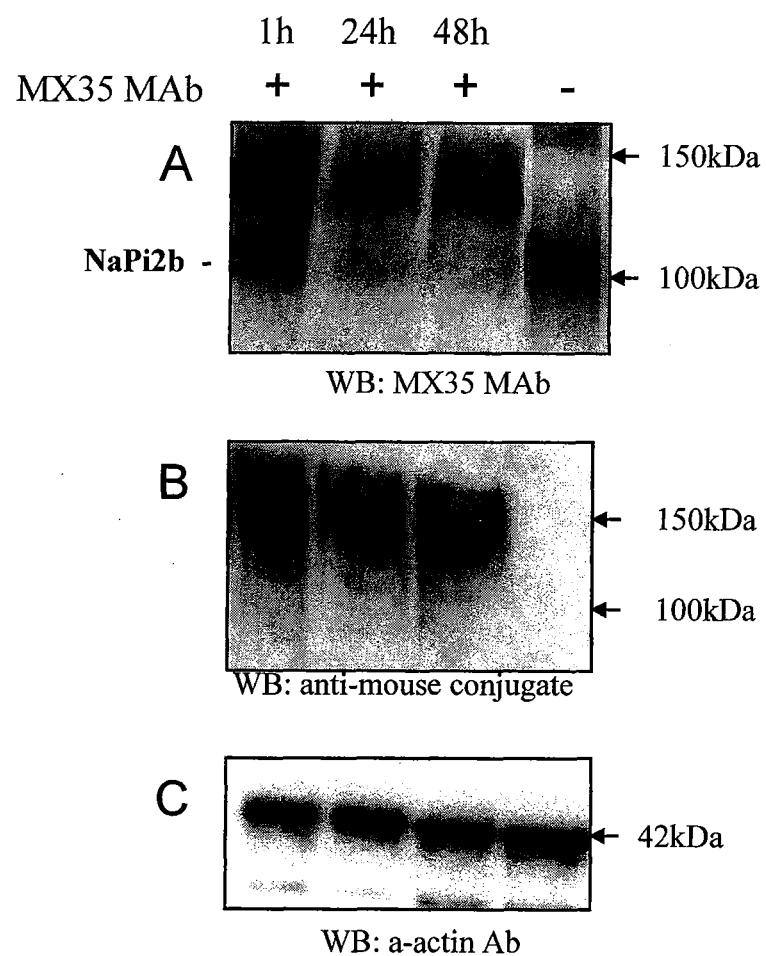
FIG. 28 shows the results of preincubation of HEK293 cells expressing wild type NaPi2b with MX35 MAb. HEK293 cells expressing wild type of NaPi2b were preincubated with MX35 monoclonal antibodies (50 mkg/ml) for a period of 1 h, 24 h or 48 h. WB analysis of HEK293 cells lysates with MX35 MAb (A), anti-mouse conjugate (B), and anti-beta actin MAb (C).

Pre-incubation of MX35 antibodies with HEK293 cells stably transfected with wild type NaPi2b (SLC34A2) resulted in inhibition of the sodium dependent phosphate transport. HEK 293 cells expressing wild type NaPi2b (SLC34A2) were preincubated with MX35 antibody (50 ug/ml) for a period of 1 hour, 24 hr or 48 hr. Western blot analysis of HEK293 cell lysates with MX35 antibody, anti-mouse conjugate and control anti-beta actin MAb is shown in FIG. 28. NaPi2b levels were reduced on preincubation with MX35 antibody.

Figure 29:
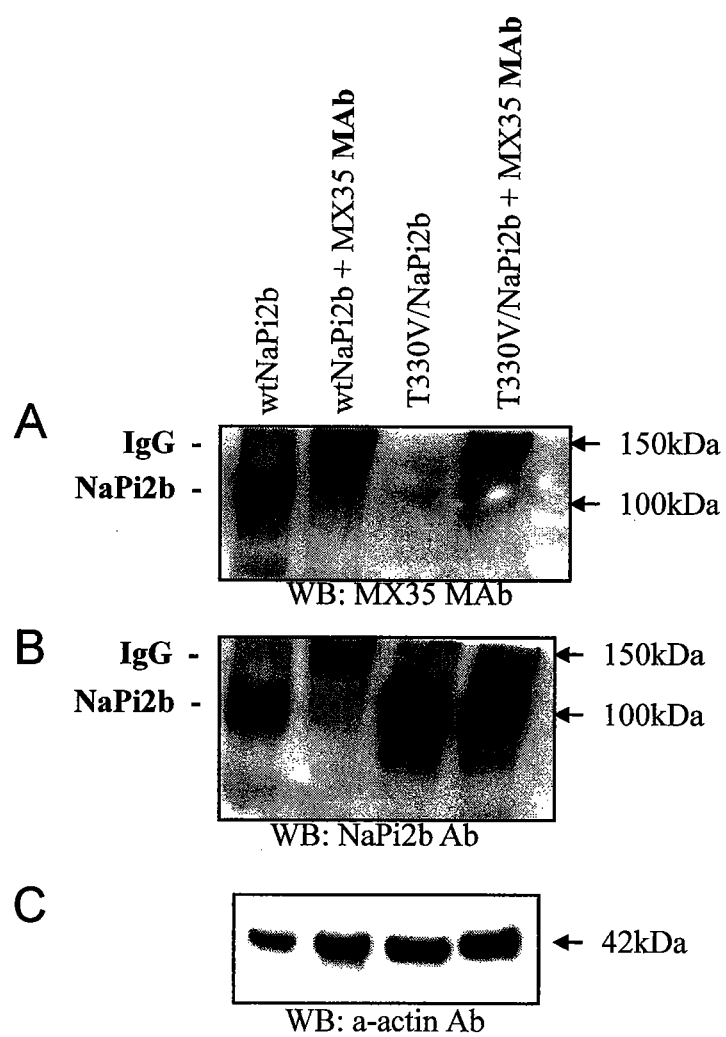
FIG. 29 depicts MX35 MAb downregulation of the level of wild type NaPi2b but not its mutant form T330V in stable HEK293 cells. HEK293 expressing wild type and mutant form T330V of NaPi2b transporter were preincubated with MX35 MAb (50 mkg/ml) during 24 h. WB analysis of HEK293 cells lysates is shown with MX35 MAb (A), anti-NaPi2b polyclonal serum (B) and anti-beta actin MAb (C).

While MX35 antibody downregulated the level of wild type NaPi2b ikn stable HEK293 cells, the lecel of mutant T330V form of NaPi2b was not altered or reduced upon preincubation with MX35. These results are shown in FIG. 29.

Figure 30:
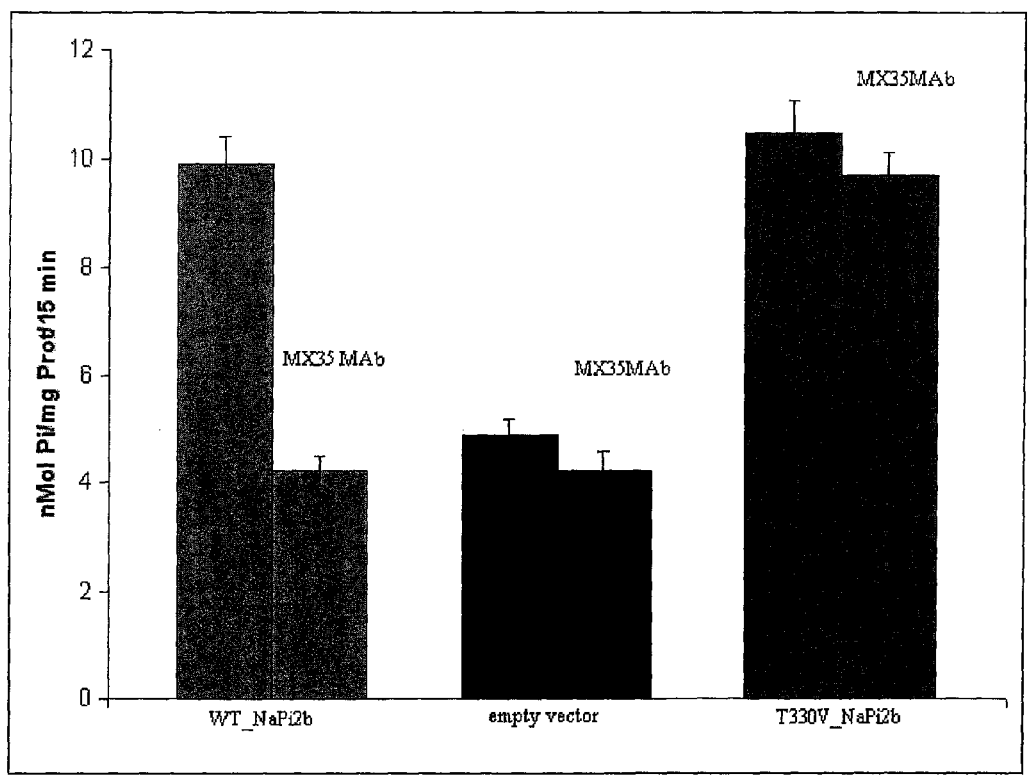
FIG. 30 shows phosphate transport inhibition by preincubation fo HEK293 cells expressing wild type NaPi2b with MX35 MAb. HEK293 cells (expressing WT, mutant form T330V of NaPi2 band empty vector) were preincubated with MX35 MAb (50 mkg/ml) during 24 h. Phosphate uptake assay was performed in the presence of P33 during 15 min. The results were reproduced in 5 independent experiments.

Preincubation of HEK293 cells expressing wild type NaPi2b (SLC34A2) with MX35 MAb inhibited the transport of phosphate. This is shown in FIG. 30. The phosphate assay was performed in the presence of P33 for 15 min. nMol Pi per mg of protein is tabulated.

This invention may be embodied in other forms or carried out in other ways without departing from the spirit or essential characteristics thereof. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. An isolated nucleic acid which comprises a sequence encoding an antibody which specifically binds the extracellular region of SLC34A2 having a heavy chain and a light chain wherein the heavy chain variable region comprises the CDRs as set out in SEQ ID NOs: 26-28 and the light chain variable region comprises the CDRs as set out in SEQ ID NOs: 31-33.

2. The isolated nucleic acid of claim 1 which comprises a sequence encoding an antibody having a heavy chain and a light chain wherein the heavy chain variable region comprises the amino acid sequence as set out in SEQ ID NO: 38 and the light chain variable region comprises the amino acid sequence as set out in SEQ ID NO: 39.

3. The isolated nucleic acid of claim 1 which comprises a sequence encoding an antibody comprising the heavy chain variable region sequence set out in SEQ ID NO: 38.

4. The isolated nucleic acid of claim 1 which comprises a sequence encoding an antibody comprising the light chain variable region sequence set out in SEQ ID NO: 39.

5. A method of preparing an antibody which specifically binds the extracellular region of SLC34A2 which comprises expressing the nucleic acid of any of claims 2-4 under conditions to bring about expression of said antibody, and recovering the antibody.

6. A method of preparing an antibody which specifically binds the extracellular region of SLC34A2 which comprises expressing the nucleic acid of claim 1 under conditions to bring about expression of said antibody, and recovering the antibody.

7. A unicellular host transformed with a recombinant DNA molecule comprising a DNA sequence or degenerate variant thereof, which encodes an antibody which specifically binds the extracellular region of SLC34A2, or a fragment thereof, selected from the group consisting of:

(a) the DNA sequence of FIG. 5 (SEQ ID NO: 24), the DNA sequence of FIG. 11 (SEQ ID NO: 36), the DNA sequence of FIG. 16 (SEQ ID NO: 43), or the DNA sequence of FIG. 17 (SEQ ID NO: 45);

(b) the DNA sequence of FIG. 6 (SEQ ID NO: 29), the DNA sequence of FIG. 11 (SEQ ID NO: 34);

(c) the DNA sequence of FIG. 5 (SEQ ID NO: 24) and the DNA sequence of FIG. 6 (SEQ ID NO: 29) or the DNA sequence of SEQ ID NO: 36 and SEQ ID NO: 34;

(d) DNA sequences that hybridize to any of the foregoing DNA sequences under standard hybridization conditions; and (e) DNA sequences that code on expression for an amino acid sequence encoded by any of the foregoing DNA sequences;

wherein said DNA sequence is operatively linked to an expression control sequence.

8. The unicellular host of claim 7, wherein the unicellular host is selected from the group consisting of *E. coli, Pseudomonas, Bacillus, Streptomyces*, yeasts, CHO, YB/20, NSO, SP2/0, R1.1, B-W, L-M, COS 1, COS 7, BSC1, BSC40, and BMT10 cells, plant cells, insect cells, and human cells in tissue culture.

* * * * *

```
                              SEQUENCE LISTING

<160> NUMBER OF SEQ ID NOS: 80

<210> SEQ ID NO 1
<211> LENGTH: 29
<212> TYPE: PRT
<213> ORGANISM: Homo sapiens

<400> SEQUENCE: 1

Ile Asn Val Thr Val Pro Ser Thr Ala Asn Cys Thr Ser Pro Ser Leu
 1               5                  10                  15

Cys Trp Thr Asp Gly Ile Gln Asn Trp Thr Met Lys Asn
            20                  25

<210> SEQ ID NO 2
<211> LENGTH: 29
<212> TYPE: PRT
<213> ORGANISM: Homo sapiens

<400> SEQUENCE: 2

Ile Asn Val Thr Val Pro Ser Thr Ala Asn Ala Thr Ser Pro Ser Leu
 1               5                  10                  15

Cys Trp Thr Asp Gly Ile Gln Asn Trp Thr Met Lys Asn
            20                  25

<210> SEQ ID NO 3
<211> LENGTH: 29
<212> TYPE: PRT
<213> ORGANISM: Homo sapiens

<400> SEQUENCE: 3

Ile Asn Val Thr Val Pro Ser Thr Ala Asn Cys Thr Ser Pro Ser Leu
 1               5                  10                  15

Ala Trp Thr Asp Gly Ile Gln Asn Trp Thr Met Lys Asn
            20                  25

<210> SEQ ID NO 4
<211> LENGTH: 29
<212> TYPE: PRT
<213> ORGANISM: Homo sapiens

<400> SEQUENCE: 4

Ile Asn Val Thr Val Pro Ser Thr Ala Asn Ala Thr Ser Pro Ser Leu
 1               5                  10                  15

Ala Trp Thr Asp Gly Ile Gln Asn Trp Thr Met Lys Asn
            20                  25
```

-continued

```
<210> SEQ ID NO 5
<211> LENGTH: 24
<212> TYPE: PRT
<213> ORGANISM: Homo sapiens

<400> SEQUENCE: 5

Pro Ser Thr Ala Asn Cys Thr Ser Pro Ser Leu Cys Trp Thr Asp Gly
 1               5                  10                  15

Ile Gln Asn Trp Thr Met Lys Asn
            20

<210> SEQ ID NO 6
<211> LENGTH: 21
<212> TYPE: PRT
<213> ORGANISM: Homo sapiens

<400> SEQUENCE: 6

Ala Asn Cys Thr Ser Pro Ser Leu Cys Trp Thr Asp Gly Ile Gln Asn
 1               5                  10                  15

Trp Thr Met Lys Asn
            20

<210> SEQ ID NO 7
<211> LENGTH: 18
<212> TYPE: PRT
<213> ORGANISM: Homo sapiens

<400> SEQUENCE: 7

Thr Ser Pro Ser Leu Cys Trp Thr Asp Gly Ile Gln Asn Trp Thr Met
 1               5                  10                  15

Lys Asn

<210> SEQ ID NO 8
<211> LENGTH: 15
<212> TYPE: PRT
<213> ORGANISM: Homo sapiens

<400> SEQUENCE: 8

Ser Pro Ser Leu Cys Trp Thr Asp Gly Ile Gln Asn Trp Thr Met
 1               5                  10                  15

<210> SEQ ID NO 9
<211> LENGTH: 24
<212> TYPE: PRT
<213> ORGANISM: Homo sapiens

<400> SEQUENCE: 9

Ile Asn Val Thr Val Pro Ser Thr Ala Asn Cys Thr Ser Pro Ser Leu
 1               5                  10                  15

Cys Trp Thr Asp Gly Ile Gln Asn
            20

<210> SEQ ID NO 10
<211> LENGTH: 20
<212> TYPE: PRT
<213> ORGANISM: Homo sapiens

<400> SEQUENCE: 10

Ile Asn Val Thr Val Pro Ser Thr Ala Asn Cys Thr Ser Pro Ser Leu
 1               5                  10                  15

Cys Trp Thr Asp
            20
```

```
<210> SEQ ID NO 11
<211> LENGTH: 15
<212> TYPE: PRT
<213> ORGANISM: Homo sapiens

<400> SEQUENCE: 11

Asn Val Thr Val Pro Ser Thr Ala Asn Cys Thr Ser Pro Ser Leu
1               5                   10                  15

<210> SEQ ID NO 12
<211> LENGTH: 15
<212> TYPE: PRT
<213> ORGANISM: Homo sapiens

<400> SEQUENCE: 12

Pro Ser Thr Ala Asn Cys Thr Ser Pro Ser Leu Cys Trp Thr Asp
1               5                   10                  15

<210> SEQ ID NO 13
<211> LENGTH: 15
<212> TYPE: PRT
<213> ORGANISM: Homo sapiens

<400> SEQUENCE: 13

Ile Asn Val Thr Val Pro Ser Thr Ala Asn Cys Thr Ser Pro Ser
1               5                   10                  15

<210> SEQ ID NO 14
<211> LENGTH: 15
<212> TYPE: PRT
<213> ORGANISM: Homo sapiens

<400> SEQUENCE: 14

Thr Val Pro Ser Thr Ala Asn Cys Thr Ser Pro Ser Leu Cys Trp
1               5                   10                  15

<210> SEQ ID NO 15
<211> LENGTH: 15
<212> TYPE: PRT
<213> ORGANISM: Homo sapiens

<400> SEQUENCE: 15

Ser Thr Ala Asn Cys Thr Ser Pro Ser Leu Cys Trp Thr Asp Gly
1               5                   10                  15

<210> SEQ ID NO 16
<211> LENGTH: 15
<212> TYPE: PRT
<213> ORGANISM: Homo sapiens

<400> SEQUENCE: 16

Asn Cys Thr Ser Pro Ser Leu Cys Trp Thr Asp Gly Ile Gln Asn
1               5                   10                  15

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
tcagccaaat tgcaatgaac                                              20
```

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
acaccaacgg actagtacta                                                    20

<210> SEQ ID NO 19
<211> LENGTH: 8
<212> TYPE: PRT
<213> ORGANISM: Homo sapiens

<400> SEQUENCE: 19

Val Ile Thr Lys Pro Phe Thr Lys
 1               5

<210> SEQ ID NO 20
<211> LENGTH: 8
<212> TYPE: PRT
<213> ORGANISM: Homo sapiens

<400> SEQUENCE: 20

Leu Ile Val Gln Leu Asp Lys Lys
 1               5

<210> SEQ ID NO 21
<211> LENGTH: 4
<212> TYPE: PRT
<213> ORGANISM: Homo sapiens

<400> SEQUENCE: 21

Ile Trp Cys Lys
 1

<210> SEQ ID NO 22
<211> LENGTH: 11
<212> TYPE: PRT
<213> ORGANISM: Homo sapiens

<400> SEQUENCE: 22

Ser Leu Lys Pro Trp Asp Ala Val Val Ser Lys
 1               5                  10

<210> SEQ ID NO 23
<211> LENGTH: 15
<212> TYPE: PRT
<213> ORGANISM: Mus musculus

<400> SEQUENCE: 23

Ser Pro Ser Tyr Cys Trp Thr Asp Gly Ile Gln Asn Trp Thr Ile
 1               5                  10                  15

<210> SEQ ID NO 24
<211> LENGTH: 411
<212> TYPE: DNA
<213> ORGANISM: Mus musculus

<400> SEQUENCE: 24
atgggatgga gctgtatcat cttcttggta gcaacagcta caggtgtcca ctcccaggtg        60
caattgaagc agtctgggc tgagctggtg aagcctgggg cctcagtgaa gatgtcctgt       120
aaggcttccg gctacacatt taccgggtac aatatacact gggtaaagca gacacctgga      180

```
caggggcctgg aatggattgg agctatttat ccaggaaatg gtgatacttc ctacaaacag    240
aagttcagag gcaaggcctc attgactgca gacacatcct ccagtacagt ctatatgcag    300
ctcagcagcc tgacatctga ggactctgcg gtctattact gtgcaagagg ggagacagct    360
cgggctactt tgcttactg gggccaaggg actctggtca ctgtctctgc a              411
```

<210> SEQ ID NO 25
<211> LENGTH: 137
<212> TYPE: PRT
<213> ORGANISM: Mus musculus

<400> SEQUENCE: 25

```
Met Gly Trp Ser Cys Ile Ile Phe Leu Val Ala Thr Ala Thr Gly Val
1               5                   10                  15

His Ser Gln Val Gln Leu Lys Gln Ser Gly Ala Glu Leu Val Lys Pro
            20                  25                  30

Gly Ala Ser Val Lys Met Ser Cys Lys Ala Ser Gly Tyr Thr Phe Thr
        35                  40                  45

Gly Tyr Asn Ile His Trp Val Lys Gln Thr Pro Gly Gln Gly Leu Glu
    50                  55                  60

Trp Ile Gly Ala Ile Tyr Pro Gly Asn Gly Asp Thr Ser Tyr Lys Gln
65                  70                  75                  80

Lys Phe Arg Gly Lys Ala Ser Leu Thr Ala Asp Thr Ser Ser Ser Thr
                85                  90                  95

Val Tyr Met Gln Leu Ser Ser Leu Thr Ser Glu Asp Ser Ala Val Tyr
            100                 105                 110

Tyr Cys Ala Arg Gly Glu Thr Ala Arg Ala Thr Phe Ala Tyr Trp Gly
        115                 120                 125

Gln Gly Thr Leu Val Thr Val Ser Ala
    130                 135
```

<210> SEQ ID NO 26
<211> LENGTH: 10
<212> TYPE: PRT
<213> ORGANISM: Mus musculus

<400> SEQUENCE: 26

```
Gly Tyr Thr Phe Thr Gly Tyr Asn Ile His
1               5                   10
```

<210> SEQ ID NO 27
<211> LENGTH: 17
<212> TYPE: PRT
<213> ORGANISM: Mus musculus

<400> SEQUENCE: 27

```
Ala Ile Tyr Pro Gly Asn Gly Asp Thr Ser Tyr Lys Gln Lys Phe Arg
1               5                   10                  15

Gly
```

<210> SEQ ID NO 28
<211> LENGTH: 10
<212> TYPE: PRT
<213> ORGANISM: Mus musculus

<400> SEQUENCE: 28

```
Gly Glu Thr Ala Arg Ala Thr Phe Ala Tyr
1               5                   10
```

<210> SEQ ID NO 29
<211> LENGTH: 384
<212> TYPE: DNA
<213> ORGANISM: Mus musculus

<400> SEQUENCE: 29

```
atggtgtcct cagctcagtt ccttggtctc ctgttgctct gttttcaagg taccagatgt    60
gatatccaga tgacacagac tacatcctcc ctgcctgcct ctctgggaga cagagtcacc   120
atcagttgca gtgcaagtca ggacattggc aatttttta  actggtatca acagaaacca   180
gatggaactg ttaaagtcct gatctattac acatcaagtt tatactcagg agtcccatca   240
aggttcagtg gcagtgggtc tgggacagac tattctctca ccatcagcaa cctggaacct   300
gaagatattg ccacttacta ttgtcaacag tatagtaaac ttccgctcac gttcggtgct   360
gggaccaagc tcgagctgaa acgg                                          384
```

<210> SEQ ID NO 30
<211> LENGTH: 128
<212> TYPE: PRT
<213> ORGANISM: Mus musculus

<400> SEQUENCE: 30

Met Val Ser Ser Ala Gln Phe Leu Gly Leu Leu Leu Cys Phe Gln
1               5                   10                  15

Gly Thr Arg Cys Asp Ile Gln Met Thr Gln Thr Thr Ser Ser Leu Pro
            20                  25                  30

Ala Ser Leu Gly Asp Arg Val Thr Ile Ser Cys Ser Ala Ser Gln Asp
        35                  40                  45

Ile Gly Asn Phe Leu Asn Trp Tyr Gln Gln Lys Pro Asp Gly Thr Val
    50                  55                  60

Lys Val Leu Ile Tyr Tyr Thr Ser Ser Leu Tyr Ser Gly Val Pro Ser
65                  70                  75                  80

Arg Phe Ser Gly Ser Gly Ser Gly Thr Asp Tyr Ser Leu Thr Ile Ser
            85                  90                  95

Asn Leu Glu Pro Glu Asp Ile Ala Thr Tyr Tyr Cys Gln Gln Tyr Ser
        100                 105                 110

Lys Leu Pro Leu Thr Phe Gly Ala Gly Thr Lys Leu Glu Leu Lys Arg
    115                 120                 125

<210> SEQ ID NO 31
<211> LENGTH: 11
<212> TYPE: PRT
<213> ORGANISM: Mus musculus

<400> SEQUENCE: 31

Ser Ala Ser Gln Asp Ile Gly Asn Phe Leu Asn
1               5                   10

<210> SEQ ID NO 32
<211> LENGTH: 7
<212> TYPE: PRT
<213> ORGANISM: Mus musculus

<400> SEQUENCE: 32

Tyr Thr Ser Ser Leu Tyr Ser
1               5

```
<210> SEQ ID NO 33
<211> LENGTH: 9
<212> TYPE: PRT
<213> ORGANISM: Mus musculus

<400> SEQUENCE: 33

Gln Gln Tyr Ser Lys Leu Pro Leu Thr
  1               5

<210> SEQ ID NO 34
<211> LENGTH: 381
<212> TYPE: DNA
<213> ORGANISM: Mus musculus

<400> SEQUENCE: 34
atggactgga cctggcggat tctgttcctg gtggccgctg ccacaggcgt gcacagcgac      60
atccagatga cccagagccc cagcagcctg agcgccagcg tgggcgacag agtgaccatc     120
acctgcagcg ccagccagga catcggcaac tttctgaact ggtatcagca gaagcccggc     180
aagaccgtca aggtgctgat ctactacacc agctccctgt acagcggcgt gcccagccgg     240
tttagcggaa gcggctccgg caccgactac accctgacca tcagcagcct gcagcccgag     300
gacttcgcca cctactactg ccagcagtac agcaagctgc ccctgacctt cggccagggc     360
accaagctgg aactgaagcg g                                              381

<210> SEQ ID NO 35
<211> LENGTH: 127
<212> TYPE: PRT
<213> ORGANISM: Mus musculus

<400> SEQUENCE: 35

Met Asp Trp Thr Trp Arg Ile Leu Phe Leu Val Ala Ala Thr Gly
  1               5                  10                  15

Val His Ser Asp Ile Gln Met Thr Gln Ser Pro Ser Ser Leu Ser Ala
                 20                  25                  30

Ser Val Gly Asp Arg Val Thr Ile Thr Cys Ser Ala Ser Gln Asp Ile
             35                  40                  45

Gly Asn Phe Leu Asn Trp Tyr Gln Gln Lys Pro Gly Lys Thr Val Lys
         50                  55                  60

Val Leu Ile Tyr Tyr Thr Ser Ser Leu Tyr Ser Gly Val Pro Ser Arg
 65                  70                  75                  80

Phe Ser Gly Ser Gly Ser Gly Thr Asp Tyr Thr Leu Thr Ile Ser Ser
                 85                  90                  95

Leu Gln Pro Glu Asp Phe Ala Thr Tyr Tyr Cys Gln Gln Tyr Ser Lys
            100                 105                 110

Leu Pro Leu Thr Phe Gly Gln Gly Thr Lys Leu Glu Leu Lys Arg
            115                 120                 125

<210> SEQ ID NO 36
<211> LENGTH: 420
<212> TYPE: DNA
<213> ORGANISM: Mus musculus

<400> SEQUENCE: 36
atggactgga cctggaggat tctgtttctg gtggccgcag ccactggagt gcacagccag      60
gtccagctgg tgcagagcgg agccgaggtg gtgaagcctg gcgccagcgt gaagatgagc     120
tgcaaggcca gcggctacac ctttaccggc tacaacatcc actgggtgaa acaggcccct     180
ggacagggac tggaatggat cggcgccatc taccccggca acggcgatac cagctataag     240
```

```
cagaagttcc ggggcagagc caccctgacc gccgacacca gcaccagcac cgtgtacatg    300
gaactgagca gcctgcggag cgaggacagc gccgtgtact actgcgccag aggcgagaca    360
gccagagcca ccttcgccta ctggggacag ggcaccctgg tgaccgtgtc tagcgggggt    420
```

<210> SEQ ID NO 37
<211> LENGTH: 139
<212> TYPE: PRT
<213> ORGANISM: Mus musculus

<400> SEQUENCE: 37

```
Met Asp Trp Thr Trp Arg Ile Leu Phe Leu Val Ala Ala Ala Thr Gly
  1               5                  10                  15

Val His Ser Gln Val Gln Leu Val Gln Ser Gly Ala Glu Val Val Lys
             20                  25                  30

Pro Gly Ala Ser Val Lys Met Ser Cys Lys Ala Ser Gly Tyr Thr Phe
         35                  40                  45

Thr Gly Tyr Asn Ile His Trp Val Lys Gln Ala Pro Gly Gln Gly Leu
     50                  55                  60

Glu Trp Ile Gly Ala Ile Tyr Pro Gly Asn Gly Asp Thr Ser Tyr Lys
 65                  70                  75                  80

Gln Lys Phe Arg Gly Arg Ala Thr Leu Thr Ala Asp Thr Ser Thr Ser
                 85                  90                  95

Thr Val Tyr Met Glu Leu Ser Ser Leu Arg Ser Glu Asp Ser Ala Val
            100                 105                 110

Tyr Tyr Cys Ala Arg Gly Glu Thr Ala Arg Ala Thr Phe Ala Tyr Trp
        115                 120                 125

Gly Gln Gly Thr Leu Val Thr Val Ser Ser Gly
    130                 135
```

<210> SEQ ID NO 38
<211> LENGTH: 119
<212> TYPE: PRT
<213> ORGANISM: Mus musculus

<400> SEQUENCE: 38

```
Gln Val Gln Leu Val Gln Ser Gly Ala Glu Val Val Lys Pro Gly Ala
  1               5                  10                  15

Ser Val Lys Met Ser Cys Lys Ala Ser Gly Tyr Thr Phe Thr Gly Tyr
             20                  25                  30

Asn Ile His Trp Val Lys Gln Ala Pro Gly Gln Gly Leu Glu Trp Ile
         35                  40                  45

Gly Ala Ile Tyr Pro Gly Asn Gly Asp Thr Ser Tyr Lys Gln Lys Phe
     50                  55                  60

Arg Gly Arg Ala Thr Leu Thr Ala Asp Thr Ser Thr Ser Thr Val Tyr
 65                  70                  75                  80

Met Glu Leu Ser Ser Leu Arg Ser Glu Asp Ser Ala Val Tyr Tyr Cys
                 85                  90                  95

Ala Arg Gly Glu Thr Ala Arg Ala Thr Phe Ala Tyr Trp Gly Gln Gly
            100                 105                 110

Thr Leu Val Thr Val Ser Ser
        115
```

<210> SEQ ID NO 39
<211> LENGTH: 107
<212> TYPE: PRT
<213> ORGANISM: Mus musculus

<400> SEQUENCE: 39

Asp Ile Gln Met Thr Gln Ser Pro Ser Leu Ser Ala Ser Val Gly
1               5                   10                  15

Asp Arg Val Thr Ile Thr Cys Ser Ala Ser Gln Asp Ile Gly Asn Phe
            20                  25                  30

Leu Asn Trp Tyr Gln Gln Lys Pro Gly Lys Thr Val Lys Val Leu Ile
        35                  40                  45

Tyr Tyr Thr Ser Ser Leu Tyr Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Lys Leu Pro Leu
                85                  90                  95

Thr Phe Gly Gln Gly Thr Lys Leu Glu Leu Lys
            100                 105

<210> SEQ ID NO 40
<211> LENGTH: 119
<212> TYPE: PRT
<213> ORGANISM: Mus musculus

<400> SEQUENCE: 40

Gln Val Gln Leu Lys Gln Ser Gly Ala Glu Leu Val Lys Pro Gly Ala
1               5                   10                  15

Ser Val Lys Met Ser Cys Lys Ala Ser Gly Tyr Thr Phe Thr Gly Tyr
            20                  25                  30

Asn Ile His Trp Val Lys Gln Thr Pro Gly Gln Gly Leu Glu Trp Ile
        35                  40                  45

Gly Ala Ile Tyr Pro Gly Asn Gly Asp Thr Ser Tyr Lys Gln Lys Phe
50                  55                  60

Arg Gly Lys Ala Ser Leu Thr Ala Asp Thr Ser Ser Ser Thr Val Tyr
65                  70                  75                  80

Met Gln Leu Ser Ser Leu Thr Ser Glu Asp Ser Ala Val Tyr Tyr Cys
                85                  90                  95

Ala Arg Gly Glu Thr Ala Arg Ala Thr Phe Ala Tyr Trp Gly Gln Gly
            100                 105                 110

Thr Leu Val Thr Val Ser Ser
        115

<210> SEQ ID NO 41
<211> LENGTH: 107
<212> TYPE: PRT
<213> ORGANISM: Mus musculus

<400> SEQUENCE: 41

Asp Ile Gln Met Thr Gln Thr Thr Ser Ser Leu Pro Ala Ser Leu Gly
1               5                   10                  15

Asp Arg Val Thr Ile Ser Cys Ser Ala Ser Gln Asp Ile Gly Asn Phe
            20                  25                  30

Leu Asn Trp Tyr Gln Gln Lys Pro Asp Gly Thr Val Lys Val Leu Ile
        35                  40                  45

Tyr Tyr Thr Ser Ser Leu Tyr Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Leu
            85                  90                  95

Thr Phe Gly Ala Gly Thr Lys Leu Glu Leu Lys
            100                 105

<210> SEQ ID NO 42
<211> LENGTH: 279
<212> TYPE: PRT
<213> ORGANISM: Mus musculus
<220> FEATURE:
<221> NAME/KEY: DOMAIN
<222> LOCATION: (1)...(20)
<223> OTHER INFORMATION: signal sequence
<221> NAME/KEY: DOMAIN
<222> LOCATION: (21)...(139)
<223> OTHER INFORMATION: variable heavy chain
<221> NAME/KEY: DOMAIN
<222> LOCATION: (140)...(154)
<223> OTHER INFORMATION: linker
<221> NAME/KEY: DOMAIN
<222> LOCATION: (155)...(261)
<223> OTHER INFORMATION: variable light chain
<221> NAME/KEY: DOMAIN
<222> LOCATION: (262)...(279)
<223> OTHER INFORMATION: E tag

<400> SEQUENCE: 42

Val Lys Lys Leu Leu Phe Ala Ile Pro Leu Val Val Pro Phe Tyr Ala
 1               5                   10                  15

Ala Gln Pro Ala Gln Val Gln Leu Val Gln Ser Gly Ala Glu Val Val
            20                  25                  30

Lys Pro Gly Ala Ser Val Lys Met Ser Cys Lys Ala Ser Gly Tyr Thr
            35                  40                  45

Phe Thr Gly Tyr Asn Ile His Trp Val Lys Gln Ala Pro Gly Gln Gly
        50                  55                  60

Leu Glu Trp Ile Gly Ala Ile Tyr Pro Gly Asn Gly Asp Thr Ser Tyr
65                  70                  75                  80

Lys Gln Lys Phe Arg Gly Arg Ala Thr Leu Thr Ala Asp Thr Ser Thr
            85                  90                  95

Ser Thr Val Tyr Met Glu Leu Ser Ser Leu Arg Ser Glu Asp Ser Ala
            100                 105                 110

Val Tyr Tyr Cys Ala Arg Gly Glu Thr Ala Arg Ala Thr Phe Ala Tyr
        115                 120                 125

Trp Gly Gln Gly Thr Leu Val Thr Val Ser Ser Gly Gly Gly Gly Ser
        130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Ser Ala Ser Gln Asp Ile Gly Asn Phe Leu Asn Trp Tyr Gln Gln
            180                 185                 190

Lys Pro Gly Lys Thr Val Lys Val Leu Ile Tyr Tyr Thr Ser Ser Leu
            195                 200                 205

Tyr Ser Gly Val Pro Ser Arg Phe Ser Gly Ser Gly Ser Gly Thr Asp
        210                 215                 220

Tyr Thr Leu Thr Ile Ser Ser Leu Gln Pro Glu Asp Phe Ala Thr Tyr
225                 230                 235                 240

Tyr Cys Gln Gln Tyr Ser Lys Leu Pro Leu Thr Phe Gly Gln Gly Thr
            245                 250                 255

Lys Leu Glu Leu Lys Ala Ala Ala Gly Ala Pro Val Pro Tyr Pro Asp
       260                 265                 270

Pro Leu Glu Pro Arg Ala Ala
        275

<210> SEQ ID NO 43
<211> LENGTH: 840
<212> TYPE: DNA
<213> ORGANISM: Mus musculus

<400> SEQUENCE: 43
gtgaaaaaat tattattcgc aattccttta gttgttcctt tctatgcggc ccagccggcc    60
caggtgcagc tggtgcagag cggcgctgaa gtggtgaagc tggcgctag cgtgaagatg   120 agctgcaagg ccagcggcta caccttcacc ggctacaaca tccattgggt gaagcaggct   180
ccaggccagg gcctcgaatg gatcggcgcc atctaccccg gcaacggcga tacctcttac   240
aagcagaagt tcaggggcag ggctaccctc accgccgaca ccagcaccag caccgtgtac   300
atggaactgt ccagcctgag aagcgaggac agcgccgtgt actactgcgc caggggcgag   360
accgccaggg ccaccttcgc ctactggggc cagggcaccc tggtgactgt atcatccggt   420
ggaggcggtt caggcggagg tggctctggc ggtggcggat cggacatcca gatgacccag   480
agccccagca gcctgagcgc cagcgtgggc gacagggtga ccatcacctg cagcgccagc   540
caggacatcg gcaactttct gaactggtat cagcagaagc ccggcaagac cgtcaaggtg   600
ctgatctact acaccagctc cctgtacagc ggcgtgccca gcaggttcag cggcagcggc   660
tccggcaccg actacaccct gaccatcagc agcctgcagc ccgaggactt cgccacctac   720
tactgccagc agtacagcaa gctgcccctg accttcggcc agggcaccaa actggaactc   780
aaagcggccg caggtgcgcc ggtgccgtat ccggatccgc tggaaccgcg tgccgcatag   840

<210> SEQ ID NO 44
<211> LENGTH: 279
<212> TYPE: PRT
<213> ORGANISM: Mus musculus
<220> FEATURE:
<221> NAME/KEY: DOMAIN
<222> LOCATION: (1)...(20)
<223> OTHER INFORMATION: signal sequence
<221> NAME/KEY: DOMAIN
<222> LOCATION: (21)...(139)
<223> OTHER INFORMATION: variable heavy chain
<221> NAME/KEY: DOMAIN
<222> LOCATION: (140)...(154)
<223> OTHER INFORMATION: linker
<221> NAME/KEY: DOMAIN
<222> LOCATION: (155)...(261)
<223> OTHER INFORMATION: variable light chain
<221> NAME/KEY: DOMAIN
<222> LOCATION: (262)...(279)
<223> OTHER INFORMATION: E tag

<400> SEQUENCE: 44

Val Lys Lys Leu Leu Phe Ala Ile Pro Leu Val Val Pro Phe Tyr Ala
 1               5                  10                  15

Ala Gln Pro Ala Gln Val Gln Leu Lys Gln Ser Gly Ala Glu Leu Val
            20                  25                  30

Lys Pro Gly Ala Ser Val Lys Met Ser Cys Lys Ala Ser Gly Tyr Thr
        35                  40                  45

Phe Thr Gly Tyr Asn Ile His Trp Val Lys Gln Thr Pro Gly Gln Gly
    50                  55                  60

```
Leu Glu Trp Ile Gly Ala Ile Tyr Pro Gly Asn Gly Asp Thr Ser Tyr
 65                  70                  75                  80

Lys Gln Lys Phe Arg Gly Lys Ala Ser Leu Thr Ala Asp Thr Ser Ser
                 85                  90                  95

Ser Thr Val Tyr Met Gln Leu Ser Ser Leu Thr Ser Glu Asp Ser Ala
            100                 105                 110

Val Tyr Tyr Cys Ala Arg Gly Glu Thr Ala Arg Ala Thr Phe Ala Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Asp Ile Gln Met Thr Gln
145                 150                 155                 160

Thr Thr Ser Ser Leu Pro Ala Ser Leu Gly Asp Arg Val Thr Ile Ser
                165                 170                 175

Cys Ser Ala Ser Gln Asp Ile Gly Asn Phe Leu Asn Trp Tyr Gln Gln
            180                 185                 190

Lys Pro Asp Gly Thr Val Lys Val Leu Ile Tyr Tyr Thr Ser Ser Leu
        195                 200                 205

Tyr Ser Gly Val Pro Ser Arg Phe Ser Gly Ser Gly Ser Gly Thr Asp
210                 215                 220

Tyr Ser Leu Thr Ile Ser Asn Leu Glu Pro Glu Asp Ile Ala Thr Tyr
225                 230                 235                 240

Tyr Cys Gln Gln Tyr Ser Lys Leu Pro Leu Thr Phe Gly Ala Gly Thr
                245                 250                 255

Lys Leu Glu Leu Lys Ala Ala Ala Gly Ala Pro Val Pro Tyr Pro Asp
            260                 265                 270

Pro Leu Glu Pro Arg Ala Ala
            275
```

<210> SEQ ID NO 45
<211> LENGTH: 840
<212> TYPE: DNA
<213> ORGANISM: Mus musculus

<400> SEQUENCE: 45

```
gtgaaaaaat tattattcgc aattcctttg gttgttcctt tctatgcggc ccagccggcc    60
caggtgcaat tgaagcagtc tggggccgag ctggtgaagc aggcgccag cgtgaagatg   120 agctgcaagg ccagcggcta caccttcacc ggctacaaca tccactgggt caagcagacc   180
ccaggccagg gctggagtg atcggcgcc atctaccccg gcaacggcga caccagctac    240
aagcagaagt tcaggggcaa ggccagcctc accgccgaca ccagcagcag caccgtgtac   300
atgcagctgt ccagtctcac cagcgaagat agcgccgtgt actactgtgc cagaggcgag   360
accgccagag ccaccttcgc ctactgggc cagggcaccc tggtgaccgt gtcatccggt    420
ggaggcggtt caggcggagg tggctctggc ggtggcggat cggatatcca gatgacccag   480
accacctcca gcctgcccgc cagcctgggc gacagagtga ccatcagctg ctccgccagc   540
caggacatcg gcaactttct gaactggtat cagcagaagc cgacggcac cgtcaaggtg    600 ctcatctact acaccagcag cctgtacagc ggcgtgccaa gcagattcag cggcagcggc   660
tccggcaccg actacagcct caccatctcc aacctggagc cagaggacat cgccacctac   720
tactgccagc agtacagcaa gctgccactc accttcggag ccggcaccaa gctggagctg   780
aaagcggccg caggtgcgcc ggtgccgtat ccggatccgc tggaaccgcg tgccgcatag   840
```

<210> SEQ ID NO 46
<211> LENGTH: 36
<212> TYPE: DNA
<213> ORGANISM: Artificial Sequence
<220> FEATURE:
<223> OTHER INFORMATION: primer

<400> SEQUENCE: 46
cacggcccag ccggcccagg tgcagctcca agagag            36

<210> SEQ ID NO 47
<211> LENGTH: 37
<212> TYPE: DNA
<213> ORGANISM: Artificial Sequence
<220> FEATURE:
<223> OTHER INFORMATION: primer

<400> SEQUENCE: 47
cacggcccag ccggcccagg tgcagctggt gcagagc           37

<210> SEQ ID NO 48
<211> LENGTH: 37
<212> TYPE: DNA
<213> ORGANISM: Artificial Sequence
<220> FEATURE:
<223> OTHER INFORMATION: primer

<400> SEQUENCE: 48
cacggcccag ccggcccagg tgcaattgaa gcagtct           37

<210> SEQ ID NO 49
<211> LENGTH: 46
<212> TYPE: DNA
<213> ORGANISM: Artificial Sequence
<220> FEATURE:
<223> OTHER INFORMATION: primer

<400> SEQUENCE: 49
ccacctccgc ctgaaccgcc tccaccgctg ctcactgtca ctaggg    46

<210> SEQ ID NO 50
<211> LENGTH: 46
<212> TYPE: DNA
<213> ORGANISM: Artificial Sequence
<220> FEATURE:
<223> OTHER INFORMATION: primer

<400> SEQUENCE: 50
ccctagtgac agtgagcagc ggtggaggcg gttcaggcgg aggtgg    46

<210> SEQ ID NO 51
<211> LENGTH: 46
<212> TYPE: DNA
<213> ORGANISM: Artificial Sequence
<220> FEATURE:
<223> OTHER INFORMATION: primer

<400> SEQUENCE: 51
ccacctccgc ctgaaccgcc tccaccggat gatacagtca ccaggg    46

<210> SEQ ID NO 52
<211> LENGTH: 46
<212> TYPE: DNA
<213> ORGANISM: Artificial Sequence
<220> FEATURE:
<223> OTHER INFORMATION: primer

```
<400> SEQUENCE: 52
ccctggtgac tgtatcatcc ggtggaggcg gttcaggcgg aggtgg                    46

<210> SEQ ID NO 53
<211> LENGTH: 46
<212> TYPE: DNA
<213> ORGANISM: Artificial Sequence
<220> FEATURE:
<223> OTHER INFORMATION: primer

<400> SEQUENCE: 53
ccacctccgc ctgaaccgcc tccaccggat gacacggtca ccaggg                    46

<210> SEQ ID NO 54
<211> LENGTH: 46
<212> TYPE: DNA
<213> ORGANISM: Artificial Sequence
<220> FEATURE:
<223> OTHER INFORMATION: primer

<400> SEQUENCE: 54
ccctggtgac cgtgtcatcc ggtggaggcg gttcaggcgg aggtgg                    46

<210> SEQ ID NO 55
<211> LENGTH: 54
<212> TYPE: DNA
<213> ORGANISM: Artificial Sequence
<220> FEATURE:
<223> OTHER INFORMATION: primer

<400> SEQUENCE: 55
caggcggagg tggctctggc ggtggcggat cggatattca gatgactcag agtc           54

<210> SEQ ID NO 56
<211> LENGTH: 54
<212> TYPE: DNA
<213> ORGANISM: Artificial Sequence
<220> FEATURE:
<223> OTHER INFORMATION: primer

<400> SEQUENCE: 56
caggcggagg tggctctggc ggtggcggat cggacatcca gatgacccag agcc           54

<210> SEQ ID NO 57
<211> LENGTH: 54
<212> TYPE: DNA
<213> ORGANISM: Artificial Sequence
<220> FEATURE:
<223> OTHER INFORMATION: primer

<400> SEQUENCE: 57
caggcggagg tggctctggc ggtggcggat cggatatcca gatgacccag acca           54

<210> SEQ ID NO 58
<211> LENGTH: 35
<212> TYPE: DNA
<213> ORGANISM: Artificial Sequence
<220> FEATURE:
<223> OTHER INFORMATION: primer

<400> SEQUENCE: 58
cctgcggccg ctttgatttc cagttttgtg ccgcc                                35
```

```
<210> SEQ ID NO 59
<211> LENGTH: 35
<212> TYPE: DNA
<213> ORGANISM: Artificial Sequence
<220> FEATURE:
<223> OTHER INFORMATION: primer

<400> SEQUENCE: 59
ggcggcacaa aactggaaat caaagcggcc gcagg                               35

<210> SEQ ID NO 60
<211> LENGTH: 35
<212> TYPE: DNA
<213> ORGANISM: Artificial Sequence
<220> FEATURE:
<223> OTHER INFORMATION: primer

<400> SEQUENCE: 60
cctgcggccg ctttgagttc cagtttggtg ccctg                               35

<210> SEQ ID NO 61
<211> LENGTH: 35
<212> TYPE: DNA
<213> ORGANISM: Artificial Sequence
<220> FEATURE:
<223> OTHER INFORMATION: primer

<400> SEQUENCE: 61
cagggcacca aactggaact caaagcggcc gcagg                               35

<210> SEQ ID NO 62
<211> LENGTH: 35
<212> TYPE: DNA
<213> ORGANISM: Artificial Sequence
<220> FEATURE:
<223> OTHER INFORMATION: primer

<400> SEQUENCE: 62
cctgcggccg ctttcagctc cagcttggtg ccggc                               35

<210> SEQ ID NO 63
<211> LENGTH: 35
<212> TYPE: DNA
<213> ORGANISM: Artificial Sequence
<220> FEATURE:
<223> OTHER INFORMATION: primer

<400> SEQUENCE: 63
gccggcacca agctggagct gaaagcggcc gcagg                               35

<210> SEQ ID NO 64
<211> LENGTH: 26
<212> TYPE: DNA
<213> ORGANISM: Artificial Sequence
<220> FEATURE:
<223> OTHER INFORMATION: primer

<400> SEQUENCE: 64
ccatgattac gccaagcttt ggagcc                                         26

<210> SEQ ID NO 65
<211> LENGTH: 25
<212> TYPE: DNA
<213> ORGANISM: Artificial Sequence
<220> FEATURE:
<223> OTHER INFORMATION: primer
```

```
<400> SEQUENCE: 65
cgatctaaag ttttgtcgtc tttcc                                          25

<210> SEQ ID NO 66
<211> LENGTH: 20
<212> TYPE: DNA
<213> ORGANISM: Artificial Sequence
<220> FEATURE:
<223> OTHER INFORMATION: primer

<400> SEQUENCE: 66
gattacgcca agctttggag                                                20

<210> SEQ ID NO 67
<211> LENGTH: 42
<212> TYPE: DNA
<213> ORGANISM: Artificial Sequence
<220> FEATURE:
<223> OTHER INFORMATION: primer

<400> SEQUENCE: 67
cttcaattgc acctgggccg gctgggccgc atagaaagga ac                       42

<210> SEQ ID NO 68
<211> LENGTH: 15
<212> TYPE: PRT
<213> ORGANISM: Homo sapiens

<400> SEQUENCE: 68

Ser Pro Ser Leu Cys Trp Met Asp Gly Ile Gln Asn Trp Thr Met
 1               5                  10                  15

<210> SEQ ID NO 69
<211> LENGTH: 26
<212> TYPE: DNA
<213> ORGANISM: Artificial Sequence
<220> FEATURE:
<223> OTHER INFORMATION: primer

<400> SEQUENCE: 69
agtggatcca tggctccctg gcctga                                         26

<210> SEQ ID NO 70
<211> LENGTH: 52
<212> TYPE: DNA
<213> ORGANISM: Artificial Sequence
<220> FEATURE:
<223> OTHER INFORMATION: primer

<400> SEQUENCE: 70
cggaattcct actccatcgg catgaactcc atcaaggccg tgcattcggt ct            52

<210> SEQ ID NO 71
<211> LENGTH: 44
<212> TYPE: DNA
<213> ORGANISM: Artificial Sequence
<220> FEATURE:
<223> OTHER INFORMATION: primer

<400> SEQUENCE: 71
gccgaagaaa ctccagaact ggatgcgctc gctgaagccc tggg                    44
```

```
<210> SEQ ID NO 72
<211> LENGTH: 44
<212> TYPE: DNA
<213> ORGANISM: Artificial Sequence
<220> FEATURE:
<223> OTHER INFORMATION: primer

<400> SEQUENCE: 72
cccagggctt cagcgagcgc atccagttct ggagtttctt cggc                    44

<210> SEQ ID NO 73
<211> LENGTH: 42
<212> TYPE: DNA
<213> ORGANISM: Artificial Sequence
<220> FEATURE:
<223> OTHER INFORMATION: primer

<400> SEQUENCE: 73
ctccccttcc ctctgttggg tggatggcat ccaaaactgg ac                      42

<210> SEQ ID NO 74
<211> LENGTH: 42
<212> TYPE: DNA
<213> ORGANISM: Artificial Sequence
<220> FEATURE:
<223> OTHER INFORMATION: primer

<400> SEQUENCE: 74
gtccagtttt ggatgccatc cacccaacag agggaagggg ag                      42

<210> SEQ ID NO 75
<211> LENGTH: 21
<212> TYPE: DNA
<213> ORGANISM: Artificial Sequence
<220> FEATURE:
<223> OTHER INFORMATION: primer

<400> SEQUENCE: 75
gtcatcacta agcccttcac a                                             21

<210> SEQ ID NO 76
<211> LENGTH: 18
<212> TYPE: DNA
<213> ORGANISM: Artificial Sequence
<220> FEATURE:
<223> OTHER INFORMATION: primer

<400> SEQUENCE: 76
caggcaacca cagaggac                                                 18

<210> SEQ ID NO 77
<211> LENGTH: 690
<212> TYPE: PRT
<213> ORGANISM: Homo sapiens

<400> SEQUENCE: 77

Met Ala Pro Trp Pro Glu Leu Gly Asp Ala Gln Pro Asn Pro Asp Lys
1               5                   10                  15

Tyr Leu Glu Gly Ala Ala Gly Gln Gln Pro Thr Ala Pro Asp Lys Ser
            20                  25                  30

Lys Glu Thr Asn Lys Thr Asp Asn Thr Glu Ala Pro Val Thr Lys Ile
        35                  40                  45

Glu Leu Leu Pro Ser Tyr Ser Thr Ala Thr Leu Ile Asp Glu Pro Thr
    50                  55                  60
```

```
Glu Val Asp Asp Pro Trp Asn Leu Pro Thr Leu Gln Asp Ser Gly Ile
65                  70                  75                  80

Lys Trp Ser Glu Arg Asp Thr Lys Gly Lys Ile Leu Cys Phe Phe Gln
            85                  90                  95

Gly Ile Gly Arg Leu Ile Leu Leu Gly Phe Leu Tyr Phe Phe Val
            100                 105                 110

Cys Ser Leu Asp Ile Leu Ser Ser Ala Phe Gln Leu Val Gly Gly Lys
            115                 120                 125

Met Ala Gly Gln Phe Phe Ser Asn Ser Ser Ile Met Ser Asn Pro Leu
            130                 135                 140

Leu Gly Leu Val Ile Gly Val Leu Val Thr Val Leu Val Gln Ser Ser
145                 150                 155                 160

Ser Thr Ser Thr Ser Ile Val Val Ser Met Val Ser Ser Ser Leu Leu
            165                 170                 175

Thr Val Arg Ala Ala Ile Pro Ile Ile Met Gly Ala Asn Ile Gly Thr
            180                 185                 190

Ser Ile Thr Asn Thr Ile Val Ala Leu Met Gln Val Gly Asp Arg Ser
            195                 200                 205

Glu Phe Arg Arg Ala Phe Ala Gly Ala Thr Val His Asp Phe Phe Asn
            210                 215                 220

Trp Leu Ser Val Leu Val Leu Leu Pro Val Glu Val Ala Thr His Tyr
225                 230                 235                 240

Leu Glu Ile Ile Thr Gln Leu Ile Val Glu Ser Phe His Phe Lys Asn
            245                 250                 255

Gly Glu Asp Ala Pro Asp Leu Leu Lys Val Ile Thr Lys Pro Phe Thr
            260                 265                 270

Lys Leu Ile Val Gln Leu Asp Lys Lys Val Ile Ser Gln Ile Ala Met
            275                 280                 285

Asn Asp Glu Lys Ala Lys Asn Lys Ser Leu Val Lys Ile Trp Cys Lys
            290                 295                 300

Thr Phe Thr Asn Lys Thr Gln Ile Asn Val Thr Val Pro Ser Thr Ala
305                 310                 315                 320

Asn Cys Thr Ser Pro Ser Leu Cys Trp Thr Asp Gly Ile Gln Asn Trp
            325                 330                 335

Thr Met Lys Asn Val Thr Tyr Lys Glu Asn Ile Ala Lys Cys Gln His
            340                 345                 350

Ile Phe Val Asn Phe His Leu Pro Asp Leu Ala Val Gly Thr Ile Leu
            355                 360                 365

Leu Ile Leu Ser Leu Leu Val Leu Cys Gly Cys Leu Ile Met Ile Val
            370                 375                 380

Lys Ile Leu Gly Ser Val Leu Lys Gly Gln Val Ala Thr Val Ile Lys
385                 390                 395                 400

Lys Thr Ile Asn Thr Asp Phe Pro Phe Pro Phe Ala Trp Leu Thr Gly
            405                 410                 415

Tyr Leu Ala Ile Leu Val Gly Ala Gly Met Thr Phe Ile Val Gln Ser
            420                 425                 430

Ser Ser Val Phe Thr Ser Ala Leu Thr Pro Leu Ile Gly Ile Gly Val
            435                 440                 445

Ile Thr Ile Glu Arg Ala Tyr Pro Leu Thr Leu Gly Ser Asn Ile Gly
450                 455                 460
```

```
Thr Thr Thr Thr Ala Ile Leu Ala Ala Leu Ala Ser Pro Gly Asn Ala
465                 470                 475                 480

Leu Arg Ser Ser Leu Gln Ile Ala Leu Cys His Phe Phe Phe Asn Ile
            485                 490                 495

Ser Gly Ile Leu Leu Trp Tyr Pro Ile Pro Phe Thr Arg Leu Pro Ile
            500                 505                 510

Arg Met Ala Lys Gly Leu Gly Asn Ile Ser Ala Lys Tyr Arg Trp Phe
            515                 520                 525

Ala Val Phe Tyr Leu Ile Ile Phe Phe Phe Leu Ile Pro Leu Thr Val
            530                 535                 540

Phe Gly Leu Ser Leu Ala Gly Trp Arg Val Leu Val Gly Val Gly Val
545                 550                 555                 560

Pro Val Val Phe Ile Ile Ile Leu Val Leu Cys Leu Arg Leu Leu Gln
                565                 570                 575

Ser Arg Cys Pro Arg Val Leu Pro Lys Lys Leu Gln Asn Trp Asn Phe
            580                 585                 590

Leu Pro Leu Trp Met Arg Ser Leu Lys Pro Trp Asp Ala Val Val Ser
            595                 600                 605

Lys Phe Thr Gly Cys Phe Gln Met Arg Cys Cys Cys Cys Cys Arg Val
610                 615                 620

Cys Cys Arg Ala Cys Cys Leu Leu Cys Gly Cys Pro Lys Cys Cys Arg
625                 630                 635                 640

Cys Ser Lys Cys Cys Glu Asp Leu Glu Glu Ala Gln Glu Gly Gln Asp
                645                 650                 655

Val Pro Val Lys Ala Pro Glu Thr Phe Asp Asn Ile Thr Ile Ser Arg
            660                 665                 670

Glu Ala Gln Gly Glu Val Pro Ala Ser Asp Ser Lys Thr Glu Cys Thr
            675                 680                 685

Ala Leu
    690

<210> SEQ ID NO 78
<211> LENGTH: 48
<212> TYPE: PRT
<213> ORGANISM: Homo sapiens

<400> SEQUENCE: 78

Cys Lys Thr Phe Thr Asn Lys Thr Gln Ile Asn Val Thr Val Pro Ser
1               5                   10                  15

Thr Ala Asn Cys Thr Ser Pro Ser Leu Cys Trp Thr Asp Gly Ile Gln
            20                  25                  30

Asn Trp Thr Met Lys Asn Val Thr Tyr Lys Glu Asn Ile Ala Lys Cys
        35                  40                  45

<210> SEQ ID NO 79
<211> LENGTH: 321
<212> TYPE: DNA
<213> ORGANISM: Mus musculus

<400> SEQUENCE: 79
gacatccaga tgacccagag ccccagcagc ctgagcgcca gcgtgggcga cagggtgacc      60
atcacctgca gcgccagcca ggacatcggc aactttctga actggtatca gcagaagccc     120
ggcaagaccg tcaaggtgct gatctactac accagctccc tgtacagcgg cgtgcccagc     180
aggttcagcg gcagcggctc cggcaccgac tacaccctga ccatcagcag cctgcagccc     240
```

-continued

```
gaggacttcg ccacctacta ctgccagcag tacagcaagc tgcccctgac cttcggccag    300
ggcaccaaac tggaactcaa a                                              321

<210> SEQ ID NO 80
<211> LENGTH: 357
<212> TYPE: DNA
<213> ORGANISM: Mus musculus

<400> SEQUENCE: 80
caggtgcagc tggtgcagag cggcgctgaa gtggtgaagc ctggcgctag cgtgaagatg     60
agctgcaagg ccagcggcta caccttcacc ggctacaaca tccattgggt gaagcaggct    120
ccaggccagg gcctcgaatg gatcggcgcc atctacccccg gcaacggcga tacctcttac   180
aagcagaagt tcaggggcag ggctaccctc accgccgaca ccagcaccag caccgtgtac    240
atggaactgt ccagcctgag aagcgaggac agcgccgtgt actactgcgc caggggcgag    300
accgccaggg ccaccttcgc ctactggggc cagggcaccc tggtgactgt atcatcc       357
```